(12) United States Patent
Chae et al.

(10) Patent No.: US 10,208,309 B2
(45) Date of Patent: Feb. 19, 2019

(54) DOUBLE-STRANDED OLIGO RNA TARGETED TO AMPHIREGULIN AND PHARMACEUTICAL COMPOSITION COMPRISING SAME FOR PREVENTING OR TREATING FIBROSIS OR RESPIRATORY DISEASES

(71) Applicant: Bioneer Corporation, Daejeon (KR)

(72) Inventors: Jeiwook Chae, Daejeon (KR); Pyoung Oh Yoon, Daejeon (KR); Boram Han, Gyeonggi-do (KR); Mi Na Kim, Daejeon (KR); Youngho Ko, Seoul (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 15/301,713

(22) PCT Filed: Apr. 6, 2015

(86) PCT No.: PCT/KR2015/003400
§ 371 (c)(1),
(2) Date: Jan. 19, 2017

(87) PCT Pub. No.: WO2015/152693
PCT Pub. Date: Oct. 8, 2015

(65) Prior Publication Data
US 2017/0130231 A1    May 11, 2017

(30) Foreign Application Priority Data
Apr. 4, 2014  (KR) .................. 10-2014-0040699

(51) Int. Cl.
*C12N 15/113* (2010.01)
(52) U.S. Cl.
CPC ........ *C12N 15/1136* (2013.01); *C12N 15/113* (2013.01); *C12N 2310/14* (2013.01); *C12N 2310/351* (2013.01); *C12N 2310/3515* (2013.01); *C12N 2320/32* (2013.01)
(58) Field of Classification Search
None
See application file for complete search history.

(56) References Cited

U.S. PATENT DOCUMENTS

| | | | |
|---|---|---|---|
| 5,034,323 A | 7/1991 | Jorgensen et al. | |
| 5,231,020 A | 7/1993 | Jorgensen et al. | |
| 5,283,184 A | 2/1994 | Jorgensen et al. | |
| 5,660,985 A | 8/1997 | Pieken et al. | |
| 5,753,263 A | 5/1998 | Lishko et al. | |
| 5,808,023 A | 9/1998 | Sanghvi et al. | |
| 5,958,691 A | 9/1999 | Pieken et al. | |
| 6,175,001 B1 | 1/2001 | Barbas et al. | |
| 6,326,358 B1 | 12/2001 | Manoharan | |
| 6,531,584 B1 | 3/2003 | Cook et al. | |
| 7,691,997 B2 * | 4/2010 | Khvorova | A61K 31/713 536/24.5 |
| 2006/0078624 A1 | 4/2006 | Zalipsky et al. | |
| 2006/0166919 A1 | 7/2006 | Shepard et al. | |
| 2007/0149470 A1 * | 6/2007 | Kaspar | C12N 15/1131 514/44 A |
| 2008/0153737 A1 | 6/2008 | Lieberman et al. | |
| 2008/0227727 A1 | 9/2008 | Erez et al. | |
| 2009/0047338 A1 | 2/2009 | Swamy et al. | |
| 2009/0209626 A1 * | 8/2009 | Khvorova | C12N 15/111 514/44 A |
| 2012/0108803 A1 * | 5/2012 | Han | C07H 21/02 536/24.5 |

(Continued)

FOREIGN PATENT DOCUMENTS

| | | |
|---|---|---|
| CN | 102439148 A | 5/2012 |
| EP | 1449538 A1 | 8/2004 |

(Continued)

OTHER PUBLICATIONS

Akhtar, S., et al., "Nonviral delivery of synthetic siRNAs in vivo", "The Journal of Clinical Investigation", Dec. 2007, pp. 3623-3632, vol. 117, No. 12.

(Continued)

*Primary Examiner* — Tracy Vivlemore
(74) *Attorney, Agent, or Firm* — Hultquist, PLLC; Steven J. Hultquist

(57) ABSTRACT

The present invention relates to a novel siRNA, and a high-efficiency double-stranded oligo RNA structure containing the same, and a nanoparticle containing the high-efficiency double-stranded oligo RNA structure. The double-stranded oligo RNA structure has a structure in which a hydrophilic material and a hydrophobic material are conjugated to both ends of a double-stranded oligo RNA (siRNA) via a simple covalent bond or linker-mediated covalent bond in order to be efficiently delivered into cells, and may be converted into a nanoparticle form in an aqueous solution by hydrophobic interactions of double-stranded oligo RNA structures. It is preferable that the siRNA contained in the double-stranded oligo RNA structure is an siRNA specific for fibrosis or respiratory disease-related gene, particularly, amphiregulin or stratifin.

In addition, the present invention relates to a pharmaceutical composition for preventing or treating fibrosis or respiratory diseases, containing an siRNA, a high-efficiency double-stranded oligo RNA structure containing the siRNA, or a nanoparticle containing the high-efficiency double-stranded oligo RNA structure, as an active ingredient.

In addition, the present invention relates to a method of preventing or treating fibrosis or respiratory diseases, including administering the pharmaceutical composition for preventing or treating fibrosis or respiratory diseases to a subject in need thereof.

29 Claims, 9 Drawing Sheets
Specification includes a Sequence Listing.

(56) References Cited

U.S. PATENT DOCUMENTS

| | | | |
|---|---|---|---|
| 2012/0202871 A1 | 8/2012 | Heyes et al. | |
| 2012/0231069 A1* | 9/2012 | Nowotnik | B82Y 5/00 424/450 |
| 2014/0371432 A1 | 12/2014 | Chae et al. | |
| 2015/0259690 A1* | 9/2015 | Park | C12N 15/1136 514/44 A |
| 2015/0274698 A1 | 10/2015 | Sandanayaka et al. | |

FOREIGN PATENT DOCUMENTS

| | | | | |
|---|---|---|---|---|
| EP | 2905337 | A1 | 8/2015 | |
| JP | 2006518352 | A | 8/2006 | |
| JP | 2010-505934 | A | 2/2010 | |
| JP | 2011-148798 | A | 8/2011 | |
| JP | 2012-526548 | A | 11/2012 | |
| JP | 2013102767 | A | 5/2013 | |
| KR | 10-0883471 | B1 | 2/2009 | |
| KR | 10-1087614 | B1 | 11/2011 | |
| KR | 10-2012-0080562 | A | 7/2012 | |
| KR | 10-1224828 | B1 | 1/2013 | |
| WO | 9932619 | A1 | 7/1999 | |
| WO | 2003070969 | A2 | 8/2003 | |
| WO | 2004009769 | A2 | 1/2004 | |
| WO | 2007021142 | A1 | 2/2007 | |
| WO | 2010076935 | A1 | 7/2010 | |
| WO | 2010108108 | A2 | 9/2010 | |
| WO | WO-2012102793 | A2 * | 8/2012 | A61K 31/7088 |
| WO | 2013059496 | A1 | 4/2013 | |
| WO | 2013089522 | A1 | 6/2013 | |
| WO | 2013103249 | A1 | 7/2013 | |

OTHER PUBLICATIONS

Amarzguioui, M., et al., "Tolerance for mutations and chemical modifications in a siRNA", "Nucleic Acids Research", Jan. 15, 2003, pp. 589-595, vol. 31, No. 2.
Behlke, M., "Progress Towards in Vivo Use of siRNAs", "Molecular Therapy", Feb. 14, 2006, pp. 644-670, vol. 13, No. 4.
Chiu, Y., et al., "siRNA function in RNAi: A chemical modification analysis", "RNA", Sep. 2003, pp. 1034-1048, vol. 9.
Elbashir, S., et al., "Duplexes of 21-nucleotide RNAs mediate RNA interference in cultured mammalian cells", "Nature", May 24, 2001, pp. 494-498, vol. 411.
Fire, A., et al, "Potent and specific genetic interference by double-stranded RNA in Caenorhabditis elegans", "Nature", Feb. 19, 1998, pp. 806-811, vol. 391.
Kennerdell, J., et al., "Use of dsRNA-Mediated Genetic Interference to Demonstrate that frizzled and frizzled 2 Act in the Wingless Pathway", "Cell", Dec. 23, 1998, pp. 1017-1026, vol. 95, Publisher: Cell Press.
Napoli, C., et al., "Introduction of a Chimeric Chalcone Synthase Gene into Petunia Results in Reversible Co-Suppression of Homologous Genes n trans", "The Plant Cell", Apr. 1990, pp. 279-289, vol. 2, Publisher: American Society of Plant Physiologists.
Novina, C., et al, "The RNAi revolution", "Nature", Jul. 8, 2004, pp. 161-164, vol. 430.
Pauwels, R., et al., "Global Strategy for the Diagnosis, Management, and Prevention of Chronic Obstructive Pulmonary Disease. NHLBI/WHO Global Initiative for Chronic Obstructive Lung Disease (GOLD) Workshop summary.", "Am. J. Respir. Crit. Care Med.", Apr. 2001, pp. 1256-1276, vol. 163.
Sheehy, R., et al., "Reduction of Polygalacturonase Activity in Tomato Fruit by Antisense RNA", "Proceedings of the National Academy of Sciences", Dec. 1988, pp. 8805-8809, vol. 85.

Vaish, N., et al., "Improved specificity of gene silencing by siRNAs containing unlocked nucleobase analogs", "Nucleic Acids Research", Nov. 2, 2010, pp. 1823-1832, vol. 39, No. 5.
Van Der Krol, A., et al, "Flavonoid Genes in Petunia: Addition of a Limited Number of Gene Copies May Lead to a Suppression of Gene Expression", "The Plant Cell", Apr. 1990, pp. 291-299, vol. 2, Publisher: American Society of Plant Physiologists.
Stein, D.A., et al., 'Inhibition of Dengue Virus Infections in Cell Cultures and in AG129 Mice by a Small Interfering RNA Targeting a Highly Conserved Sequence, "Journal of Virology", Oct. 2011, pp. 10154-10166, vol. 85, No. 19.
Subramanya, S., et al., "Targeted Delivery of Small Interfering RNA to Human Dendritic Cells to Suppress Dengue Virus Infection and Associated Proinflammatory Cytokine Production", "Journal of Virology", Mar. 2010, pp. 2490-2501, vol. 84, No. 5.
Jeong, J.H., et al, "siRNA Conjugate Delivery Systems", "Bioconjugate Chem.", Jan. 2009, pp. 5-14, vol. 20, No. 1.
Braasch, D., et al., "Biodistribution of phosphodiester and phosphorothioate siRNA", "Bioorganic and Medicinal Chemistry Letters", Mar. 8, 2004, pp. 1139-1143, vol. 14.
Crooke, S., "Progress in Antisense Technology", "Annu. Rev. Med.", Oct. 6, 2003, pp. 61-95, vol. 55.
Hsu, Y.-L., et al., "Lung Tumor-Associated Dendritic Cell-Derived Amphiregulin Increased Cancer Progression", "The Journal of Immunology", Jul. 8, 2011, pp. 1733-1744, vol. 187.
Kim, S., et al., "Local and systemic delivery of VEGF siRNA using polyelectrolyte complex micelles for effective treatment of cancer", "Journal of Controlled Release", Mar. 14, 2008, pp. 107-116, vol. 129, No. 2.
Medina, A., et al., "The role of stratifin in fibroblastkeratinocyte interaction", "Molecular and Cellular Biochemistry", Jul. 24, 2007, pp. 255-264, vol. 305.
Murray, C. J. L., et al., "Alternative projections of mortality and disability by cause 19902020: Global Burden of Disease Study", "The Lance", May 24, 1997, pp. 1498-1504, vol. 349.
Smith, C. J. S., et al., "Antisense RNA inhibition of polygalacturonase gene expression in transgenic tomatoes", "Letters to Nature", Aug. 25, 1988, pp. 724-726, vol. 334.
Soutschek, J., et al., "Therapeutic silencing of an endogenous gene by systemic administration of modified siRNAs", "Nature", Nov. 11, 2004, pp. 173-178, vol. 432, No. 7014.
Timmons, L., et al., "Specific interference by ingested dsRNA", "Nature", Oct. 29, 1998, p. 854 vol. 395.
Wang, X., et al., "The Role of Amphiregulin in Exemestane-Resistant Breast Cancer Cells: Evidence of an Autocrine Loop", "Cancer Research", Apr. 1, 2008, pp. 2259-2265, vol. 68, No. 7.
Xie, F., et al., "Harnessing in vivo siRNA delivery for drug discovery and therapeutic development", "Drug Discovery Today", Jan. 2006, pp. 67-73, vol. 11, No. 1/2.
Zhou, Y., et al., "Amphiregulin, An Epidermal Growth Factor Receptor Ligand, Plays an Essential Role in the Pathogenesis of Transforming Growth Factor-b-induced Pulmonary Fibrosis", "The Journal of Biological Chemistry", Dec. 7, 2012, pp. 41991-42000, vol. 287, No. 50.
Chen, P., et al., "Strand-specific 5'-O-methylation of siRNA duplexes controls guide strand selection and targeting specificity", "RNA", Dec. 19, 2007, pp. 263-274, vol. 14, No. 2.
Chemistry of Life, "Chemical Modification of siRNA and Clinical Use Thereof", "Chemistry of Life", 2005, pp. 339-342, vol. 25, No. 4.
Chemistry of Life, "Chemical Modificaton of siRNA and Clinical Use Thereof", "Chemistry of Life", 2005, vol. 25, No. 4 (English Abstract).
Fomenkov, A., et al., "RACK1 and Stratifin Target delta Np63 alpha for a Proteasome Degradation in Head and Neck Squamous Cell Carcinoma Cells upon DNA Damage", "Cell Cycle", Oct. 2004, pp. e27-e37, vol. 3, No. 10.

* cited by examiner

```
                         SEQUENCE LISTING

<160> NUMBER OF SEQ ID NOS: 343

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
ggaguaugau aaugaacca                                                        19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
caguaguagc ugucacuau                                                        19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
agacucacag cgaggauga                                                        19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
cacaaauauc cggcuauau                                                        19

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
caccauaagc gaaaugccu                                                        19

<210> SEQ ID NO 6
<211> LENGTH: 19
<212> TYPE: RNA
<213> ORGANISM: Artificial Sequence
```

```
<220> FEATURE:
<223> OTHER INFORMATION: siRNA

<400> SEQUENCE: 6
gauuacuuug gugaacggu                                              19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
caguugucac uuuuuauga                                              19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
ggaccuaucc aagauugca                                              19

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
cguuaucaca gugcaccuu                                              19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
ccuagcugag gacaaugca                                              19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
ccuagcugag gacaaugca                                              19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
cucagaggag uaugauaau                                              19
```

```
<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
cgguggacuu gagcuuucu                                                    19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
gguggugaca ugcaauugu                                                    19

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
cagggaauau gaaggagaa                                                    19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
ggaggcuucg acaagaaaa                                                    19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
ccgguggaac caaugagaa                                                    19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
ccggcuauau uauagauga                                                    19

<210> SEQ ID NO 19
<211> LENGTH: 19
<212> TYPE: RNA
<213> ORGANISM: Artificial Sequence
<220> FEATURE:
<223> OTHER INFORMATION: siRNA
```

```
<400> SEQUENCE: 19
agaauccaug cacugccaa                                              19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
caaggaccua uccaagauu                                              19

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
caaauauccg gcuauauua                                              19

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
gggacuacga cuacucaga                                              19

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
gcgaaugcag auacaucga                                              19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
gccacaccgg aaaugacau                                              19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
agaguugaac aggugauua                                              19

<210> SEQ ID NO 26
```

```
<211> LENGTH: 19
<212> TYPE: RNA
<213> ORGANISM: Artificial Sequence
<220> FEATURE:
<223> OTHER INFORMATION: siRNA

<400> SEQUENCE: 26
gaaccacaaa uauccggcu                                                    19

<210> SEQ ID NO 27
<211> LENGTH: 19
<212> TYPE: RNA
<213> ORGANISM: Artificial Sequence
<220> FEATURE:
<223> OTHER INFORMATION: siRNA

<400> SEQUENCE: 27
cauaagcgaa augccuucu                                                    19

<210> SEQ ID NO 28
<211> LENGTH: 19
<212> TYPE: RNA
<213> ORGANISM: Artificial Sequence
<220> FEATURE:
<223> OTHER INFORMATION: siRNA

<400> SEQUENCE: 28
guuuccacca uaagcgaaa                                                    19

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
caggugauua agcccaaga                                                    19

<210> SEQ ID NO 30
<211> LENGTH: 19
<212> TYPE: RNA
<213> ORGANISM: Artificial Sequence
<220> FEATURE:
<223> OTHER INFORMATION: siRNA

<400> SEQUENCE: 30
ccacaccgga aaugacauu                                                    19

<210> SEQ ID NO 31
<211> LENGTH: 19
<212> TYPE: DNA
<213> ORGANISM: Artificial Sequence
<220> FEATURE:
<223> OTHER INFORMATION: siRNA

<400> SEQUENCE: 31
gagtgaaatg ccttctagt                                                    19

<210> SEQ ID NO 32
<211> LENGTH: 19
<212> TYPE: DNA
<213> ORGANISM: Artificial Sequence
<220> FEATURE:
<223> OTHER INFORMATION: siRNA

<400> SEQUENCE: 32
```

-continued cagagttgaa caggtagtt                                                19

<210> SEQ ID NO 33
<211> LENGTH: 19
<212> TYPE: DNA
<213> ORGANISM: Artificial Sequence
<220> FEATURE:
<223> OTHER INFORMATION: siRNA

<400> SEQUENCE: 33
ctggattgga cctcaatga                                                19

<210> SEQ ID NO 34
<211> LENGTH: 19
<212> TYPE: DNA
<213> ORGANISM: Artificial Sequence
<220> FEATURE:
<223> OTHER INFORMATION: siRNA

<400> SEQUENCE: 34
gaaaactcac agcatgatt                                                19

<210> SEQ ID NO 35
<211> LENGTH: 19
<212> TYPE: DNA
<213> ORGANISM: Artificial Sequence
<220> FEATURE:
<223> OTHER INFORMATION: siRNA

<400> SEQUENCE: 35
gaaacttcga caagagaat                                                19

<210> SEQ ID NO 36
<211> LENGTH: 19
<212> TYPE: DNA
<213> ORGANISM: Artificial Sequence
<220> FEATURE:
<223> OTHER INFORMATION: siRNA

<400> SEQUENCE: 36
caggaaatat gaaggagaa                                                19

<210> SEQ ID NO 37
<211> LENGTH: 19
<212> TYPE: DNA
<213> ORGANISM: Artificial Sequence
<220> FEATURE:
<223> OTHER INFORMATION: siRNA

<400> SEQUENCE: 37
gcaaatatat agagcacct                                                19

<210> SEQ ID NO 38
<211> LENGTH: 19
<212> TYPE: DNA
<213> ORGANISM: Artificial Sequence
<220> FEATURE:
<223> OTHER INFORMATION: siRNA

<400> SEQUENCE: 38
ggtgctgtcg ctcttgata                                                19

<210> SEQ ID NO 39
<211> LENGTH: 19
<212> TYPE: DNA

```
<213> ORGANISM: Artificial Sequence
<220> FEATURE:
<223> OTHER INFORMATION: siRNA

<400> SEQUENCE: 39
tcagagttga acaggtagt                                                19

<210> SEQ ID NO 40
<211> LENGTH: 19
<212> TYPE: DNA
<213> ORGANISM: Artificial Sequence
<220> FEATURE:
<223> OTHER INFORMATION: siRNA

<400> SEQUENCE: 40
gaaagaaact tcgacaaga                                                19

<210> SEQ ID NO 41
<211> LENGTH: 19
<212> TYPE: DNA
<213> ORGANISM: Artificial Sequence
<220> FEATURE:
<223> OTHER INFORMATION: siRNA

<400> SEQUENCE: 41
gacaatacgt caggaaata                                                19

<210> SEQ ID NO 42
<211> LENGTH: 19
<212> TYPE: DNA
<213> ORGANISM: Artificial Sequence
<220> FEATURE:
<223> OTHER INFORMATION: siRNA

<400> SEQUENCE: 42
caggatatca cattggagt                                                19

<210> SEQ ID NO 43
<211> LENGTH: 19
<212> TYPE: DNA
<213> ORGANISM: Artificial Sequence
<220> FEATURE:
<223> OTHER INFORMATION: siRNA

<400> SEQUENCE: 43
ctctttccag tggatcata                                                19

<210> SEQ ID NO 44
<211> LENGTH: 19
<212> TYPE: DNA
<213> ORGANISM: Artificial Sequence
<220> FEATURE:
<223> OTHER INFORMATION: siRNA

<400> SEQUENCE: 44
cggctcaggc cattatgct                                                19

<210> SEQ ID NO 45
<211> LENGTH: 19
<212> TYPE: DNA
<213> ORGANISM: Artificial Sequence
<220> FEATURE:
<223> OTHER INFORMATION: siRNA

<400> SEQUENCE: 45
ggaccacagt gctgatgga                                                19
```

```
<210> SEQ ID NO 46
<211> LENGTH: 19
<212> TYPE: DNA
<213> ORGANISM: Artificial Sequence
<220> FEATURE:
<223> OTHER INFORMATION: siRNA

<400> SEQUENCE: 46
gctgctggat tggacctca                                              19

<210> SEQ ID NO 47
<211> LENGTH: 19
<212> TYPE: DNA
<213> ORGANISM: Artificial Sequence
<220> FEATURE:
<223> OTHER INFORMATION: siRNA

<400> SEQUENCE: 47
gttattacag tccagctta                                              19

<210> SEQ ID NO 48
<211> LENGTH: 19
<212> TYPE: DNA
<213> ORGANISM: Artificial Sequence
<220> FEATURE:
<223> OTHER INFORMATION: siRNA

<400> SEQUENCE: 48
tggacctcaa tgacaccta                                              19

<210> SEQ ID NO 49
<211> LENGTH: 19
<212> TYPE: DNA
<213> ORGANISM: Artificial Sequence
<220> FEATURE:
<223> OTHER INFORMATION: siRNA

<400> SEQUENCE: 49
ctggctatat tgtcgatga                                              19

<210> SEQ ID NO 50
<211> LENGTH: 19
<212> TYPE: DNA
<213> ORGANISM: Artificial Sequence
<220> FEATURE:
<223> OTHER INFORMATION: siRNA

<400> SEQUENCE: 50
gacggaaagt gaaaatact                                              19

<210> SEQ ID NO 51
<211> LENGTH: 19
<212> TYPE: DNA
<213> ORGANISM: Artificial Sequence
<220> FEATURE:
<223> OTHER INFORMATION: siRNA

<400> SEQUENCE: 51
gtatgataac gaaccacaa                                              19

<210> SEQ ID NO 52
<211> LENGTH: 19
<212> TYPE: DNA
<213> ORGANISM: Artificial Sequence
<220> FEATURE:
```

```
<223> OTHER INFORMATION: siRNA

<400> SEQUENCE: 52
acattggagt cactgccaa                                              19

<210> SEQ ID NO 53
<211> LENGTH: 19
<212> TYPE: DNA
<213> ORGANISM: Artificial Sequence
<220> FEATURE:
<223> OTHER INFORMATION: siRNA

<400> SEQUENCE: 53
ccaagtcata gccataaat                                              19

<210> SEQ ID NO 54
<211> LENGTH: 19
<212> TYPE: DNA
<213> ORGANISM: Artificial Sequence
<220> FEATURE:
<223> OTHER INFORMATION: siRNA

<400> SEQUENCE: 54
agtgaaatgc cttctagta                                              19

<210> SEQ ID NO 55
<211> LENGTH: 19
<212> TYPE: DNA
<213> ORGANISM: Artificial Sequence
<220> FEATURE:
<223> OTHER INFORMATION: siRNA

<400> SEQUENCE: 55
gataacgaac cacaaatac                                              19

<210> SEQ ID NO 56
<211> LENGTH: 19
<212> TYPE: DNA
<213> ORGANISM: Artificial Sequence
<220> FEATURE:
<223> OTHER INFORMATION: siRNA

<400> SEQUENCE: 56
tgcattagca gccatagct                                              19

<210> SEQ ID NO 57
<211> LENGTH: 19
<212> TYPE: DNA
<213> ORGANISM: Artificial Sequence
<220> FEATURE:
<223> OTHER INFORMATION: siRNA

<400> SEQUENCE: 57
gcattcacgg agaatgcaa                                              19

<210> SEQ ID NO 58
<211> LENGTH: 19
<212> TYPE: DNA
<213> ORGANISM: Artificial Sequence
<220> FEATURE:
<223> OTHER INFORMATION: siRNA

<400> SEQUENCE: 58
ggagtcactg ccaagtcat                                              19
```

<210> SEQ ID NO 59
<211> LENGTH: 19
<212> TYPE: DNA
<213> ORGANISM: Artificial Sequence
<220> FEATURE:
<223> OTHER INFORMATION: siRNA

<400> SEQUENCE: 59
aggtgcacga aggtaaaaa                                                19

<210> SEQ ID NO 60
<211> LENGTH: 19
<212> TYPE: DNA
<213> ORGANISM: Artificial Sequence
<220> FEATURE:
<223> OTHER INFORMATION: siRNA

<400> SEQUENCE: 60
cagcatgatt gacagtagt                                                19

<210> SEQ ID NO 61
<211> LENGTH: 19
<212> TYPE: DNA
<213> ORGANISM: Artificial Sequence
<220> FEATURE:
<223> OTHER INFORMATION: siRNA

<400> SEQUENCE: 61
cttagaagac aatacgtca                                                19

<210> SEQ ID NO 62
<211> LENGTH: 19
<212> TYPE: DNA
<213> ORGANISM: Artificial Sequence
<220> FEATURE:
<223> OTHER INFORMATION: siRNA

<400> SEQUENCE: 62
agagttgaac aggtagtta                                                19

<210> SEQ ID NO 63
<211> LENGTH: 19
<212> TYPE: DNA
<213> ORGANISM: Artificial Sequence
<220> FEATURE:
<223> OTHER INFORMATION: siRNA

<400> SEQUENCE: 63
tgatgagtcg gtcctctttt                                               19

<210> SEQ ID NO 64
<211> LENGTH: 19
<212> TYPE: DNA
<213> ORGANISM: Artificial Sequence
<220> FEATURE:
<223> OTHER INFORMATION: siRNA

<400> SEQUENCE: 64
atatatagag cacctggaa                                                19

<210> SEQ ID NO 65
<211> LENGTH: 19
<212> TYPE: DNA
<213> ORGANISM: Artificial Sequence
<220> FEATURE:
<223> OTHER INFORMATION: siRNA

```
<400> SEQUENCE: 65
gagttgaaca ggtagttaa                                              19

<210> SEQ ID NO 66
<211> LENGTH: 19
<212> TYPE: DNA
<213> ORGANISM: Artificial Sequence
<220> FEATURE:
<223> OTHER INFORMATION: siRNA

<400> SEQUENCE: 66
cattcacgga gaatgcaaa                                              19

<210> SEQ ID NO 67
<211> LENGTH: 19
<212> TYPE: DNA
<213> ORGANISM: Artificial Sequence
<220> FEATURE:
<223> OTHER INFORMATION: siRNA

<400> SEQUENCE: 67
ggaccctttt tgttatgat                                              19

<210> SEQ ID NO 68
<211> LENGTH: 19
<212> TYPE: DNA
<213> ORGANISM: Artificial Sequence
<220> FEATURE:
<223> OTHER INFORMATION: siRNA

<400> SEQUENCE: 68
cagaagagta tgataacga                                              19

<210> SEQ ID NO 69
<211> LENGTH: 19
<212> TYPE: DNA
<213> ORGANISM: Artificial Sequence
<220> FEATURE:
<223> OTHER INFORMATION: siRNA

<400> SEQUENCE: 69
ccagtggatc ataagacaa                                              19

<210> SEQ ID NO 70
<211> LENGTH: 19
<212> TYPE: DNA
<213> ORGANISM: Artificial Sequence
<220> FEATURE:
<223> OTHER INFORMATION: siRNA

<400> SEQUENCE: 70
gctgttatta cagtccagc                                              19

<210> SEQ ID NO 71
<211> LENGTH: 19
<212> TYPE: DNA
<213> ORGANISM: Artificial Sequence
<220> FEATURE:
<223> OTHER INFORMATION: siRNA

<400> SEQUENCE: 71
gggaagcgtg aaccatttt                                              19

<210> SEQ ID NO 72
<211> LENGTH: 19
```

```
<212> TYPE: DNA
<213> ORGANISM: Artificial Sequence
<220> FEATURE:
<223> OTHER INFORMATION: siRNA

<400> SEQUENCE: 72
cacagtgctg atggatttg                                                    19

<210> SEQ ID NO 73
<211> LENGTH: 19
<212> TYPE: DNA
<213> ORGANISM: Artificial Sequence
<220> FEATURE:
<223> OTHER INFORMATION: siRNA

<400> SEQUENCE: 73
agtcagagtt gaacaggta                                                    19

<210> SEQ ID NO 74
<211> LENGTH: 19
<212> TYPE: DNA
<213> ORGANISM: Artificial Sequence
<220> FEATURE:
<223> OTHER INFORMATION: siRNA

<400> SEQUENCE: 74
tggaagcagt aacatgcaa                                                    19

<210> SEQ ID NO 75
<211> LENGTH: 19
<212> TYPE: DNA
<213> ORGANISM: Artificial Sequence
<220> FEATURE:
<223> OTHER INFORMATION: siRNA

<400> SEQUENCE: 75
cacgaaggta aaaagtatt                                                    19

<210> SEQ ID NO 76
<211> LENGTH: 19
<212> TYPE: DNA
<213> ORGANISM: Artificial Sequence
<220> FEATURE:
<223> OTHER INFORMATION: siRNA

<400> SEQUENCE: 76
agaagagtat gataacgaa                                                    19

<210> SEQ ID NO 77
<211> LENGTH: 19
<212> TYPE: DNA
<213> ORGANISM: Artificial Sequence
<220> FEATURE:
<223> OTHER INFORMATION: siRNA

<400> SEQUENCE: 77
gaagcgtgaa ccattttct                                                    19

<210> SEQ ID NO 78
<211> LENGTH: 19
<212> TYPE: DNA
<213> ORGANISM: Artificial Sequence
<220> FEATURE:
<223> OTHER INFORMATION: siRNA

<400> SEQUENCE: 78
```
ggctatattg tcgatgatt                                                19

<210> SEQ ID NO 79
<211> LENGTH: 19
<212> TYPE: DNA
<213> ORGANISM: Artificial Sequence
<220> FEATURE:
<223> OTHER INFORMATION: siRNA

<400> SEQUENCE: 79
gagtcactgc caagtcata                                                19

<210> SEQ ID NO 80
<211> LENGTH: 19
<212> TYPE: DNA
<213> ORGANISM: Artificial Sequence
<220> FEATURE:
<223> OTHER INFORMATION: siRNA

<400> SEQUENCE: 80
caatggaccc ttttttgtta                                               19

<210> SEQ ID NO 81
<211> LENGTH: 19
<212> TYPE: DNA
<213> ORGANISM: Artificial Sequence
<220> FEATURE:
<223> OTHER INFORMATION: siRNA

<400> SEQUENCE: 81
gcacgaaggt aaaaagtat                                                19

<210> SEQ ID NO 82
<211> LENGTH: 19
<212> TYPE: DNA
<213> ORGANISM: Artificial Sequence
<220> FEATURE:
<223> OTHER INFORMATION: siRNA

<400> SEQUENCE: 82
tgaaatgcct tctagtagt                                                19

<210> SEQ ID NO 83
<211> LENGTH: 19
<212> TYPE: DNA
<213> ORGANISM: Artificial Sequence
<220> FEATURE:
<223> OTHER INFORMATION: siRNA

<400> SEQUENCE: 83
tggatcataa gacaatgga                                                19

<210> SEQ ID NO 84
<211> LENGTH: 19
<212> TYPE: DNA
<213> ORGANISM: Artificial Sequence
<220> FEATURE:
<223> OTHER INFORMATION: siRNA

<400> SEQUENCE: 84
gtgagtgaaa tgccttcta                                                19

<210> SEQ ID NO 85
<211> LENGTH: 19
<212> TYPE: DNA
<213> ORGANISM: Artificial Sequence

```
<220> FEATURE:
<223> OTHER INFORMATION: siRNA

<400> SEQUENCE: 85
gacctcaatg acacctact                                                    19

<210> SEQ ID NO 86
<211> LENGTH: 19
<212> TYPE: DNA
<213> ORGANISM: Artificial Sequence
<220> FEATURE:
<223> OTHER INFORMATION: siRNA

<400> SEQUENCE: 86
cctcaatgac acctactct                                                    19

<210> SEQ ID NO 87
<211> LENGTH: 19
<212> TYPE: DNA
<213> ORGANISM: Artificial Sequence
<220> FEATURE:
<223> OTHER INFORMATION: siRNA

<400> SEQUENCE: 87
gctgatggat ttgaggtta                                                    19

<210> SEQ ID NO 88
<211> LENGTH: 19
<212> TYPE: DNA
<213> ORGANISM: Artificial Sequence
<220> FEATURE:
<223> OTHER INFORMATION: siRNA

<400> SEQUENCE: 88
ggaagcagta acatgcaaa                                                    19

<210> SEQ ID NO 89
<211> LENGTH: 19
<212> TYPE: DNA
<213> ORGANISM: Artificial Sequence
<220> FEATURE:
<223> OTHER INFORMATION: siRNA

<400> SEQUENCE: 89
cagtaacatg caaatgtca                                                    19

<210> SEQ ID NO 90
<211> LENGTH: 19
<212> TYPE: DNA
<213> ORGANISM: Artificial Sequence
<220> FEATURE:
<223> OTHER INFORMATION: siRNA

<400> SEQUENCE: 90
gctatagcat aactgaaga                                                    19

<210> SEQ ID NO 91
<211> LENGTH: 19
<212> TYPE: DNA
<213> ORGANISM: Artificial Sequence
<220> FEATURE:
<223> OTHER INFORMATION: siRNA

<400> SEQUENCE: 91
ggatatcaca ttggagtca                                                    19
```

```
<210> SEQ ID NO 92
<211> LENGTH: 19
<212> TYPE: DNA
<213> ORGANISM: Artificial Sequence
<220> FEATURE:
<223> OTHER INFORMATION: siRNA

<400> SEQUENCE: 92 cccttttttgt tatgatggt                                              19

<210> SEQ ID NO 93
<211> LENGTH: 19
<212> TYPE: DNA
<213> ORGANISM: Artificial Sequence
<220> FEATURE:
<223> OTHER INFORMATION: siRNA

<400> SEQUENCE: 93
gtatataaag gtgcacgaa                                               19

<210> SEQ ID NO 94
<211> LENGTH: 19
<212> TYPE: DNA
<213> ORGANISM: Artificial Sequence
<220> FEATURE:
<223> OTHER INFORMATION: siRNA

<400> SEQUENCE: 94
ggacctcaat gacacctac                                               19

<210> SEQ ID NO 95
<211> LENGTH: 19
<212> TYPE: DNA
<213> ORGANISM: Artificial Sequence
<220> FEATURE:
<223> OTHER INFORMATION: siRNA

<400> SEQUENCE: 95
gctcttgata ctcggctca                                               19

<210> SEQ ID NO 96
<211> LENGTH: 19
<212> TYPE: DNA
<213> ORGANISM: Artificial Sequence
<220> FEATURE:
<223> OTHER INFORMATION: siRNA

<400> SEQUENCE: 96
tgctgctgga ttggacctc                                               19

<210> SEQ ID NO 97
<211> LENGTH: 19
<212> TYPE: DNA
<213> ORGANISM: Artificial Sequence
<220> FEATURE:
<223> OTHER INFORMATION: siRNA

<400> SEQUENCE: 97
gaaccacaaa tacctggct                                               19

<210> SEQ ID NO 98
<211> LENGTH: 19
<212> TYPE: DNA
<213> ORGANISM: Artificial Sequence
<220> FEATURE:
<223> OTHER INFORMATION: siRNA
```

```
<400> SEQUENCE: 98
cggtcctctt tccagtgga                                              19

<210> SEQ ID NO 99
<211> LENGTH: 19
<212> TYPE: DNA
<213> ORGANISM: Artificial Sequence
<220> FEATURE:
<223> OTHER INFORMATION: siRNA

<400> SEQUENCE: 99
ttccaacacc cgctcgttt                                              19

<210> SEQ ID NO 100
<211> LENGTH: 19
<212> TYPE: DNA
<213> ORGANISM: Artificial Sequence
<220> FEATURE:
<223> OTHER INFORMATION: siRNA

<400> SEQUENCE: 100
agagcacctg gaagcagta                                              19

<210> SEQ ID NO 101
<211> LENGTH: 19
<212> TYPE: DNA
<213> ORGANISM: Artificial Sequence
<220> FEATURE:
<223> OTHER INFORMATION: siRNA

<400> SEQUENCE: 101
tctttccagt ggatcataa                                              19

<210> SEQ ID NO 102
<211> LENGTH: 19
<212> TYPE: DNA
<213> ORGANISM: Artificial Sequence
<220> FEATURE:
<223> OTHER INFORMATION: siRNA

<400> SEQUENCE: 102
cctttttgtt atgatggtt                                              19

<210> SEQ ID NO 103
<211> LENGTH: 19
<212> TYPE: DNA
<213> ORGANISM: Artificial Sequence
<220> FEATURE:
<223> OTHER INFORMATION: siRNA

<400> SEQUENCE: 103
cacctggaag cagtaacat                                              19

<210> SEQ ID NO 104
<211> LENGTH: 19
<212> TYPE: DNA
<213> ORGANISM: Artificial Sequence
<220> FEATURE:
<223> OTHER INFORMATION: siRNA

<400> SEQUENCE: 104
ctgaggaacg aaagaaact                                              19

<210> SEQ ID NO 105
```

```
<211> LENGTH: 19
<212> TYPE: DNA
<213> ORGANISM: Artificial Sequence
<220> FEATURE:
<223> OTHER INFORMATION: siRNA

<400> SEQUENCE: 105
gtgaaatgcc ttctagtag                                                   19

<210> SEQ ID NO 106
<211> LENGTH: 19
<212> TYPE: DNA
<213> ORGANISM: Artificial Sequence
<220> FEATURE:
<223> OTHER INFORMATION: siRNA

<400> SEQUENCE: 106
ctactctggg aagcgtgaa                                                   19

<210> SEQ ID NO 107
<211> LENGTH: 19
<212> TYPE: DNA
<213> ORGANISM: Artificial Sequence
<220> FEATURE:
<223> OTHER INFORMATION: siRNA

<400> SEQUENCE: 107
ctgggaagcg tgaaccatt                                                   19

<210> SEQ ID NO 108
<211> LENGTH: 19
<212> TYPE: DNA
<213> ORGANISM: Artificial Sequence
<220> FEATURE:
<223> OTHER INFORMATION: siRNA

<400> SEQUENCE: 108
actactcaga agagtatga                                                   19

<210> SEQ ID NO 109
<211> LENGTH: 19
<212> TYPE: DNA
<213> ORGANISM: Artificial Sequence
<220> FEATURE:
<223> OTHER INFORMATION: siRNA

<400> SEQUENCE: 109
catgcaaatg tcagcaaga                                                   19

<210> SEQ ID NO 110
<211> LENGTH: 19
<212> TYPE: DNA
<213> ORGANISM: Artificial Sequence
<220> FEATURE:
<223> OTHER INFORMATION: siRNA

<400> SEQUENCE: 110
tgaggttacc tcaagaagt                                                   19

<210> SEQ ID NO 111
<211> LENGTH: 19
<212> TYPE: DNA
<213> ORGANISM: Artificial Sequence
<220> FEATURE:
<223> OTHER INFORMATION: siRNA

<400> SEQUENCE: 111
```
actcggctca ggccattat                                              19

<210> SEQ ID NO 112
<211> LENGTH: 19
<212> TYPE: DNA
<213> ORGANISM: Artificial Sequence
<220> FEATURE:
<223> OTHER INFORMATION: siRNA

<400> SEQUENCE: 112
ttcacggaga atgcaaata                                              19

<210> SEQ ID NO 113
<211> LENGTH: 19
<212> TYPE: DNA
<213> ORGANISM: Artificial Sequence
<220> FEATURE:
<223> OTHER INFORMATION: siRNA

<400> SEQUENCE: 113
ctgctggatt ggacctcaa                                              19

<210> SEQ ID NO 114
<211> LENGTH: 19
<212> TYPE: DNA
<213> ORGANISM: Artificial Sequence
<220> FEATURE:
<223> OTHER INFORMATION: siRNA

<400> SEQUENCE: 114
tgattcagtc agagttgaa                                              19

<210> SEQ ID NO 115
<211> LENGTH: 19
<212> TYPE: DNA
<213> ORGANISM: Artificial Sequence
<220> FEATURE:
<223> OTHER INFORMATION: siRNA

<400> SEQUENCE: 115
tgccaagtca tagccataa                                              19

<210> SEQ ID NO 116
<211> LENGTH: 19
<212> TYPE: DNA
<213> ORGANISM: Artificial Sequence
<220> FEATURE:
<223> OTHER INFORMATION: siRNA

<400> SEQUENCE: 116
ctcaagaagt gagatgtct                                              19

<210> SEQ ID NO 117
<211> LENGTH: 19
<212> TYPE: DNA
<213> ORGANISM: Artificial Sequence
<220> FEATURE:
<223> OTHER INFORMATION: siRNA

<400> SEQUENCE: 117
gccaagtcat agccataaa                                              19

<210> SEQ ID NO 118
<211> LENGTH: 19
<212> TYPE: DNA

```
<213> ORGANISM: Artificial Sequence
<220> FEATURE:
<223> OTHER INFORMATION: siRNA

<400> SEQUENCE: 118
ctcagaagag tatgataac                                                    19

<210> SEQ ID NO 119
<211> LENGTH: 19
<212> TYPE: DNA
<213> ORGANISM: Artificial Sequence
<220> FEATURE:
<223> OTHER INFORMATION: siRNA

<400> SEQUENCE: 119
ttctgcattc acggagaat                                                    19

<210> SEQ ID NO 120
<211> LENGTH: 19
<212> TYPE: DNA
<213> ORGANISM: Artificial Sequence
<220> FEATURE:
<223> OTHER INFORMATION: siRNA

<400> SEQUENCE: 120
taagacaatg gacccttt                                                     19

<210> SEQ ID NO 121
<211> LENGTH: 19
<212> TYPE: DNA
<213> ORGANISM: Artificial Sequence
<220> FEATURE:
<223> OTHER INFORMATION: siRNA

<400> SEQUENCE: 121
aggttacctc aagaagtga                                                    19

<210> SEQ ID NO 122
<211> LENGTH: 19
<212> TYPE: DNA
<213> ORGANISM: Artificial Sequence
<220> FEATURE:
<223> OTHER INFORMATION: siRNA

<400> SEQUENCE: 122
aatgccttct agtagtgaa                                                    19

<210> SEQ ID NO 123
<211> LENGTH: 19
<212> TYPE: DNA
<213> ORGANISM: Artificial Sequence
<220> FEATURE:
<223> OTHER INFORMATION: siRNA

<400> SEQUENCE: 123
atgattcagt cagagttga                                                    19

<210> SEQ ID NO 124
<211> LENGTH: 19
<212> TYPE: DNA
<213> ORGANISM: Artificial Sequence
<220> FEATURE:
<223> OTHER INFORMATION: siRNA

<400> SEQUENCE: 124
aaacaagacg gaaagtgaa                                                    19
```

<210> SEQ ID NO 125
<211> LENGTH: 19
<212> TYPE: DNA
<213> ORGANISM: Artificial Sequence
<220> FEATURE:
<223> OTHER INFORMATION: siRNA

<400> SEQUENCE: 125
tttctgcatt cacggagaa                                              19

<210> SEQ ID NO 126
<211> LENGTH: 19
<212> TYPE: DNA
<213> ORGANISM: Artificial Sequence
<220> FEATURE:
<223> OTHER INFORMATION: siRNA

<400> SEQUENCE: 126
caaatacctg gctatattg                                              19

<210> SEQ ID NO 127
<211> LENGTH: 19
<212> TYPE: DNA
<213> ORGANISM: Artificial Sequence
<220> FEATURE:
<223> OTHER INFORMATION: siRNA

<400> SEQUENCE: 127
tcttccaaca cccgctcgt                                              19

<210> SEQ ID NO 128
<211> LENGTH: 19
<212> TYPE: DNA
<213> ORGANISM: Artificial Sequence
<220> FEATURE:
<223> OTHER INFORMATION: siRNA

<400> SEQUENCE: 128
gaagcagtaa catgcaaat                                              19

<210> SEQ ID NO 129
<211> LENGTH: 19
<212> TYPE: DNA
<213> ORGANISM: Artificial Sequence
<220> FEATURE:
<223> OTHER INFORMATION: siRNA

<400> SEQUENCE: 129
gatgattcag tcagagttg                                              19

<210> SEQ ID NO 130
<211> LENGTH: 19
<212> TYPE: DNA
<213> ORGANISM: Artificial Sequence
<220> FEATURE:
<223> OTHER INFORMATION: siRNA

<400> SEQUENCE: 130
tgcattcacg gagaatgca                                              19

<210> SEQ ID NO 131
<211> LENGTH: 19
<212> TYPE: DNA
<213> ORGANISM: Artificial Sequence
<220> FEATURE:

```
<223> OTHER INFORMATION: siRNA

<400> SEQUENCE: 131
ctcagtgagg actcctaca                                                    19

<210> SEQ ID NO 132
<211> LENGTH: 19
<212> TYPE: DNA
<213> ORGANISM: Artificial Sequence
<220> FEATURE:
<223> OTHER INFORMATION: siRNA

<400> SEQUENCE: 132
cactacgaga tagccaaca                                                    19

<210> SEQ ID NO 133
<211> LENGTH: 19
<212> TYPE: DNA
<213> ORGANISM: Artificial Sequence
<220> FEATURE:
<223> OTHER INFORMATION: siRNA

<400> SEQUENCE: 133
cagtcttcca ctacgagat                                                    19

<210> SEQ ID NO 134
<211> LENGTH: 19
<212> TYPE: DNA
<213> ORGANISM: Artificial Sequence
<220> FEATURE:
<223> OTHER INFORMATION: siRNA

<400> SEQUENCE: 134
agctcctgag agacaacct                                                    19

<210> SEQ ID NO 135
<211> LENGTH: 19
<212> TYPE: DNA
<213> ORGANISM: Artificial Sequence
<220> FEATURE:
<223> OTHER INFORMATION: siRNA

<400> SEQUENCE: 135
tcagtcttcc actacgaga                                                    19

<210> SEQ ID NO 136
<211> LENGTH: 19
<212> TYPE: DNA
<213> ORGANISM: Artificial Sequence
<220> FEATURE:
<223> OTHER INFORMATION: siRNA

<400> SEQUENCE: 136
agagacaacc tgacgctgt                                                    19

<210> SEQ ID NO 137
<211> LENGTH: 19
<212> TYPE: DNA
<213> ORGANISM: Artificial Sequence
<220> FEATURE:
<223> OTHER INFORMATION: siRNA

<400> SEQUENCE: 137
ccgaacggta tgaagacat                                                    19
```

```
<210> SEQ ID NO 138
<211> LENGTH: 19
<212> TYPE: DNA
<213> ORGANISM: Artificial Sequence
<220> FEATURE:
<223> OTHER INFORMATION: siRNA

<400> SEQUENCE: 138
ctgaacaggc cgaacggta                                            19

<210> SEQ ID NO 139
<211> LENGTH: 19
<212> TYPE: DNA
<213> ORGANISM: Artificial Sequence
<220> FEATURE:
<223> OTHER INFORMATION: siRNA

<400> SEQUENCE: 139
ctcctgagag acaacctga                                            19

<210> SEQ ID NO 140
<211> LENGTH: 19
<212> TYPE: DNA
<213> ORGANISM: Artificial Sequence
<220> FEATURE:
<223> OTHER INFORMATION: siRNA

<400> SEQUENCE: 140
gacatggcag ctttcatga                                            19

<210> SEQ ID NO 141
<211> LENGTH: 19
<212> TYPE: DNA
<213> ORGANISM: Artificial Sequence
<220> FEATURE:
<223> OTHER INFORMATION: siRNA

<400> SEQUENCE: 141
cgaacggtat gaagacatg                                            19

<210> SEQ ID NO 142
<211> LENGTH: 19
<212> TYPE: DNA
<213> ORGANISM: Artificial Sequence
<220> FEATURE:
<223> OTHER INFORMATION: siRNA

<400> SEQUENCE: 142
agtaccggga gaaggtaga                                            19

<210> SEQ ID NO 143
<211> LENGTH: 19
<212> TYPE: DNA
<213> ORGANISM: Artificial Sequence
<220> FEATURE:
<223> OTHER INFORMATION: siRNA

<400> SEQUENCE: 143
acttttcagt cttccacta                                            19

<210> SEQ ID NO 144
<211> LENGTH: 19
<212> TYPE: DNA
<213> ORGANISM: Artificial Sequence
<220> FEATURE:
<223> OTHER INFORMATION: siRNA
```

<400> SEQUENCE: 144
gcatcgagca gaagagcaa                                                    19

<210> SEQ ID NO 145
<211> LENGTH: 19
<212> TYPE: DNA
<213> ORGANISM: Artificial Sequence
<220> FEATURE:
<223> OTHER INFORMATION: siRNA

<400> SEQUENCE: 145
gcgaaacctg ctttccgta                                                    19

<210> SEQ ID NO 146
<211> LENGTH: 19
<212> TYPE: DNA
<213> ORGANISM: Artificial Sequence
<220> FEATURE:
<223> OTHER INFORMATION: siRNA

<400> SEQUENCE: 146
gtgaaagagt accgggaga                                                    19

<210> SEQ ID NO 147
<211> LENGTH: 19
<212> TYPE: DNA
<213> ORGANISM: Artificial Sequence
<220> FEATURE:
<223> OTHER INFORMATION: siRNA

<400> SEQUENCE: 147
gcgatgacaa gaagcgcat                                                    19

<210> SEQ ID NO 148
<211> LENGTH: 19
<212> TYPE: DNA
<213> ORGANISM: Artificial Sequence
<220> FEATURE:
<223> OTHER INFORMATION: siRNA

<400> SEQUENCE: 148
agtcttccac tacgagata                                                    19

<210> SEQ ID NO 149
<211> LENGTH: 19
<212> TYPE: DNA
<213> ORGANISM: Artificial Sequence
<220> FEATURE:
<223> OTHER INFORMATION: siRNA

<400> SEQUENCE: 149
tcagtgagga ctcctacaa                                                    19

<210> SEQ ID NO 150
<211> LENGTH: 19
<212> TYPE: DNA
<213> ORGANISM: Artificial Sequence
<220> FEATURE:
<223> OTHER INFORMATION: siRNA

<400> SEQUENCE: 150
ggtagagacc gagctcaga                                                    19

<210> SEQ ID NO 151
<211> LENGTH: 19

```
<212> TYPE: DNA
<213> ORGANISM: Artificial Sequence
<220> FEATURE:
<223> OTHER INFORMATION: siRNA

<400> SEQUENCE: 151
ccgaggtgaa agagtaccg                                              19

<210> SEQ ID NO 152
<211> LENGTH: 19
<212> TYPE: DNA
<213> ORGANISM: Artificial Sequence
<220> FEATURE:
<223> OTHER INFORMATION: siRNA

<400> SEQUENCE: 152
caggccgaac ggtatgaag                                              19

<210> SEQ ID NO 153
<211> LENGTH: 19
<212> TYPE: DNA
<213> ORGANISM: Artificial Sequence
<220> FEATURE:
<223> OTHER INFORMATION: siRNA

<400> SEQUENCE: 153
cggtatgaag acatggcag                                              19

<210> SEQ ID NO 154
<211> LENGTH: 19
<212> TYPE: DNA
<213> ORGANISM: Artificial Sequence
<220> FEATURE:
<223> OTHER INFORMATION: siRNA

<400> SEQUENCE: 154
tgctggactc gcacctcat                                              19

<210> SEQ ID NO 155
<211> LENGTH: 19
<212> TYPE: DNA
<213> ORGANISM: Artificial Sequence
<220> FEATURE:
<223> OTHER INFORMATION: siRNA

<400> SEQUENCE: 155
aagaagcgca tcatcgatt                                              19

<210> SEQ ID NO 156
<211> LENGTH: 19
<212> TYPE: DNA
<213> ORGANISM: Artificial Sequence
<220> FEATURE:
<223> OTHER INFORMATION: siRNA

<400> SEQUENCE: 156
ctggactcgc acctcatca                                              19

<210> SEQ ID NO 157
<211> LENGTH: 19
<212> TYPE: DNA
<213> ORGANISM: Artificial Sequence
<220> FEATURE:
<223> OTHER INFORMATION: siRNA

<400> SEQUENCE: 157
```
ggactcgcac ctcatcaaa                                                19

<210> SEQ ID NO 158
<211> LENGTH: 19
<212> TYPE: DNA
<213> ORGANISM: Artificial Sequence
<220> FEATURE:
<223> OTHER INFORMATION: siRNA

<400> SEQUENCE: 158
gaagcgcatc atcgattct                                                19

<210> SEQ ID NO 159
<211> LENGTH: 19
<212> TYPE: DNA
<213> ORGANISM: Artificial Sequence
<220> FEATURE:
<223> OTHER INFORMATION: siRNA

<400> SEQUENCE: 159
gtcttccact acgagatag                                                19

<210> SEQ ID NO 160
<211> LENGTH: 19
<212> TYPE: DNA
<213> ORGANISM: Artificial Sequence
<220> FEATURE:
<223> OTHER INFORMATION: siRNA

<400> SEQUENCE: 160
aaggtagaga ccgagctca                                                19

<210> SEQ ID NO 161
<211> LENGTH: 19
<212> TYPE: DNA
<213> ORGANISM: Artificial Sequence
<220> FEATURE:
<223> OTHER INFORMATION: siRNA

<400> SEQUENCE: 161
agcgaaacct gctttccgt                                                19

<210> SEQ ID NO 162
<211> LENGTH: 19
<212> TYPE: DNA
<213> ORGANISM: Artificial Sequence
<220> FEATURE:
<223> OTHER INFORMATION: siRNA

<400> SEQUENCE: 162
gactactacc gctacctag                                                19

<210> SEQ ID NO 163
<211> LENGTH: 19
<212> TYPE: DNA
<213> ORGANISM: Artificial Sequence
<220> FEATURE:
<223> OTHER INFORMATION: siRNA

<400> SEQUENCE: 163
cagagagccg cgtcttcta                                                19

<210> SEQ ID NO 164
<211> LENGTH: 19
<212> TYPE: DNA
<213> ORGANISM: Artificial Sequence

```
<220> FEATURE:
<223> OTHER INFORMATION: siRNA

<400> SEQUENCE: 164
gatgacaaga agcgcatca                                                  19

<210> SEQ ID NO 165
<211> LENGTH: 19
<212> TYPE: DNA
<213> ORGANISM: Artificial Sequence
<220> FEATURE:
<223> OTHER INFORMATION: siRNA

<400> SEQUENCE: 165
catcgagcag aagagcaac                                                  19

<210> SEQ ID NO 166
<211> LENGTH: 19
<212> TYPE: DNA
<213> ORGANISM: Artificial Sequence
<220> FEATURE:
<223> OTHER INFORMATION: siRNA

<400> SEQUENCE: 166
tgcagctcct gagagacaa                                                  19

<210> SEQ ID NO 167
<211> LENGTH: 19
<212> TYPE: DNA
<213> ORGANISM: Artificial Sequence
<220> FEATURE:
<223> OTHER INFORMATION: siRNA

<400> SEQUENCE: 167
acggtatgaa gacatggca                                                  19

<210> SEQ ID NO 168
<211> LENGTH: 19
<212> TYPE: DNA
<213> ORGANISM: Artificial Sequence
<220> FEATURE:
<223> OTHER INFORMATION: siRNA

<400> SEQUENCE: 168
tggactcgca cctcatcaa                                                  19

<210> SEQ ID NO 169
<211> LENGTH: 19
<212> TYPE: DNA
<213> ORGANISM: Artificial Sequence
<220> FEATURE:
<223> OTHER INFORMATION: siRNA

<400> SEQUENCE: 169
ggcgatgaca agaagcgca                                                  19

<210> SEQ ID NO 170
<211> LENGTH: 19
<212> TYPE: DNA
<213> ORGANISM: Artificial Sequence
<220> FEATURE:
<223> OTHER INFORMATION: siRNA

<400> SEQUENCE: 170
tgaacaggcc gaacggtat                                                  19
```

<210> SEQ ID NO 171
<211> LENGTH: 19
<212> TYPE: DNA
<213> ORGANISM: Artificial Sequence
<220> FEATURE:
<223> OTHER INFORMATION: siRNA

<400> SEQUENCE: 171
aggccgaacg gtatgaaga                                                19

<210> SEQ ID NO 172
<211> LENGTH: 19
<212> TYPE: DNA
<213> ORGANISM: Artificial Sequence
<220> FEATURE:
<223> OTHER INFORMATION: siRNA

<400> SEQUENCE: 172
tcgagcagaa gagcaacga                                                19

<210> SEQ ID NO 173
<211> LENGTH: 19
<212> TYPE: DNA
<213> ORGANISM: Artificial Sequence
<220> FEATURE:
<223> OTHER INFORMATION: siRNA

<400> SEQUENCE: 173
tccactacga gatagccaa                                                19

<210> SEQ ID NO 174
<211> LENGTH: 19
<212> TYPE: DNA
<213> ORGANISM: Artificial Sequence
<220> FEATURE:
<223> OTHER INFORMATION: siRNA

<400> SEQUENCE: 174
ggtgaaagag taccgggag                                                19

<210> SEQ ID NO 175
<211> LENGTH: 19
<212> TYPE: DNA
<213> ORGANISM: Artificial Sequence
<220> FEATURE:
<223> OTHER INFORMATION: siRNA

<400> SEQUENCE: 175
gccgaacggt atgaagaca                                                19

<210> SEQ ID NO 176
<211> LENGTH: 19
<212> TYPE: DNA
<213> ORGANISM: Artificial Sequence
<220> FEATURE:
<223> OTHER INFORMATION: siRNA

<400> SEQUENCE: 176
aggagatgcc gcctaccaa                                                19

<210> SEQ ID NO 177
<211> LENGTH: 19
<212> TYPE: DNA
<213> ORGANISM: Artificial Sequence
<220> FEATURE:
<223> OTHER INFORMATION: siRNA

<400> SEQUENCE: 177
ggagcgaaac ctgctttcc                                                  19

<210> SEQ ID NO 178
<211> LENGTH: 19
<212> TYPE: DNA
<213> ORGANISM: Artificial Sequence
<220> FEATURE:
<223> OTHER INFORMATION: siRNA

<400> SEQUENCE: 178
cagtgaggac tcctacaag                                                  19

<210> SEQ ID NO 179
<211> LENGTH: 19
<212> TYPE: DNA
<213> ORGANISM: Artificial Sequence
<220> FEATURE:
<223> OTHER INFORMATION: siRNA

<400> SEQUENCE: 179
agcgcatcat cgattctgc                                                  19

<210> SEQ ID NO 180
<211> LENGTH: 19
<212> TYPE: DNA
<213> ORGANISM: Artificial Sequence
<220> FEATURE:
<223> OTHER INFORMATION: siRNA

<400> SEQUENCE: 180
catcatgcag ctcctgaga                                                  19

<210> SEQ ID NO 181
<211> LENGTH: 19
<212> TYPE: DNA
<213> ORGANISM: Artificial Sequence
<220> FEATURE:
<223> OTHER INFORMATION: siRNA

<400> SEQUENCE: 181
gccgcgtctt ctacctgaa                                                  19

<210> SEQ ID NO 182
<211> LENGTH: 19
<212> TYPE: DNA
<213> ORGANISM: Artificial Sequence
<220> FEATURE:
<223> OTHER INFORMATION: siRNA

<400> SEQUENCE: 182
gagacaacct gacgctgtg                                                  19

<210> SEQ ID NO 183
<211> LENGTH: 19
<212> TYPE: DNA
<213> ORGANISM: Artificial Sequence
<220> FEATURE:
<223> OTHER INFORMATION: siRNA

<400> SEQUENCE: 183
cgatgacaag aagcgcatc                                                  19

<210> SEQ ID NO 184

```
<210> SEQ ID NO 184
<211> LENGTH: 19
<212> TYPE: DNA
<213> ORGANISM: Artificial Sequence
<220> FEATURE:
<223> OTHER INFORMATION: siRNA

<400> SEQUENCE: 184
cttccactac gagatagcc                                                19

<210> SEQ ID NO 185
<211> LENGTH: 19
<212> TYPE: DNA
<213> ORGANISM: Artificial Sequence
<220> FEATURE:
<223> OTHER INFORMATION: siRNA

<400> SEQUENCE: 185
ccactacgag atagccaac                                                19

<210> SEQ ID NO 186
<211> LENGTH: 19
<212> TYPE: DNA
<213> ORGANISM: Artificial Sequence
<220> FEATURE:
<223> OTHER INFORMATION: siRNA

<400> SEQUENCE: 186
gctcctgaga gacaacctg                                                19

<210> SEQ ID NO 187
<211> LENGTH: 19
<212> TYPE: DNA
<213> ORGANISM: Artificial Sequence
<220> FEATURE:
<223> OTHER INFORMATION: siRNA

<400> SEQUENCE: 187
atcatcgatt ctgcccggt                                                19

<210> SEQ ID NO 188
<211> LENGTH: 19
<212> TYPE: DNA
<213> ORGANISM: Artificial Sequence
<220> FEATURE:
<223> OTHER INFORMATION: siRNA

<400> SEQUENCE: 188
tgagagacaa cctgacgct                                                19

<210> SEQ ID NO 189
<211> LENGTH: 19
<212> TYPE: DNA
<213> ORGANISM: Artificial Sequence
<220> FEATURE:
<223> OTHER INFORMATION: siRNA

<400> SEQUENCE: 189
agacatggca gctttcatg                                                19

<210> SEQ ID NO 190
<211> LENGTH: 19
<212> TYPE: DNA
<213> ORGANISM: Artificial Sequence
<220> FEATURE:
<223> OTHER INFORMATION: siRNA

<400> SEQUENCE: 190
```
tcttccacta cgagatagc        19

<210> SEQ ID NO 191
<211> LENGTH: 19
<212> TYPE: DNA
<213> ORGANISM: Artificial Sequence
<220> FEATURE:
<223> OTHER INFORMATION: siRNA

<400> SEQUENCE: 191
gaacaggccg aacggtatg        19

<210> SEQ ID NO 192
<211> LENGTH: 19
<212> TYPE: DNA
<213> ORGANISM: Artificial Sequence
<220> FEATURE:
<223> OTHER INFORMATION: siRNA

<400> SEQUENCE: 192
atgcagctcc tgagagaca        19

<210> SEQ ID NO 193
<211> LENGTH: 19
<212> TYPE: DNA
<213> ORGANISM: Artificial Sequence
<220> FEATURE:
<223> OTHER INFORMATION: siRNA

<400> SEQUENCE: 193
accgagctca gaggtgtgt        19

<210> SEQ ID NO 194
<211> LENGTH: 19
<212> TYPE: DNA
<213> ORGANISM: Artificial Sequence
<220> FEATURE:
<223> OTHER INFORMATION: siRNA

<400> SEQUENCE: 194
cctgagagac aacctgacg        19

<210> SEQ ID NO 195
<211> LENGTH: 19
<212> TYPE: DNA
<213> ORGANISM: Artificial Sequence
<220> FEATURE:
<223> OTHER INFORMATION: siRNA

<400> SEQUENCE: 195
cacaccctca gtgaggact        19

<210> SEQ ID NO 196
<211> LENGTH: 19
<212> TYPE: DNA
<213> ORGANISM: Artificial Sequence
<220> FEATURE:
<223> OTHER INFORMATION: siRNA

<400> SEQUENCE: 196
ttccactacg agatagcca        19

<210> SEQ ID NO 197
<211> LENGTH: 19
<212> TYPE: DNA

```
<213> ORGANISM: Artificial Sequence
<220> FEATURE:
<223> OTHER INFORMATION: siRNA

<400> SEQUENCE: 197
acatggcagc tttcatgaa                                                19

<210> SEQ ID NO 198
<211> LENGTH: 19
<212> TYPE: DNA
<213> ORGANISM: Artificial Sequence
<220> FEATURE:
<223> OTHER INFORMATION: siRNA

<400> SEQUENCE: 198
tgacaagaag cgcatcatc                                                19

<210> SEQ ID NO 199
<211> LENGTH: 19
<212> TYPE: DNA
<213> ORGANISM: Artificial Sequence
<220> FEATURE:
<223> OTHER INFORMATION: siRNA

<400> SEQUENCE: 199
aaggagatgc cgcctacca                                                19

<210> SEQ ID NO 200
<211> LENGTH: 19
<212> TYPE: DNA
<213> ORGANISM: Artificial Sequence
<220> FEATURE:
<223> OTHER INFORMATION: siRNA

<400> SEQUENCE: 200
cttttcagtc ttccactac                                                19

<210> SEQ ID NO 201
<211> LENGTH: 19
<212> TYPE: DNA
<213> ORGANISM: Artificial Sequence
<220> FEATURE:
<223> OTHER INFORMATION: siRNA

<400> SEQUENCE: 201
tcctgagaga caacctgac                                                19

<210> SEQ ID NO 202
<211> LENGTH: 19
<212> TYPE: DNA
<213> ORGANISM: Artificial Sequence
<220> FEATURE:
<223> OTHER INFORMATION: siRNA

<400> SEQUENCE: 202
gcagctcctg agagacaac                                                19

<210> SEQ ID NO 203
<211> LENGTH: 19
<212> TYPE: DNA
<213> ORGANISM: Artificial Sequence
<220> FEATURE:
<223> OTHER INFORMATION: siRNA

<400> SEQUENCE: 203
agccgcgtct tctacctga                                                19
```

<210> SEQ ID NO 204
<211> LENGTH: 19
<212> TYPE: DNA
<213> ORGANISM: Artificial Sequence
<220> FEATURE:
<223> OTHER INFORMATION: siRNA

<400> SEQUENCE: 204
attctgcccg gtcagccta                                              19

<210> SEQ ID NO 205
<211> LENGTH: 19
<212> TYPE: DNA
<213> ORGANISM: Artificial Sequence
<220> FEATURE:
<223> OTHER INFORMATION: siRNA

<400> SEQUENCE: 205
actcgcacct catcaaagg                                              19

<210> SEQ ID NO 206
<211> LENGTH: 19
<212> TYPE: DNA
<213> ORGANISM: Artificial Sequence
<220> FEATURE:
<223> OTHER INFORMATION: siRNA

<400> SEQUENCE: 206
agaccgagct cagaggtgt                                              19

<210> SEQ ID NO 207
<211> LENGTH: 19
<212> TYPE: DNA
<213> ORGANISM: Artificial Sequence
<220> FEATURE:
<223> OTHER INFORMATION: siRNA

<400> SEQUENCE: 207
gactcgcacc tcatcaaag                                              19

<210> SEQ ID NO 208
<211> LENGTH: 19
<212> TYPE: DNA
<213> ORGANISM: Artificial Sequence
<220> FEATURE:
<223> OTHER INFORMATION: siRNA

<400> SEQUENCE: 208
agaagcgcat catcgattc                                              19

<210> SEQ ID NO 209
<211> LENGTH: 19
<212> TYPE: DNA
<213> ORGANISM: Artificial Sequence
<220> FEATURE:
<223> OTHER INFORMATION: siRNA

<400> SEQUENCE: 209
gggtgactac taccgctac                                              19

<210> SEQ ID NO 210
<211> LENGTH: 19
<212> TYPE: DNA
<213> ORGANISM: Artificial Sequence
<220> FEATURE:

<223> OTHER INFORMATION: siRNA

<400> SEQUENCE: 210
caagaccacc ttcgacgag                                                19

<210> SEQ ID NO 211
<211> LENGTH: 19
<212> TYPE: DNA
<213> ORGANISM: Artificial Sequence
<220> FEATURE:
<223> OTHER INFORMATION: siRNA

<400> SEQUENCE: 211
ctacgagata gccaacagc                                                19

<210> SEQ ID NO 212
<211> LENGTH: 19
<212> TYPE: DNA
<213> ORGANISM: Artificial Sequence
<220> FEATURE:
<223> OTHER INFORMATION: siRNA

<400> SEQUENCE: 212
tttcagtctt ccactacga                                                19

<210> SEQ ID NO 213
<211> LENGTH: 19
<212> TYPE: DNA
<213> ORGANISM: Artificial Sequence
<220> FEATURE:
<223> OTHER INFORMATION: siRNA

<400> SEQUENCE: 213
aggtgaaaga gtaccggga                                                19

<210> SEQ ID NO 214
<211> LENGTH: 19
<212> TYPE: DNA
<213> ORGANISM: Artificial Sequence
<220> FEATURE:
<223> OTHER INFORMATION: siRNA

<400> SEQUENCE: 214
aagcgcatca tcgattctg                                                19

<210> SEQ ID NO 215
<211> LENGTH: 19
<212> TYPE: DNA
<213> ORGANISM: Artificial Sequence
<220> FEATURE:
<223> OTHER INFORMATION: siRNA

<400> SEQUENCE: 215
gcatcatcga ttctgcccg                                                19

<210> SEQ ID NO 216
<211> LENGTH: 19
<212> TYPE: DNA
<213> ORGANISM: Artificial Sequence
<220> FEATURE:
<223> OTHER INFORMATION: siRNA

<400> SEQUENCE: 216
aacggtatga agacatggc                                                19

```
<210> SEQ ID NO 217
<211> LENGTH: 19
<212> TYPE: DNA
<213> ORGANISM: Artificial Sequence
<220> FEATURE:
<223> OTHER INFORMATION: siRNA

<400> SEQUENCE: 217
atcgagcaga agagcaacg                                                  19

<210> SEQ ID NO 218
<211> LENGTH: 19
<212> TYPE: DNA
<213> ORGANISM: Artificial Sequence
<220> FEATURE:
<223> OTHER INFORMATION: siRNA

<400> SEQUENCE: 218
actactaccg ctacctagc                                                  19

<210> SEQ ID NO 219
<211> LENGTH: 19
<212> TYPE: DNA
<213> ORGANISM: Artificial Sequence
<220> FEATURE:
<223> OTHER INFORMATION: siRNA

<400> SEQUENCE: 219
ttttcagtct tccactacg                                                  19

<210> SEQ ID NO 220
<211> LENGTH: 19
<212> TYPE: DNA
<213> ORGANISM: Artificial Sequence
<220> FEATURE:
<223> OTHER INFORMATION: siRNA

<400> SEQUENCE: 220
acgagatagc caacagccc                                                  19

<210> SEQ ID NO 221
<211> LENGTH: 19
<212> TYPE: DNA
<213> ORGANISM: Artificial Sequence
<220> FEATURE:
<223> OTHER INFORMATION: siRNA

<400> SEQUENCE: 221
actaccgcta cctagccga                                                  19

<210> SEQ ID NO 222
<211> LENGTH: 19
<212> TYPE: DNA
<213> ORGANISM: Artificial Sequence
<220> FEATURE:
<223> OTHER INFORMATION: siRNA

<400> SEQUENCE: 222
actacgagat agccaacag                                                  19

<210> SEQ ID NO 223
<211> LENGTH: 19
<212> TYPE: DNA
<213> ORGANISM: Artificial Sequence
<220> FEATURE:
<223> OTHER INFORMATION: siRNA
```

```
<400> SEQUENCE: 223
cccgaggtga aagagtacc                                                    19

<210> SEQ ID NO 224
<211> LENGTH: 19
<212> TYPE: DNA
<213> ORGANISM: Artificial Sequence
<220> FEATURE:
<223> OTHER INFORMATION: siRNA

<400> SEQUENCE: 224
cagctcctga gagacaacc                                                    19

<210> SEQ ID NO 225
<211> LENGTH: 19
<212> TYPE: DNA
<213> ORGANISM: Artificial Sequence
<220> FEATURE:
<223> OTHER INFORMATION: siRNA

<400> SEQUENCE: 225
catcgattct gcccggtca                                                    19

<210> SEQ ID NO 226
<211> LENGTH: 19
<212> TYPE: DNA
<213> ORGANISM: Artificial Sequence
<220> FEATURE:
<223> OTHER INFORMATION: siRNA

<400> SEQUENCE: 226
gagagacaac ctgacgctg                                                    19

<210> SEQ ID NO 227
<211> LENGTH: 19
<212> TYPE: DNA
<213> ORGANISM: Artificial Sequence
<220> FEATURE:
<223> OTHER INFORMATION: siRNA

<400> SEQUENCE: 227
gcgcatcatc gattctgcc                                                    19

<210> SEQ ID NO 228
<211> LENGTH: 19
<212> TYPE: DNA
<213> ORGANISM: Artificial Sequence
<220> FEATURE:
<223> OTHER INFORMATION: siRNA

<400> SEQUENCE: 228
gaaggtagag accgagctc                                                    19

<210> SEQ ID NO 229
<211> LENGTH: 19
<212> TYPE: DNA
<213> ORGANISM: Artificial Sequence
<220> FEATURE:
<223> OTHER INFORMATION: siRNA

<400> SEQUENCE: 229
tcatcgattc tgcccggtc                                                    19

<210> SEQ ID NO 230
<211> LENGTH: 19
```

```
<212> TYPE: DNA
<213> ORGANISM: Artificial Sequence
<220> FEATURE:
<223> OTHER INFORMATION: siRNA

<400> SEQUENCE: 230
gaacggtatg aagacatgg                                                  19

<210> SEQ ID NO 231
<211> LENGTH: 19
<212> TYPE: DNA
<213> ORGANISM: Artificial Sequence
<220> FEATURE:
<223> OTHER INFORMATION: siRNA

<400> SEQUENCE: 231
cgtaggaatt gaggagtgt                                                  19

<210> SEQ ID NO 232
<211> LENGTH: 19
<212> TYPE: DNA
<213> ORGANISM: Artificial Sequence
<220> FEATURE:
<223> OTHER INFORMATION: siRNA

<400> SEQUENCE: 232
cactacgaga tcgccaaca                                                  19

<210> SEQ ID NO 233
<211> LENGTH: 19
<212> TYPE: DNA
<213> ORGANISM: Artificial Sequence
<220> FEATURE:
<223> OTHER INFORMATION: siRNA

<400> SEQUENCE: 233
gctgtccagt attgagcag                                                  19

<210> SEQ ID NO 234
<211> LENGTH: 19
<212> TYPE: DNA
<213> ORGANISM: Artificial Sequence
<220> FEATURE:
<223> OTHER INFORMATION: siRNA

<400> SEQUENCE: 234
gaccatgttt cctctcaat                                                  19

<210> SEQ ID NO 235
<211> LENGTH: 19
<212> TYPE: DNA
<213> ORGANISM: Artificial Sequence
<220> FEATURE:
<223> OTHER INFORMATION: siRNA

<400> SEQUENCE: 235
cgagacaacc tgacactgt                                                  19

<210> SEQ ID NO 236
<211> LENGTH: 19
<212> TYPE: DNA
<213> ORGANISM: Artificial Sequence
<220> FEATURE:
<223> OTHER INFORMATION: siRNA

<400> SEQUENCE: 236
```

```
cgtcttccac tacgagatc                                                    19

<210> SEQ ID NO 237
<211> LENGTH: 19
<212> TYPE: DNA
<213> ORGANISM: Artificial Sequence
<220> FEATURE:
<223> OTHER INFORMATION: siRNA

<400> SEQUENCE: 237
cctgcgaaga gcgaaacct                                                    19

<210> SEQ ID NO 238
<211> LENGTH: 19
<212> TYPE: DNA
<213> ORGANISM: Artificial Sequence
<220> FEATURE:
<223> OTHER INFORMATION: siRNA

<400> SEQUENCE: 238
gctgcctctg atcgtagga                                                    19

<210> SEQ ID NO 239
<211> LENGTH: 19
<212> TYPE: DNA
<213> ORGANISM: Artificial Sequence
<220> FEATURE:
<223> OTHER INFORMATION: siRNA

<400> SEQUENCE: 239
ccaagaccac tttcgacga                                                    19

<210> SEQ ID NO 240
<211> LENGTH: 19
<212> TYPE: DNA
<213> ORGANISM: Artificial Sequence
<220> FEATURE:
<223> OTHER INFORMATION: siRNA

<400> SEQUENCE: 240
gtctgctggg tgtgaccat                                                    19

<210> SEQ ID NO 241
<211> LENGTH: 19
<212> TYPE: DNA
<213> ORGANISM: Artificial Sequence
<220> FEATURE:
<223> OTHER INFORMATION: siRNA

<400> SEQUENCE: 241
ctctgatcgt aggaattga                                                    19

<210> SEQ ID NO 242
<211> LENGTH: 19
<212> TYPE: DNA
<213> ORGANISM: Artificial Sequence
<220> FEATURE:
<223> OTHER INFORMATION: siRNA

<400> SEQUENCE: 242
gctgggtgtg accatgttt                                                    19

<210> SEQ ID NO 243
<211> LENGTH: 19
<212> TYPE: DNA
<213> ORGANISM: Artificial Sequence
```

<220> FEATURE:
<223> OTHER INFORMATION: siRNA

<400> SEQUENCE: 243
gctgggtgtg accatgttt                                          19

<210> SEQ ID NO 244
<211> LENGTH: 19
<212> TYPE: DNA
<213> ORGANISM: Artificial Sequence
<220> FEATURE:
<223> OTHER INFORMATION: siRNA

<400> SEQUENCE: 244
cgacaagaag cgcatcatt                                          19

<210> SEQ ID NO 245
<211> LENGTH: 19
<212> TYPE: DNA
<213> ORGANISM: Artificial Sequence
<220> FEATURE:
<223> OTHER INFORMATION: siRNA

<400> SEQUENCE: 245
ctgccgagag gactagtat                                          19

<210> SEQ ID NO 246
<211> LENGTH: 19
<212> TYPE: DNA
<213> ORGANISM: Artificial Sequence
<220> FEATURE:
<223> OTHER INFORMATION: siRNA

<400> SEQUENCE: 246
gcctctgatc gtaggaatt                                          19

<210> SEQ ID NO 247
<211> LENGTH: 19
<212> TYPE: DNA
<213> ORGANISM: Artificial Sequence
<220> FEATURE:
<223> OTHER INFORMATION: siRNA

<400> SEQUENCE: 247
gcgctgttct tgctccaaa                                          19

<210> SEQ ID NO 248
<211> LENGTH: 19
<212> TYPE: DNA
<213> ORGANISM: Artificial Sequence
<220> FEATURE:
<223> OTHER INFORMATION: siRNA

<400> SEQUENCE: 248
ctgcctctga tcgtaggaa                                          19

<210> SEQ ID NO 249
<211> LENGTH: 19
<212> TYPE: DNA
<213> ORGANISM: Artificial Sequence
<220> FEATURE:
<223> OTHER INFORMATION: siRNA

<400> SEQUENCE: 249
gccctgaact tttccgtct                                          19

```
<210> SEQ ID NO 250
<211> LENGTH: 19
<212> TYPE: DNA
<213> ORGANISM: Artificial Sequence
<220> FEATURE:
<223> OTHER INFORMATION: siRNA

<400> SEQUENCE: 250
tgcctctgat cgtaggaat                                                  19

<210> SEQ ID NO 251
<211> LENGTH: 19
<212> TYPE: DNA
<213> ORGANISM: Artificial Sequence
<220> FEATURE:
<223> OTHER INFORMATION: siRNA

<400> SEQUENCE: 251
tgaccatgtt tcctctcaa                                                  19

<210> SEQ ID NO 252
<211> LENGTH: 19
<212> TYPE: DNA
<213> ORGANISM: Artificial Sequence
<220> FEATURE:
<223> OTHER INFORMATION: siRNA

<400> SEQUENCE: 252
ccatgtttcc tctcaataa                                                  19

<210> SEQ ID NO 253
<211> LENGTH: 19
<212> TYPE: DNA
<213> ORGANISM: Artificial Sequence
<220> FEATURE:
<223> OTHER INFORMATION: siRNA

<400> SEQUENCE: 253
ggtgacgaca agaagcgca                                                  19

<210> SEQ ID NO 254
<211> LENGTH: 19
<212> TYPE: DNA
<213> ORGANISM: Artificial Sequence
<220> FEATURE:
<223> OTHER INFORMATION: siRNA

<400> SEQUENCE: 254
acttttccgt cttccacta                                                  19

<210> SEQ ID NO 255
<211> LENGTH: 19
<212> TYPE: DNA
<213> ORGANISM: Artificial Sequence
<220> FEATURE:
<223> OTHER INFORMATION: siRNA

<400> SEQUENCE: 255
tccgtcttcc actacgaga                                                  19

<210> SEQ ID NO 256
<211> LENGTH: 19
<212> TYPE: DNA
<213> ORGANISM: Artificial Sequence
<220> FEATURE:
<223> OTHER INFORMATION: siRNA
```

-continued

```
<400> SEQUENCE: 256
ctctcctgcg aagagcgaa                                                19

<210> SEQ ID NO 257
<211> LENGTH: 19
<212> TYPE: DNA
<213> ORGANISM: Artificial Sequence
<220> FEATURE:
<223> OTHER INFORMATION: siRNA

<400> SEQUENCE: 257
ccaggaccag gctacttct                                                19

<210> SEQ ID NO 258
<211> LENGTH: 19
<212> TYPE: DNA
<213> ORGANISM: Artificial Sequence
<220> FEATURE:
<223> OTHER INFORMATION: siRNA

<400> SEQUENCE: 258
cctgctgcct ctgatcgta                                                19

<210> SEQ ID NO 259
<211> LENGTH: 19
<212> TYPE: DNA
<213> ORGANISM: Artificial Sequence
<220> FEATURE:
<223> OTHER INFORMATION: siRNA

<400> SEQUENCE: 259
ccgaacgcta tgaggacat                                                19

<210> SEQ ID NO 260
<211> LENGTH: 19
<212> TYPE: DNA
<213> ORGANISM: Artificial Sequence
<220> FEATURE:
<223> OTHER INFORMATION: siRNA

<400> SEQUENCE: 260
ccctgaactt ttccgtctt                                                19

<210> SEQ ID NO 261
<211> LENGTH: 19
<212> TYPE: DNA
<213> ORGANISM: Artificial Sequence
<220> FEATURE:
<223> OTHER INFORMATION: siRNA

<400> SEQUENCE: 261
ccgtcttcca ctacgagat                                                19

<210> SEQ ID NO 262
<211> LENGTH: 19
<212> TYPE: DNA
<213> ORGANISM: Artificial Sequence
<220> FEATURE:
<223> OTHER INFORMATION: siRNA

<400> SEQUENCE: 262
gagacaacct gacactgtg                                                19

<210> SEQ ID NO 263
```

```
<211> LENGTH: 19
<212> TYPE: DNA
<213> ORGANISM: Artificial Sequence
<220> FEATURE:
<223> OTHER INFORMATION: siRNA

<400> SEQUENCE: 263
gcatgtctgc tgggtgtga                                              19

<210> SEQ ID NO 264
<211> LENGTH: 19
<212> TYPE: DNA
<213> ORGANISM: Artificial Sequence
<220> FEATURE:
<223> OTHER INFORMATION: siRNA

<400> SEQUENCE: 264
tggctgagaa ctggacagt                                              19

<210> SEQ ID NO 265
<211> LENGTH: 19
<212> TYPE: DNA
<213> ORGANISM: Artificial Sequence
<220> FEATURE:
<223> OTHER INFORMATION: siRNA

<400> SEQUENCE: 265
gccgaacgct atgaggaca                                              19

<210> SEQ ID NO 266
<211> LENGTH: 19
<212> TYPE: DNA
<213> ORGANISM: Artificial Sequence
<220> FEATURE:
<223> OTHER INFORMATION: siRNA

<400> SEQUENCE: 266
ctgtccagta ttgagcaga                                              19

<210> SEQ ID NO 267
<211> LENGTH: 19
<212> TYPE: DNA
<213> ORGANISM: Artificial Sequence
<220> FEATURE:
<223> OTHER INFORMATION: siRNA

<400> SEQUENCE: 267
gtattgagca gaaaagcaa                                              19

<210> SEQ ID NO 268
<211> LENGTH: 19
<212> TYPE: DNA
<213> ORGANISM: Artificial Sequence
<220> FEATURE:
<223> OTHER INFORMATION: siRNA

<400> SEQUENCE: 268
cagctgttga gcgcaccta                                              19

<210> SEQ ID NO 269
<211> LENGTH: 19
<212> TYPE: DNA
<213> ORGANISM: Artificial Sequence
<220> FEATURE:
<223> OTHER INFORMATION: siRNA

<400> SEQUENCE: 269
```

```
gacaacctga cactgtgga                                                19

<210> SEQ ID NO 270
<211> LENGTH: 19
<212> TYPE: DNA
<213> ORGANISM: Artificial Sequence
<220> FEATURE:
<223> OTHER INFORMATION: siRNA

<400> SEQUENCE: 270
tggagagagc cagtctgat                                                19

<210> SEQ ID NO 271
<211> LENGTH: 19
<212> TYPE: DNA
<213> ORGANISM: Artificial Sequence
<220> FEATURE:
<223> OTHER INFORMATION: siRNA

<400> SEQUENCE: 271
cgaacgctat gaggacatg                                                19

<210> SEQ ID NO 272
<211> LENGTH: 19
<212> TYPE: DNA
<213> ORGANISM: Artificial Sequence
<220> FEATURE:
<223> OTHER INFORMATION: siRNA

<400> SEQUENCE: 272
ggtgctgtcc agtattgag                                                19

<210> SEQ ID NO 273
<211> LENGTH: 19
<212> TYPE: DNA
<213> ORGANISM: Artificial Sequence
<220> FEATURE:
<223> OTHER INFORMATION: siRNA

<400> SEQUENCE: 273
gaagcgcatc attgactca                                                19

<210> SEQ ID NO 274
<211> LENGTH: 19
<212> TYPE: DNA
<213> ORGANISM: Artificial Sequence
<220> FEATURE:
<223> OTHER INFORMATION: siRNA

<400> SEQUENCE: 274
tcgtaggaat tgaggagtg                                                19

<210> SEQ ID NO 275
<211> LENGTH: 19
<212> TYPE: DNA
<213> ORGANISM: Artificial Sequence
<220> FEATURE:
<223> OTHER INFORMATION: siRNA

<400> SEQUENCE: 275
gctgcgagac aacctgaca                                                19

<210> SEQ ID NO 276
<211> LENGTH: 19
<212> TYPE: DNA
```

<213> ORGANISM: Artificial Sequence
<220> FEATURE:
<223> OTHER INFORMATION: siRNA

<400> SEQUENCE: 276
tgctgtccag tattgagca                                                    19

<210> SEQ ID NO 277
<211> LENGTH: 19
<212> TYPE: DNA
<213> ORGANISM: Artificial Sequence
<220> FEATURE:
<223> OTHER INFORMATION: siRNA

<400> SEQUENCE: 277
ctgttcttgc tccaaaggg                                                    19

<210> SEQ ID NO 278
<211> LENGTH: 19
<212> TYPE: DNA
<213> ORGANISM: Artificial Sequence
<220> FEATURE:
<223> OTHER INFORMATION: siRNA

<400> SEQUENCE: 278
cctctgatcg taggaattg                                                    19

<210> SEQ ID NO 279
<211> LENGTH: 19
<212> TYPE: DNA
<213> ORGANISM: Artificial Sequence
<220> FEATURE:
<223> OTHER INFORMATION: siRNA

<400> SEQUENCE: 279
ccaccggtga cgacaagaa                                                    19

<210> SEQ ID NO 280
<211> LENGTH: 19
<212> TYPE: DNA
<213> ORGANISM: Artificial Sequence
<220> FEATURE:
<223> OTHER INFORMATION: siRNA

<400> SEQUENCE: 280
gtcttccact acgagatcg                                                    19

<210> SEQ ID NO 281
<211> LENGTH: 19
<212> TYPE: DNA
<213> ORGANISM: Artificial Sequence
<220> FEATURE:
<223> OTHER INFORMATION: siRNA

<400> SEQUENCE: 281
ctacctgaag atgaagggt                                                    19

<210> SEQ ID NO 282
<211> LENGTH: 19
<212> TYPE: DNA
<213> ORGANISM: Artificial Sequence
<220> FEATURE:
<223> OTHER INFORMATION: siRNA

<400> SEQUENCE: 282
ctataagaac gtggtgggc                                                    19

<210> SEQ ID NO 283
<211> LENGTH: 19
<212> TYPE: DNA
<213> ORGANISM: Artificial Sequence
<220> FEATURE:
<223> OTHER INFORMATION: siRNA

<400> SEQUENCE: 283
ctctggccaa gaccacttt                                                    19

<210> SEQ ID NO 284
<211> LENGTH: 19
<212> TYPE: DNA
<213> ORGANISM: Artificial Sequence
<220> FEATURE:
<223> OTHER INFORMATION: siRNA

<400> SEQUENCE: 284
cgctgttctt gctccaaag                                                    19

<210> SEQ ID NO 285
<211> LENGTH: 19
<212> TYPE: DNA
<213> ORGANISM: Artificial Sequence
<220> FEATURE:
<223> OTHER INFORMATION: siRNA

<400> SEQUENCE: 285
ccactttcga cgaggccat                                                    19

<210> SEQ ID NO 286
<211> LENGTH: 19
<212> TYPE: DNA
<213> ORGANISM: Artificial Sequence
<220> FEATURE:
<223> OTHER INFORMATION: siRNA

<400> SEQUENCE: 286
tgagaactgg acagtggca                                                    19

<210> SEQ ID NO 287
<211> LENGTH: 19
<212> TYPE: DNA
<213> ORGANISM: Artificial Sequence
<220> FEATURE:
<223> OTHER INFORMATION: siRNA

<400> SEQUENCE: 287
ctggccaaga ccactttcg                                                    19

<210> SEQ ID NO 288
<211> LENGTH: 19
<212> TYPE: DNA
<213> ORGANISM: Artificial Sequence
<220> FEATURE:
<223> OTHER INFORMATION: siRNA

<400> SEQUENCE: 288
ttgagcagaa aagcaacga                                                    19

<210> SEQ ID NO 289
<211> LENGTH: 19
<212> TYPE: DNA
<213> ORGANISM: Artificial Sequence
<220> FEATURE:

<223> OTHER INFORMATION: siRNA

<400> SEQUENCE: 289
tgcgagacaa cctgacact                                                    19

<210> SEQ ID NO 290
<211> LENGTH: 19
<212> TYPE: DNA
<213> ORGANISM: Artificial Sequence
<220> FEATURE:
<223> OTHER INFORMATION: siRNA

<400> SEQUENCE: 290
agctgttgag cgcacctaa                                                    19

<210> SEQ ID NO 291
<211> LENGTH: 19
<212> TYPE: DNA
<213> ORGANISM: Artificial Sequence
<220> FEATURE:
<223> OTHER INFORMATION: siRNA

<400> SEQUENCE: 291
gaacttttcc gtcttccac                                                    19

<210> SEQ ID NO 292
<211> LENGTH: 19
<212> TYPE: DNA
<213> ORGANISM: Artificial Sequence
<220> FEATURE:
<223> OTHER INFORMATION: siRNA

<400> SEQUENCE: 292
aaaagcaacg aggagggct                                                    19

<210> SEQ ID NO 293
<211> LENGTH: 19
<212> TYPE: DNA
<213> ORGANISM: Artificial Sequence
<220> FEATURE:
<223> OTHER INFORMATION: siRNA

<400> SEQUENCE: 293
tctcctgcga agagcgaaa                                                    19

<210> SEQ ID NO 294
<211> LENGTH: 19
<212> TYPE: DNA
<213> ORGANISM: Artificial Sequence
<220> FEATURE:
<223> OTHER INFORMATION: siRNA

<400> SEQUENCE: 294
ctgttgagcg cacctaacc                                                    19

<210> SEQ ID NO 295
<211> LENGTH: 19
<212> TYPE: DNA
<213> ORGANISM: Artificial Sequence
<220> FEATURE:
<223> OTHER INFORMATION: siRNA

<400> SEQUENCE: 295
cctgaacttt tccgtcttc                                                    19

```
<210> SEQ ID NO 296
<211> LENGTH: 19
<212> TYPE: DNA
<213> ORGANISM: Artificial Sequence
<220> FEATURE:
<223> OTHER INFORMATION: siRNA

<400> SEQUENCE: 296
gctgttcttg ctccaaagg                                              19

<210> SEQ ID NO 297
<211> LENGTH: 19
<212> TYPE: DNA
<213> ORGANISM: Artificial Sequence
<220> FEATURE:
<223> OTHER INFORMATION: siRNA

<400> SEQUENCE: 297
aggccgaacg ctatgagga                                              19

<210> SEQ ID NO 298
<211> LENGTH: 19
<212> TYPE: DNA
<213> ORGANISM: Artificial Sequence
<220> FEATURE:
<223> OTHER INFORMATION: siRNA

<400> SEQUENCE: 298
attgaggagt gtcccgcct                                              19

<210> SEQ ID NO 299
<211> LENGTH: 19
<212> TYPE: DNA
<213> ORGANISM: Artificial Sequence
<220> FEATURE:
<223> OTHER INFORMATION: siRNA

<400> SEQUENCE: 299
gtgaccatgt ttcctctca                                              19

<210> SEQ ID NO 300
<211> LENGTH: 19
<212> TYPE: DNA
<213> ORGANISM: Artificial Sequence
<220> FEATURE:
<223> OTHER INFORMATION: siRNA

<400> SEQUENCE: 300
caagaccact ttcgacgag                                              19

<210> SEQ ID NO 301
<211> LENGTH: 19
<212> TYPE: DNA
<213> ORGANISM: Artificial Sequence
<220> FEATURE:
<223> OTHER INFORMATION: siRNA

<400> SEQUENCE: 301
aacttttccg tcttccact                                              19

<210> SEQ ID NO 302
<211> LENGTH: 19
<212> TYPE: DNA
<213> ORGANISM: Artificial Sequence
<220> FEATURE:
<223> OTHER INFORMATION: siRNA
```

```
<400> SEQUENCE: 302
tgatcgtagg aattgagga                                               19

<210> SEQ ID NO 303
<211> LENGTH: 19
<212> TYPE: DNA
<213> ORGANISM: Artificial Sequence
<220> FEATURE:
<223> OTHER INFORMATION: siRNA

<400> SEQUENCE: 303
ggagagagcc agtctgatc                                               19

<210> SEQ ID NO 304
<211> LENGTH: 19
<212> TYPE: DNA
<213> ORGANISM: Artificial Sequence
<220> FEATURE:
<223> OTHER INFORMATION: siRNA

<400> SEQUENCE: 304
agcaggccga acgctatga                                               19

<210> SEQ ID NO 305
<211> LENGTH: 19
<212> TYPE: DNA
<213> ORGANISM: Artificial Sequence
<220> FEATURE:
<223> OTHER INFORMATION: siRNA

<400> SEQUENCE: 305
aggacatggc agccttcat                                               19

<210> SEQ ID NO 306
<211> LENGTH: 19
<212> TYPE: DNA
<213> ORGANISM: Artificial Sequence
<220> FEATURE:
<223> OTHER INFORMATION: siRNA

<400> SEQUENCE: 306
acgacaagaa gcgcatcat                                               19

<210> SEQ ID NO 307
<211> LENGTH: 19
<212> TYPE: DNA
<213> ORGANISM: Artificial Sequence
<220> FEATURE:
<223> OTHER INFORMATION: siRNA

<400> SEQUENCE: 307
accatgtttc ctctcaata                                               19

<210> SEQ ID NO 308
<211> LENGTH: 19
<212> TYPE: DNA
<213> ORGANISM: Artificial Sequence
<220> FEATURE:
<223> OTHER INFORMATION: siRNA

<400> SEQUENCE: 308
tgccgagagg actagtatg                                               19

<210> SEQ ID NO 309
<211> LENGTH: 19
```

```
<212> TYPE: DNA
<213> ORGANISM: Artificial Sequence
<220> FEATURE:
<223> OTHER INFORMATION: siRNA

<400> SEQUENCE: 309
tctgatcgta ggaattgag                                              19

<210> SEQ ID NO 310
<211> LENGTH: 19
<212> TYPE: DNA
<213> ORGANISM: Artificial Sequence
<220> FEATURE:
<223> OTHER INFORMATION: siRNA

<400> SEQUENCE: 310
tgggtgtgac catgtttcc                                              19

<210> SEQ ID NO 311
<211> LENGTH: 19
<212> TYPE: DNA
<213> ORGANISM: Artificial Sequence
<220> FEATURE:
<223> OTHER INFORMATION: siRNA

<400> SEQUENCE: 311 tgaactttc cgtcttcca                                               19

<210> SEQ ID NO 312
<211> LENGTH: 19
<212> TYPE: DNA
<213> ORGANISM: Artificial Sequence
<220> FEATURE:
<223> OTHER INFORMATION: siRNA

<400> SEQUENCE: 312
gaattgagga gtgtcccgc                                              19

<210> SEQ ID NO 313
<211> LENGTH: 19
<212> TYPE: DNA
<213> ORGANISM: Artificial Sequence
<220> FEATURE:
<223> OTHER INFORMATION: siRNA

<400> SEQUENCE: 313
tttccgtctt ccactacga                                              19

<210> SEQ ID NO 314
<211> LENGTH: 19
<212> TYPE: DNA
<213> ORGANISM: Artificial Sequence
<220> FEATURE:
<223> OTHER INFORMATION: siRNA

<400> SEQUENCE: 314
ctgctgcctc tgatcgtag                                              19

<210> SEQ ID NO 315
<211> LENGTH: 19
<212> TYPE: DNA
<213> ORGANISM: Artificial Sequence
<220> FEATURE:
<223> OTHER INFORMATION: siRNA

<400> SEQUENCE: 315
```
ggccctgaac ttttccgtc                                                19

<210> SEQ ID NO 316
<211> LENGTH: 19
<212> TYPE: DNA
<213> ORGANISM: Artificial Sequence
<220> FEATURE:
<223> OTHER INFORMATION: siRNA

<400> SEQUENCE: 316
gccaagacca ctttcgacg                                                19

<210> SEQ ID NO 317
<211> LENGTH: 19
<212> TYPE: DNA
<213> ORGANISM: Artificial Sequence
<220> FEATURE:
<223> OTHER INFORMATION: siRNA

<400> SEQUENCE: 317
tctggccaag accactttc                                                19

<210> SEQ ID NO 318
<211> LENGTH: 19
<212> TYPE: DNA
<213> ORGANISM: Artificial Sequence
<220> FEATURE:
<223> OTHER INFORMATION: siRNA

<400> SEQUENCE: 318
ctgaactttt ccgtcttcc                                                19

<210> SEQ ID NO 319
<211> LENGTH: 19
<212> TYPE: DNA
<213> ORGANISM: Artificial Sequence
<220> FEATURE:
<223> OTHER INFORMATION: siRNA

<400> SEQUENCE: 319
aagcgcatca ttgactcag                                                19

<210> SEQ ID NO 320
<211> LENGTH: 19
<212> TYPE: DNA
<213> ORGANISM: Artificial Sequence
<220> FEATURE:
<223> OTHER INFORMATION: siRNA

<400> SEQUENCE: 320
tgttgagcgc acctaacca                                                19

<210> SEQ ID NO 321
<211> LENGTH: 19
<212> TYPE: DNA
<213> ORGANISM: Artificial Sequence
<220> FEATURE:
<223> OTHER INFORMATION: siRNA

<400> SEQUENCE: 321
tacctgaaga tgaagggtg                                                19

<210> SEQ ID NO 322
<211> LENGTH: 19
<212> TYPE: DNA
<213> ORGANISM: Artificial Sequence
<220> FEATURE:
<223> OTHER INFORMATION: siRNA

<400> SEQUENCE: 322
accactttcg acgaggcca                                                    19

<210> SEQ ID NO 323
<211> LENGTH: 19
<212> TYPE: DNA
<213> ORGANISM: Artificial Sequence
<220> FEATURE:
<223> OTHER INFORMATION: siRNA

<400> SEQUENCE: 323
acgaggccat ggctgatct                                                    19

<210> SEQ ID NO 324
<211> LENGTH: 19
<212> TYPE: DNA
<213> ORGANISM: Artificial Sequence
<220> FEATURE:
<223> OTHER INFORMATION: siRNA

<400> SEQUENCE: 324
gatcccactc ttcttgcag                                                    19

<210> SEQ ID NO 325
<211> LENGTH: 19
<212> TYPE: DNA
<213> ORGANISM: Artificial Sequence
<220> FEATURE:
<223> OTHER INFORMATION: siRNA

<400> SEQUENCE: 325
cttttccgtc ttccactac                                                    19

<210> SEQ ID NO 326
<211> LENGTH: 19
<212> TYPE: DNA
<213> ORGANISM: Artificial Sequence
<220> FEATURE:
<223> OTHER INFORMATION: siRNA

<400> SEQUENCE: 326
gccgagagga ctagtatgg                                                    19

<210> SEQ ID NO 327
<211> LENGTH: 19
<212> TYPE: DNA
<213> ORGANISM: Artificial Sequence
<220> FEATURE:
<223> OTHER INFORMATION: siRNA

<400> SEQUENCE: 327
gctgttgagc gcacctaac                                                    19

<210> SEQ ID NO 328
<211> LENGTH: 19
<212> TYPE: DNA
<213> ORGANISM: Artificial Sequence
<220> FEATURE:
<223> OTHER INFORMATION: siRNA

<400> SEQUENCE: 328
caggaccagg ctacttctc                                                    19

```
<210> SEQ ID NO 329
<211> LENGTH: 19
<212> TYPE: DNA
<213> ORGANISM: Artificial Sequence
<220> FEATURE:
<223> OTHER INFORMATION: siRNA

<400> SEQUENCE: 329
cctataagaa cgtggtggg                                                19

<210> SEQ ID NO 330
<211> LENGTH: 19
<212> TYPE: DNA
<213> ORGANISM: Artificial Sequence
<220> FEATURE:
<223> OTHER INFORMATION: siRNA

<400> SEQUENCE: 330
ctgggtgtga ccatgtttc                                                19

<210> SEQ ID NO 331
<211> LENGTH: 19
<212> TYPE: RNA
<213> ORGANISM: Artificial Sequence
<220> FEATURE:
<223> OTHER INFORMATION: siCONT

<400> SEQUENCE: 331
cuuacgcuga guacuucga                                                19

<210> SEQ ID NO 332
<211> LENGTH: 21
<212> TYPE: DNA
<213> ORGANISM: Artificial Sequence
<220> FEATURE:
<223> OTHER INFORMATION: mRPL13A-F

<400> SEQUENCE: 332
cgatagtgca tcttggcctt t                                             21

<210> SEQ ID NO 333
<211> LENGTH: 21
<212> TYPE: DNA
<213> ORGANISM: Artificial Sequence
<220> FEATURE:
<223> OTHER INFORMATION: mRPL13A-R

<400> SEQUENCE: 333
cctgctgctc tcaaggttgt t                                             21

<210> SEQ ID NO 334
<211> LENGTH: 20
<212> TYPE: DNA
<213> ORGANISM: Artificial Sequence
<220> FEATURE:
<223> OTHER INFORMATION: hRPL13A-F

<400> SEQUENCE: 334
agctcatgag gctacggaaa                                               20

<210> SEQ ID NO 335
<211> LENGTH: 19
<212> TYPE: DNA
<213> ORGANISM: Artificial Sequence
<220> FEATURE:
<223> OTHER INFORMATION: hRPL13A-R
```

-continued

<400> SEQUENCE: 335
cgtacattcc agggcaaca                                                        19

<210> SEQ ID NO 336
<211> LENGTH: 21
<212> TYPE: DNA
<213> ORGANISM: Artificial Sequence
<220> FEATURE:
<223> OTHER INFORMATION: mAR-F

<400> SEQUENCE: 336
ggtcttaggc tcaggccatt a                                                     21

<210> SEQ ID NO 337
<211> LENGTH: 20
<212> TYPE: DNA
<213> ORGANISM: Artificial Sequence
<220> FEATURE:
<223> OTHER INFORMATION: mAR-R

<400> SEQUENCE: 337
cgcttatggt ggaaacctct                                                       20

<210> SEQ ID NO 338
<211> LENGTH: 20
<212> TYPE: DNA
<213> ORGANISM: Artificial Sequence
<220> FEATURE:
<223> OTHER INFORMATION: hAR-F

<400> SEQUENCE: 338
acacctactc tgggaagcgt                                                       20

<210> SEQ ID NO 339
<211> LENGTH: 20
<212> TYPE: DNA
<213> ORGANISM: Artificial Sequence
<220> FEATURE:
<223> OTHER INFORMATION: hAR-R

<400> SEQUENCE: 339
gccaggtatt tgtggttcgt                                                       20

<210> SEQ ID NO 340
<211> LENGTH: 19
<212> TYPE: DNA
<213> ORGANISM: Artificial Sequence
<220> FEATURE:
<223> OTHER INFORMATION: mSFN-F

<400> SEQUENCE: 340
gtgtgtgcga caccgtact                                                        19

<210> SEQ ID NO 341
<211> LENGTH: 19
<212> TYPE: DNA
<213> ORGANISM: Artificial Sequence
<220> FEATURE:
<223> OTHER INFORMATION: mSFN-R

<400> SEQUENCE: 341
ctcggctagg tagcggtag                                                        19

<210> SEQ ID NO 342

```
<211> LENGTH: 21
<212> TYPE: DNA
<213> ORGANISM: Artificial Sequence
<220> FEATURE:
<223> OTHER INFORMATION: hSFN-F

<400> SEQUENCE: 342
agaagcgcat cattgactca g                                              21

<210> SEQ ID NO 343
<211> LENGTH: 21
<212> TYPE: DNA
<213> ORGANISM: Artificial Sequence
<220> FEATURE:
<223> OTHER INFORMATION: hSFN-R

<400> SEQUENCE: 343
tctcgtagtg gaagacggaa a                                              21
```

DOUBLE-STRANDED OLIGO RNA TARGETED TO AMPHIREGULIN AND PHARMACEUTICAL COMPOSITION COMPRISING SAME FOR PREVENTING OR TREATING FIBROSIS OR RESPIRATORY DISEASES

CROSS-REFERENCE TO RELATED APPLICATIONS

This application is a U.S. national phase application under the provisions of 35 U.S.C. § 371 of International Patent Application No. PCT/KR15/03400 filed Apr. 6, 2015, which in turn claims priority of Korean Patent Application No. 10-2014-0040699 filed Apr. 4, 2014. The disclosures of such international patent application and Korean priority patent application are hereby incorporated herein by reference in their respective entireties, for all purposes.

TECHNICAL FIELD

The present invention relates to a novel double strand oligo RNA and pharmaceutical compositions for preventing or treating fibrosis or respiratory diseases containing the same, and a nanoparticle containing the high-efficiency double-stranded oligo RNA structure. More particularly, the present invention relates to an siRNA which has a structure in which a hydrophilic material and a hydrophobic material are conjugated to both ends of a double-stranded oligo RNA (siRNA) via a simple covalent bond or linker-mediated covalent bond in order to be efficiently delivered into cells, and may be converted into a nanoparticle form in an aqueous solution by hydrophobic interactions of double-stranded oligo RNA structure containing the same, and nanoparticles containing the high-efficiency double-stranded oligo RNA structure, wherein the siRNA is preferably specific for amphiregulin or stratifin, which is a respiratory disease-related gene.

In addition, the present invention relates to a pharmaceutical composition for preventing or treating fibrosis or respiratory diseases, containing a novel siRNA, a high-efficiency double-stranded oligo RNA structure containing the siRNA, or a nanoparticle containing the high-efficiency double-stranded oligo RNA structure, as an active ingredient.

BACKGROUND ART

A technology of inhibiting expression of genes is an important tool for developing a therapeutic agent for treating diseases and verifying a target. As the related art for inhibiting expression of a target gene, technologies of transducing a transgene for the target gene have been disclosed. That is, a method of transducing a transgene in an antisense direction based on a promoter (Sheehy et al., Proc. Natl. Acad. Sci., USA, 85:8805-8808, 1988; Smith et al., Nature, 334:724-726, 1988) and a method of transducing a transgene in a sense direction based on a promoter (Napoli et al., Plant Cell, 2:279-289, 1990; van der Krol et al., Plant Cell, 2:291-299, 1990; U.S. Pat. Nos. 5,034,323; 5,231,020; and 5,283,184) have been disclosed.

Meanwhile, recently, it was reported that a gene inhibition or RNA interference (RNAi) phenomenon after transcription is caused by accumulation of a double-stranded RNA fragment having 20 to 25 base pairs, and the double-stranded oligo RNA is synthesized from an RNA template. The double-stranded oligo RNA fragment is named as "small interfering RNA" (hereinafter, referred to as siRNA). Thereafter, it has been demonstrated that the siRNA is an important factor that inhibits expression of genes in various organisms including mammals (Fire et al., Nature, 391:806-811, 1998; Timmons & Fire, Nature, 395:854, 1998; Kennerdell & Carthew, Cell, 95:1017-1026, 1998; Elbashir et al., Nature, 411:494-497, 2001; WO 99/32619). In addition, it was known that a double-stranded siRNA is converted into a single-stranded RNA by an RNA-induced silencing complex (RISC) and then bind to and inactivate the mRNA (Novina & Sharp, Nature, 430:161-164, 2004). As described above, a technology for inhibiting expression of a gene using the siRNA, which is used to inhibit the expression of a target gene in a target cell and observe changes caused by the inhibition, is advantageously used to identify functions of the target gene in the target cell. Particularly, it is expected that inhibiting functions of a target gene in an infectious virus, cancer cells, or the like, may be usefully applied to develop a therapeutic method of the corresponding disease. As a result of in vitro studies and in vivo studies using experimental animals, it has been reported that expression of a target gene may be inhibited by the siRNA. For example, a method of treating cancer cells by inhibiting expression of Bcl2 protein in the cancer cells using an siRNA has been disclosed in International Patent No. WO 03/070969, and a method of treating cancer cells by inhibiting expression of vascular endothelial growth factor (VEGF) protein causing angiogenesis using an siRNA has been disclosed in WO 04/009769.

In addition, siRNA complementarily bind to the target mRNA to regulate expression of the target gene in a sequence-specific manner, it can be advantageously used in a remarkably enlarged as compared to conventional antibody-based drugs or small molecule drugs (Progress Towards in Vivo Use of siRNAs: MOLECULAR THERAPY: 2006 13(4):664-670).

In spite of excellent effects and various usage ranges of the siRNA, but in order to develop the siRNA as a therapeutic agent, it is required to improve the in vivo stability and intracellular delivery efficiency of siRNA so as to effectively deliver siRNA into its target (Harnessing In Vivo siRNA Delivery for Drug Discovery and Therapeutic Development: Drug Discov. Today: 2006 January; 11(1-2):67-73).

In order to improve in vivo stability of siRNA problems associated with innate immune stimulation problem of the siRNA, research into a technology of modifying some nucleotides or a backbone of the siRNA so as to have resistance against nuclease or using a carrier such as a viral vector, liposome, nanoparticles have been actively conducted.

Delivery system using the viral vector such as adenovirus or retrovirus has high transfection efficiency, but immunogenicity and oncogenicity are also high. On the other hand, a non-viral delivery system containing nanoparticles are evaluated to have low intracellular delivery efficiency compared to a viral delivery system, but has advantages, including high safety in vivo, target-specific delivery, have an improved delivery efficiency due to uptake and internalization of RNAi oligonucleotide contained therein by cells or tissue, and does not almost cause cytotoxicity and immune stimulation, such that currently, the non-viral delivery system has been evaluated as a potential delivery system as compared to the viral delivery system (Nonviral Delivery of Synthetic siRNAs In Vivo, J. Clin. Invest: 2007 Dec. 3; 117(12):3623-632).

Among the non-viral delivery systems, in a method using a nanocarrier, nanoparticles are formed using various polymers such as liposome, a cationic polymer complex, and the like, and then siRNA is supported on these nanoparticles, that is, the nanocarriers to thereby be delivered into cells. In the methods using the nanocarrier, polymeric nanoparticles, polymer micelles, lipoplexes, and the like are mainly used. Among them, the lipoplex is composed of a cationic lipid and interacts with an anionic lipid of endosome in cells to destabilize endosome, thereby serving to deliver the siRNA into the cells.

Further, it was known that the efficiency of the siRNA in vivo can be increased by conjugating a chemical compound or the like to an end region of a passenger (sense) strand of the siRNA to allow the siRNA to have improved pharmacokinetic characteristics (Nature 11; 432(7014): 173-8, 2004). Here, stability of the siRNA is changed depending on properties of the chemical bound to an end of a sense (passenger) or antisense (guide) strand of the siRNA. For example, an siRNA conjugated with a polymer compound such as polyethylene glycol (PEG) interacts with an anionic phosphate group of the siRNA in a presence of a cationic material to form a complex, thereby serving as a carrier having improved siRNA stability (J. Control Release 129(2): 107-16, 2008). Particularly, since micelles made of a polymer complex have a structure spontaneously formed while having significantly small sizes and significantly uniform distribution as compared to microsphere, nanoparticles, or the like, which is another system used as a drug delivery carrier, there are advantages in that quality of a product may be easily managed and reproducibility may be easily secured.

Further, in order to improve intracellular delivery efficiency of the siRNA, a technology for securing stability of the siRNA and implementing efficient cell membrane permeability using an siRNA conjugate obtained by conjugating a hydrophilic material (for example, polyethylene glycol (PEG)), which is a biocompatible polymer, to the siRNA via a simple covalent bond or a linker-mediated covalent bond has been developed (Korean Patent No. 883471). However, even though the siRNA is chemically modified and conjugated to polyethylene glycol (PEG) (that is, siRNA is PEGylated), disadvantages such as low stability in vivo and difficulty in delivering the siRNA into a target organ still remain. In order to overcome these disadvantages, a double-stranded oligo RNA structure in which a hydrophilic material and a hydrophobic material are bound to an oligonucleotide, particularly, a double-stranded oligo RNA such as the siRNA has been developed. The structure forms self-assembled nanoparticles named as "Self-Assembled Micelle Inhibitory RNA (SAMiRNA™)" (see Korean Patent No. 1224828). A SNiRNA™ technology has advantages in that homogenous nanoparticles having a significantly small size as compared to existing delivery technologies may be obtained.

Chronic obstructive pulmonary disease (hereinafter, referred to as 'COPD'), which is one of the representative pulmonary diseases together with asthma, is different from asthma in that COPD is accompanied by irreversible airway obstruction, and is a respiratory disease characterized by abnormal inflammatory responses in the lung, caused by repetitive infection, inhalation of harmful particles and gases, or smoking, and air flow limitation corresponding thereto, which is not completely reversible and is progressive (Am. J. Respir. Crit. Care Med., 163:1256-1276, 2001). The severity of COPD is emerging around the world. The reason is that in 1990, COPD ranked sixth place among causes of death due to disease, but it is predicted that in 2020, COPD will rank third place, and has become a disease of which an incidence rate is uniquely increased among the top 10 diseases. Further, since COPD is predicted to rank fourth place among causes of disabilities due to diseases, it is expected that social and financial burden due to COPD will rapidly increase (Lancet, 349:1498-1504, 1997). COPD, which is a disease caused by pathological changes in the bronchioles and pulmonary parenchyma due to airway and pulmonary parenchymal inflammation, is characterized by obstructive bronchiolitis and emphysema (destruction of the pulmonary parenchyma). Types of COPD include chronic obstructive bronchitis, chronic bronchiolitis, and emphysema. In the case of COPD, the number of neutrophils is increased, and cytokines such as granulocyte macrophage colony-stimulating factor (GM-CSF), tumor necrosis factor (TNF)-α, interleukin (IL)-8, and macrophage inflammatory protein (MIP)-2 are secreted. Inflammation occurs in the airway, the muscle wall becomes thick, and mucus secretion is increased, thereby causing bronchial obstruction. When the bronchus is obstructed, the lung sac is expanded and damaged, such that, an exchange ability of oxygen and carbon dioxide is damaged, and occurrence of respiratory failure is increased. Even though 8% of adults over the age of 45 are COPD patients in Korea, medical treatment is biased toward only lung cancer, and as a method of treating COPD according to the related art, a therapeutic agent having an anti-inflammatory effect or a bronchodilatory effect is used. However, essential prevention and treatment for COPD using a gene therapeutic agent is not yet sufficiently developed. A representative example of the therapeutic agents having the anti-inflammatory effect includes glucocorticoid, leukotriene modifiers, theophylline, and the like. However, since the glucocorticoid has potent effects, but is administered by inhalation due to its side effects, and it does not selectively inhibit inflammatory reactions, but inhibit all immune responses and anti-inflammatory responses, in some cases, necessary immune responses may also be inhibited. Since side effects of the leukotriene modifier is small, but there is a limitation in the effect thereof, and when the leukotriene modifier is used alone, it is impossible to regulate asthma. Therefore, in most cases, the leukotriene modifiers are auxiliary used. Theophylline has a problem in that effects are not excellent and there is a risk of side effects. Therefore, the demand for a novel therapeutic agent capable of having excellent effects of preventing and treating COPD and decreasing side effects has been urgently required.

Meanwhile, idiopathic pulmonary fibrosis (hereinafter, referred to as 'IPF'), which is a kind of fibrosis, is a disease in which chronic inflammatory cells penetrate into a wall of the lung sac (alveola) to cause various changes by making the lung become hard, which causes severe structural changes in the lung tissue, such that lung functions are gradually deteriorated to thereby ultimately result in death. However, an effective treatment thereof does not exist yet, and IPF is generally diagnosed only when symptoms appear, and has extremely bad prognosis since a median survival time is only about three to five years. It is reported that an incidence frequency of IPF is about 3 to 5 per 100,000 people in foreign countries, and it is known that mostly, an incidence rate of IPF is increased over the age of 50, and the incidence rate of IPF in men is 2 times higher than that in women.

The cause of IPF has not been yet clearly identified, and it was merely reported that the incidence of IPF is high in smokers, and anti-depressants, chronic lung inhalation due to gastro esophageal reflux, metal dust, wood dust, solvent inhalation, or the like, is a risk factor related to occurrence of IPF. However, factors having a certain causal factors cannot be found in the majority of patients.

It is known that when IPF is not treated, IPF is continuously worsened, and thus, about 50% or more of patients die within 3 to 5 years. In addition, once a lung is completely hardened by fibrosis as the disease progresses, even when any type of treatment is conducted, a patient does not improve. Therefore, it is predicted that even though treatment is conducted, only when treatment is conducted at an early stage, a possibility for an effect to be exhibited will be increased. As the currently used therapeutic agent, a combination therapy method using steroid and azathioprine or cyclophosphamide, has been known, but it is difficult to say that there are special effects, and attempts of several fibrosis inhibitors in animal experiments and small group of patients failed in proving clear effects. Particularly, there is no other effective therapeutic method in patients with end-stage IPF except for lung transplantation. Therefore, the development of a more efficient therapeutic agent for IPF has been urgently required.

Diseases in which for some reason, tissue or organs are consolidated due to excessive fibrosis of connective tissue are collectively referred to as fibrosis, and all processes of fibrosis are the same as those of scar treatment regardless of a site. It has been almost impossible to completely cure fibrosis symptoms up to now, and a method of treating fibrosis has still been developed and studied. An effective therapeutic agent for fibrosis may also be applied to various diseases accompanied with fibrosis as well as cirrhosis, myelofibrosis, myocardial fibrosis, renal fibrosis, and pulmonary fibrosis, which are representative fibrosis diseases. Therefore, the development of an efficient therapeutic agent for fibrosis has been urgently required.

Meanwhile, it is known that amphiregulin binds to an epithelial growth factor receptor (EGFR) to activate an EGFR pathway and participates in cell proliferation, and the fact that expression of amphiregulin may be inhibited by an amphiregulin-specific siRNA, and the amphiregulin-specific siRNA may have a therapeutic effect for specific type breast cancer has been disclosed (Cancer Res., 2008; 68:225-2265). Further, it was reported that cell penetration in inflammatory breast cancer may be suppressed using a shRNA for amphiregulin (J. Cell Physiol., 2011, 226(10): 2691-2701), and when expression of amphiregulin is inhibited using an amphiregulin-specific shRNA, pulmonary artery remodeling is suppressed in mice exposed to cigarette smoke. It was reported that amphiregulin is related to airway smooth muscle (ASM) hyperplasia and angiogenesis, and particularly promotes airway remodeling in asthma patients, and an epidermal growth factor (EGF) excessively secreted in tissue remodeling in acute asthma and amphiregulin are associated with each other.

In addition, it was reported that stratifin (14-3-3 sigma protein or SFN) participates in various intercellular functions such as cell cycle, apoptosis, signaling mechanism regulation, cellular trafficking, cell proliferation and differentiation, cell survival, and the like (Mol. Cell Biochem., 2007, 305:255-64), and participates in TGF-beta 1-mediated growth inhibition using a stratifin-specific siRNA (Mol. Cell, 2010; 0.2; 305-309). In addition, it was reported that a factor regulating formation and decomposition of collagen participates in the airway remodeling in asthma, and particularly, metalloproteinase (MMP)-1 performs an important function in decomposition of collagen, and one of the important factors regulating expression of MMP-1 in the airway is stratifin.

As described above, possibilities of amphiregulin and stratifin as targets for treating respiratory diseases and fibrosis, particularly, COPD and idiopathic pulmonary fibrosis have been suggested, but until now, an siRNA therapeutic agent for amphiregulin and stratifin and a delivery technology of the an siRNA therapeutic agent have not been sufficiently developed. Therefore, the demand for an siRNA therapeutic agent capable of specifically and highly efficiently inhibiting expression of amphiregulin and stratifin, and a delivery technology thereof is significantly high on the market.

DISCLOSURE

An object of the present invention is to provide a novel double-stranded oligo RNA, preferably, an siRNA, capable of specifically and highly efficiently inhibiting a specific gene, a double-stranded oligo RNA structure containing the same, and a nanoparticle containing the double-stranded oligo RNA structure.

Another object of the present invention is to provide a pharmaceutical composition for preventing or treating fibrosis or respiratory diseases, containing the siRNA, the double-stranded oligo RNA structure containing the siRNA, or the nanoparticle containing the double-stranded oligo RNA structure, as an active ingredient.

Another object of the present invention is to provide a method of preventing or treating fibrosis or respiratory diseases including administering the pharmaceutical composition for preventing or treating fibrosis or respiratory diseases to a subject in need thereof.

DETAILED DESCRIPTION OF THE EMBODIMENTS

Figure 1:
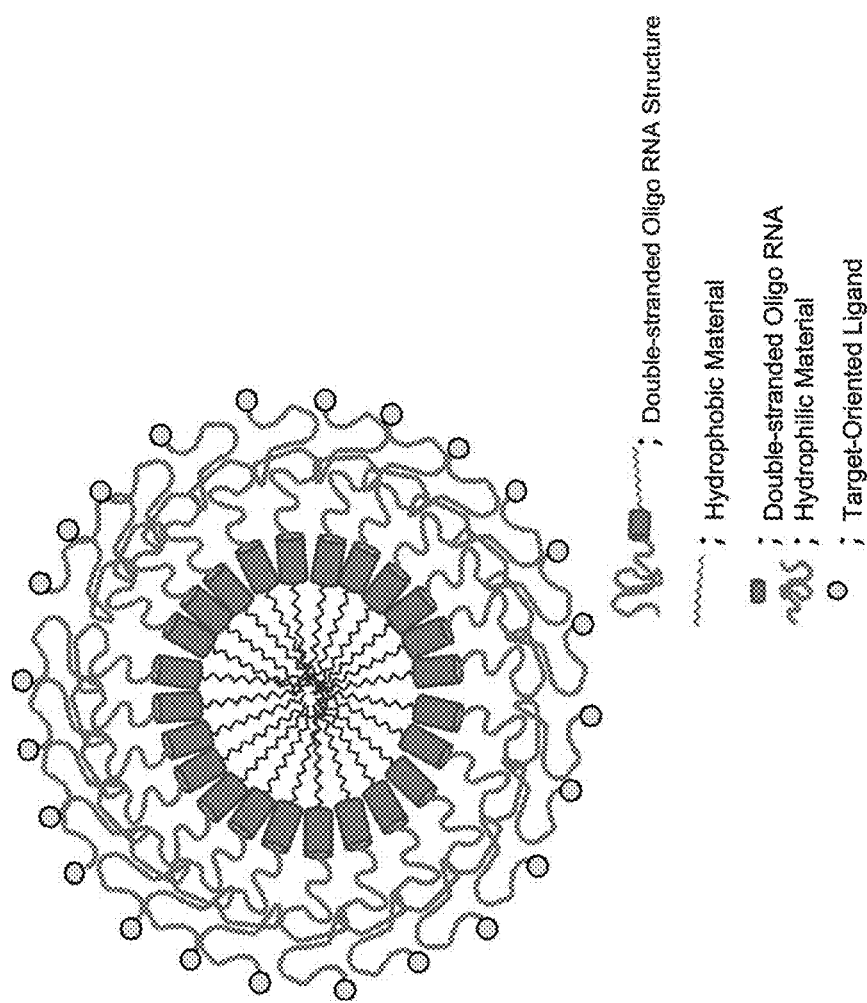
FIG. 1 is a mimetic view of a nanoparticle containing a double-stranded oligo RNA structure according to the present invention.

Unless otherwise defined herein, all of the technical and scientific terms used in the present specification have the same meanings as those generally understood by specialists in the skilled art to which the present invention pertains. Generally, nomenclature used in the present specification is well known and commonly used in the art.

In order to achieve the above-mentioned object, the present invention provides an siRNA comprising a sense strand having any one sequence selected from the group consisting of SEQ ID NOS: 1 to 330 and an antisense strand having a sequence complementary thereto.

In addition, the present invention provides a double-stranded oligo RNA structure comprising a structure represented by the following Structural Formula 1, wherein in the following Structural Formula 1, A is a hydrophilic material, B is a hydrophobic material, X and Y are each independently a simple covalent bond or linker-mediated covalent bond, and R is an siRNA.

A-X-R-Y-B [Structural Formula 1]

Further, the present invention provides a nanoparticle comprising the double-stranded oligo RNA structure.

In addition, the present invention provides a pharmaceutical composition for preventing or treating fibrosis or respiratory diseases, comprising the siRNA, the double-stranded oligo RNA structure, or the nanoparticle.

Further, the present invention provides a method of preventing or treating fibrosis or respiratory diseases, comprising a step of administering the pharmaceutical composition for preventing or treating fibrosis or respiratory diseases to a subject in need thereof.

In the present invention, a novel amphiregulin- or stratifin-specific siRNA was prepared. As a result, it was confirmed that since the novel amphiregulin- or stratifin-specific siRNA has a base sequence designed so as to complementarily bind to an mRNA encoding amphiregulin or stratifin, the novel amphiregulin- or stratifin-specific siRNA may effectively inhibit expression of amphiregulin or stratifin.

In one aspect, the present invention relates to an siRNA comprising a sense strand (first oligonucleotide) having any one sequence selected from the group consisting of SEQ ID NOS: 1 to 330 and an antisense strand (second oligonucleotide) having a sequence complementary thereto.

```
                                         (SEQ ID NO: 1)
       5'-ggaguaugauaaugaacca-3', (SEQ ID NO: 2)
       5'-caguaguagcugucacuau-3', (SEQ ID NO: 3)
       5'-agacucacagcgaggauga-3', (SEQ ID NO: 4)
       5'-cacaaauauccggcuauau-3', (SEQ ID NO: 5)
       5'-caccauaagcgaaaugccu-3', (SEQ ID NO: 6)
       5'-gauuacuuuggugaacggu-3', (SEQ ID NO: 7)
       5'-caguugucacuuuuuauga-3', (SEQ ID NO: 8)
       5'-ggaccuauccaagauugca-3', (SEQ ID NO: 9)
       5'-cguuaucacagugcaccuu-3', (SEQ ID NO: 10)
       5'-ccuagcugaggacaaugca-3', (SEQ ID NO: 11)
       5'-ggaagagagguuuccacca-3', (SEQ ID NO: 12)
       5'-cucagaggaguaugauaau-3', (SEQ ID NO: 13)
       5'-cgguggacuugagcuuucu-3', (SEQ ID NO: 14)
       5'-ggugguugacaugcaauugu-3',
```

-continued

```
                                   (SEQ ID NO: 15)
5'-cagggaauaugaaggagaa-3', (SEQ ID NO: 16)
5'-ggaggcuucgacaagaaaa-3', (SEQ ID NO: 17)
5'-ccgguggaaccaaugagaa-3', (SEQ ID NO: 18)
5'-ccggcuauauuauagauga-3', (SEQ ID NO: 19)
5'-agaauccaugcacugccaa-3', (SEQ ID NO: 20)
5'-caaggaccuauccaagauu-3', (SEQ ID NO: 21)
5'-caaauauccggcuauauua-3', (SEQ ID NO: 22)
5'-gggacuacgacuacucaga-3', (SEQ ID NO: 23)
5'-gcgaaugcagauacaucga-3', (SEQ ID NO: 24)
5'-gccacaccggaaaugacau-3', (SEQ ID NO: 25)
5'-agaguugaacaggugauua-3', (SEQ ID NO: 26)
5'-gaaccacaaauauccggcu-3', (SEQ ID NO: 27)
5'-cauaagcgaaaugccuucu-3', (SEQ ID NO: 28)
5'-guuuccaccauaagcgaaa-3', (SEQ ID NO: 29)
5'-caggugauuaagcccaaga-3', (SEQ ID NO: 30)
5'-ccacaccggaaaugacauu-3', (SEQ ID NO: 31)
5'-gagtgaaatgccttctagt-3', (SEQ ID NO: 32)
5'-cagagttgaacaggtagtt-3', (SEQ ID NO: 33)
5'-ctggattggacctcaatga-3', (SEQ ID NO: 34)
5'-gaaaactcacagcatgatt-3', (SEQ ID NO: 35)
5'-gaaacttcgacaagagaat-3', (SEQ ID NO: 36)
5'-caggaaatatgaaggagaa-3', (SEQ ID NO: 37)
5'-gcaaatatatagagcacct-3', (SEQ ID NO: 38)
5'-ggtgctgtcgctcttgata-3', (SEQ ID NO: 39)
5'-tcagagttgaacaggtagt-3', (SEQ ID NO: 40)
5'-gaaagaaacttcgacaaga-3', (SEQ ID NO: 41)
5'-gacaatacgtcaggaaata-3', (SEQ ID NO: 42)
5'-caggatatcacattggagt-3', (SEQ ID NO: 43)
5'-ctctttccagtggatcata-3', (SEQ ID NO: 44)
5'-cggctcaggccattatgct-3', (SEQ ID NO: 45)
5'-ggaccacagtgctgatgga-3', (SEQ ID NO: 46)
5'-gctgctggattggacctca-3', (SEQ ID NO: 47)
5'-gttattacagtccagctta-3', (SEQ ID NO: 48)
5'-tggacctcaatgacaccta-3', (SEQ ID NO: 49)
5'-ctggctatattgtcgatga-3', (SEQ ID NO: 50)
5'-gacggaaagtgaaaatact-3', (SEQ ID NO: 51)
5'-gtatgataacgaaccacaa-3', (SEQ ID NO: 52)
5'-acattggagtcactgccaa-3', (SEQ ID NO: 53)
5'-ccaagtcatagccataaat-3', (SEQ ID NO: 54)
5'-agtgaaatgccttctagta-3', (SEQ ID NO: 55)
5'-gataacgaaccacaaatac-3', (SEQ ID NO: 56)
5'-tgcattagcagccatagct-3', (SEQ ID NO: 57)
5'-gcattcacggagaatgcaa-3', (SEQ ID NO: 58)
5'-ggagtcactgccaagtcat-3', (SEQ ID NO: 59)
5'-aggtgcacgaaggtaaaaa-3', (SEQ ID NO: 60)
5'-cagcatgattgacagtagt-3', (SEQ ID NO: 61)
5'-cttagaagacaatacgtca-3', (SEQ ID NO: 62)
5'-agagttgaacaggtagtta-3', (SEQ ID NO: 63)
5'-tgatgagtcggtcctcttt-3', (SEQ ID NO: 64)
5'-atatatagagcacctggaa-3', (SEQ ID NO: 65)
5'-gagttgaacaggtagttaa-3', (SEQ ID NO: 66)
5'-cattcacggagaatgcaaa-3', (SEQ ID NO: 67)
5'-ggacccttttgttatgat-3', (SEQ ID NO: 68)
5'-cagaagagtatgataacga-3',
```

```
                                          (SEQ ID NO: 69)
5'-ccagtggatcataagacaa-3', (SEQ ID NO: 70)
5'-gctgttattacagtccagc-3', (SEQ ID NO: 71)
5'-gggaagcgtgaaccatttt-3', (SEQ ID NO: 72)
5'-cacagtgctgatggatttg-3', (SEQ ID NO: 73)
5'-agtcagagttgaacaggta-3', (SEQ ID NO: 74)
5'-tggaagcagtaacatgcaa-3', (SEQ ID NO: 75)
5'-cacgaaggtaaaaagtatt-3', (SEQ ID NO: 76)
5'-agaagagtatgataacgaa-3', (SEQ ID NO: 77)
5'-gaagcgtgaaccattttct-3', (SEQ ID NO: 78)
5'-ggctatattgtcgatgatt-3', (SEQ ID NO: 79)
5'-gagtcactgccaagtcata-3', (SEQ ID NO: 80)
5'-caatggacccttttgtta-3', (SEQ ID NO: 81)
5'-gcacgaaggtaaaaagtat-3', (SEQ ID NO: 82)
5'-tgaaatgccttctagtagt-3', (SEQ ID NO: 83)
5'-tggatcataagacaatgga-3', (SEQ ID NO: 84)
5'-gtgagtgaaatgccttcta-3', (SEQ ID NO: 85)
5'-gacctcaatgacacctact-3', (SEQ ID NO: 86)
5'-cctcaatgacacctactct-3', (SEQ ID NO: 87)
5'-gctgatggatttgaggtta-3', (SEQ ID NO: 88)
5'-ggaagcagtaacatgcaaa-3', (SEQ ID NO: 89)
5'-cagtaacatgcaaatgtca-3', (SEQ ID NO: 90)
5'-gctatagcataactgaaga-3', (SEQ ID NO: 91)
5'-ggatatcacattggagtca-3', (SEQ ID NO: 92)
5'-cccttttgttatgatggt-3', (SEQ ID NO: 93)
5'-gtatataaaggtgcacgaa-3', (SEQ ID NO: 94)
5'-ggacctcaatgacacctac-3', (SEQ ID NO: 95)
5'-gctcttgatactcggctca-3', (SEQ ID NO: 96)
5'-tgctgctggattggacctc-3', (SEQ ID NO: 97)
5'-gaaccacaaatacctggct-3', (SEQ ID NO: 98)
5'-cggtcctctttccagtgga-3', (SEQ ID NO: 99)
5'-ttccaacacccgctcgttt-3', (SEQ ID NO: 100)
5'-agagcacctggaagcagta-3', (SEQ ID NO: 101)
5'-tctttccagtggatcataa-3', (SEQ ID NO: 102)
5'-ccttttttgttatgatggtt-3', (SEQ ID NO: 103)
5'-cacctggaagcagtaacat-3', (SEQ ID NO: 104)
5'-ctgaggaacgaaagaaact-3', (SEQ ID NO: 105)
5'-gtgaaatgccttctagtag-3', (SEQ ID NO: 106)
5'-ctactctgggaagcgtgaa-3', (SEQ ID NO: 107)
5'-ctgggaagcgtgaaccatt-3', (SEQ ID NO: 108)
5'-actactcagaagagtatga-3', (SEQ ID NO: 109)
5'-catgcaaatgtcagcaaga-3', (SEQ ID NO: 110)
5'-tgaggttacctcaagaagt-3', (SEQ ID NO: 111)
5'-actcggctcaggccattat-3', (SEQ ID NO: 112)
5'-ttcacggagaatgcaaata-3', (SEQ ID NO: 113)
5'-ctgctggattggacctcaa-3', (SEQ ID NO: 114)
5'-tgattcagtcagagttgaa-3', (SEQ ID NO: 115)
5'-tgccaagtcatagccataa-3', (SEQ ID NO: 116)
5'-ctcaagaagtgagatgtct-3', (SEQ ID NO: 117)
5'-gccaagtcatagccataaa-3', (SEQ ID NO: 118)
5'-ctcagaagagtatgataac-3', (SEQ ID NO: 119)
5'-ttctgcattcacggagaat-3', (SEQ ID NO: 120)
5'-taagacaatggaccctttt-3', (SEQ ID NO: 121)
5'-aggttacctcaagaagtga-3', (SEQ ID NO: 122)
5'-aatgccttctagtagtgaa-3',
```

-continued

5'-atgattcagtcagagttga-3' (SEQ ID NO: 123),

5'-aaacaagacggaaagtgaa-3' (SEQ ID NO: 124),

5'-tttctgcattcacggagaa-3' (SEQ ID NO: 125),

5'-caaatacctggctatattg-3' (SEQ ID NO: 126),

5'-tcttccaacacccgctcgt-3' (SEQ ID NO: 127),

5'-gaagcagtaacatgcaaat-3' (SEQ ID NO: 128),

5'-gatgattcagtcagagttg-3' (SEQ ID NO: 129),

5'-tgcattcacggagaatgca-3' (SEQ ID NO: 130),

5'-ctcagtgaggactcctaca-3' (SEQ ID NO: 131),

5'-cactacgagatagccaaca-3' (SEQ ID NO: 132),

5'-cagtcttccactacgagat-3' (SEQ ID NO: 133),

5'-agctcctgagagacaacct-3' (SEQ ID NO: 134),

5'-tcagtcttccactacgaga-3' (SEQ ID NO: 135),

5'-agagacaacctgacgctgt-3' (SEQ ID NO: 136),

5'-ccgaacggtatgaagacat-3' (SEQ ID NO: 137),

5'-ctgaacaggccgaacggta-3' (SEQ ID NO: 138),

5'-ctcctgagagacaacctga-3' (SEQ ID NO: 139),

5'-gacatggcagctttcatga-3' (SEQ ID NO: 140),

5'-cgaacggtatgaagacatg-3' (SEQ ID NO: 141),

5'-agtaccgggagaaggtaga-3' (SEQ ID NO: 142),

5'-acttttcagtcttccacta-3' (SEQ ID NO: 143),

5'-gcatcgagcagaagagcaa-3' (SEQ ID NO: 144),

5'-gcgaaacctgctttccgta-3' (SEQ ID NO: 145),

5'-gtgaaagagtaccgggaga-3' (SEQ ID NO: 146),

5'-gcgatgacaagaagcgcat-3' (SEQ ID NO: 147),

5'-agtcttccactacgagata-3' (SEQ ID NO: 148),

5'-tcagtgaggactcctacaa-3' (SEQ ID NO: 149),

5'-ggtagagaccgagctcaga-3' (SEQ ID NO: 150),

5'-ccgaggtgaaagagtaccg-3' (SEQ ID NO: 151),

5'-caggccgaacggtatgaag-3' (SEQ ID NO: 152),

5'-cggtatgaagacatggcag-3' (SEQ ID NO: 153),

5'-tgctggactcgcacctcat-3' (SEQ ID NO: 154),

5'-aagaagcgcatcatcgatt-3' (SEQ ID NO: 155),

5'-ctggactcgcacctcatca-3' (SEQ ID NO: 156),

5'-ggactcgcacctcatcaaa-3' (SEQ ID NO: 157),

5'-gaagcgcatcatcgattct-3' (SEQ ID NO: 158),

5'-gtcttccactacgagatag-3' (SEQ ID NO: 159),

5'-aaggtagagaccgagctca-3' (SEQ ID NO: 160),

5'-agcgaaacctgctttccgt-3' (SEQ ID NO: 161),

5'-gactactaccgctacctag-3' (SEQ ID NO: 162),

5'-cagagagccgcgtcttcta-3' (SEQ ID NO: 163),

5'-gatgacaagaagcgcatca-3' (SEQ ID NO: 164),

5'-catcgagcagaagagcaac-3' (SEQ ID NO: 165),

5'-tgcagctcctgagagacaa-3' (SEQ ID NO: 166),

5'-acggtatgaagacatggca-3' (SEQ ID NO: 167),

5'-tggactcgcacctcatcaa-3' (SEQ ID NO: 168),

5'-ggcgatgacaagaagcgca-3' (SEQ ID NO: 169),

5'-tgaacaggccgaacggtat-3' (SEQ ID NO: 170),

5'-aggccgaacggtatgaaga-3' (SEQ ID NO: 171),

5'-tcgagcagaagagcaacga-3' (SEQ ID NO: 172),

5'-tccactacgagatagccaa-3' (SEQ ID NO: 173),

5'-ggtgaaagagtaccgggag-3' (SEQ ID NO: 174),

5'-gccgaacggtatgaagaca-3' (SEQ ID NO: 175),

5'-aggagatgccgcctaccaa-3' (SEQ ID NO: 176),

```
                                              (SEQ ID NO: 177)
5'-ggagcgaaacctgctttcc-3', (SEQ ID NO: 178)
5'-cagtgaggactcctacaag-3', (SEQ ID NO: 179)
5'-agcgcatcatcgattctgc-3', (SEQ ID NO: 180)
5'-catcatgcagctcctgaga-3', (SEQ ID NO: 181)
5'-gccgcgtcttctacctgaa-3', (SEQ ID NO: 182)
5'-gagacaacctgacgctgtg-3', (SEQ ID NO: 183)
5'-cgatgacaagaagcgcatc-3', (SEQ ID NO: 184)
5'-cttccactacgagatagcc-3', (SEQ ID NO: 185)
5'-ccactacgagatagccaac-3', (SEQ ID NO: 186)
5'-gctcctgagagacaacctg-3', (SEQ ID NO: 187)
5'-atcatcgattctgcccggt-3', (SEQ ID NO: 188)
5'-tgagagacaacctgacgct-3', (SEQ ID NO: 189)
5'-agacatggcagctttcatg-3', (SEQ ID NO: 190)
5'-tcttccactacgagatagc-3', (SEQ ID NO: 191)
5'-gaacaggccgaacggtatg-3', (SEQ ID NO: 192)
5'-atgcagctcctgagagaca-3', (SEQ ID NO: 193)
5'-accgagctcagaggtgtgt-3', (SEQ ID NO: 194)
5'-cctgagagacaacctgacg-3', (SEQ ID NO: 195)
5'-cacaccctcagtgaggact-3', (SEQ ID NO: 196)
5'-ttccactacgagatagcca-3', (SEQ ID NO: 197)
5'-acatggcagctttcatgaa-3', (SEQ ID NO: 198)
5'-tgacaagaagcgcatcatc-3', (SEQ ID NO: 199)
5'-aaggagatgccgcctacca-3', (SEQ ID NO: 200)
5'-cttttcagtcttccactac-3', (SEQ ID NO: 201)
5'-tcctgagagacaacctgac-3', (SEQ ID NO: 202)
5'-gcagctcctgagagacaac-3', (SEQ ID NO: 203)
5'-agccgcgtcttctacctga-3', (SEQ ID NO: 204)
5'-attctgcccggtcagccta-3', (SEQ ID NO: 205)
5'-actcgcacctcatcaaagg-3', (SEQ ID NO: 206)
5'-agaccgagctcagaggtgt-3', (SEQ ID NO: 207)
5'-gactcgcacctcatcaaag-3', (SEQ ID NO: 208)
5'-agaagcgcatcatcgattc-3', (SEQ ID NO: 209)
5'-gggtgactactaccgctac-3', (SEQ ID NO: 210)
5'-caagaccaccttcgacgag-3', (SEQ ID NO: 211)
5'-ctacgagatagccaacagc-3', (SEQ ID NO: 212)
5'-tttcagtcttccactacga-3', (SEQ ID NO: 213)
5'-aggtgaaagagtaccggga-3', (SEQ ID NO: 214)
5'-aagcgcatcatcgattctg-3', (SEQ ID NO: 215)
5'-gcatcatcgattctgcccg-3', (SEQ ID NO: 216)
5'-aacggtatgaagacatggc-3', (SEQ ID NO: 217)
5'-atcgagcagaagagcaacg-3', (SEQ ID NO: 218)
5'-actactaccgctacctagc-3', (SEQ ID NO: 219)
5'-ttttcagtcttccactacg-3', (SEQ ID NO: 220)
5'-acgagatagccaacagccc-3', (SEQ ID NO: 221)
5'-actaccgctacctagccga-3', (SEQ ID NO: 222)
5'-actacgagatagccaacag-3', (SEQ ID NO: 223)
5'-cccgaggtgaaagagtacc-3', (SEQ ID NO: 224)
5'-cagctcctgagagacaacc-3', (SEQ ID NO: 225)
5'-catcgattctgcccggtca-3', (SEQ ID NO: 226)
5'-gagagacaacctgacgctg-3', (SEQ ID NO: 227)
5'-gcgcatcatcgattctgcc-3', (SEQ ID NO: 228)
5'-gaaggtagagaccgagctc-3', (SEQ ID NO: 229)
5'-tcatcgattctgcccggtc-3', (SEQ ID NO: 230)
5'-gaacggtatgaagacatgg-3',
```

-continued (SEQ ID NO: 231)
5'-cgtaggaattgaggagtgt-3', (SEQ ID NO: 232)
5'-cactacgagatcgccaaca-3', (SEQ ID NO: 233)
5'-gctgtccagtattgagcag-3', (SEQ ID NO: 234)
5'-gaccatgtttcctctcaat-3', (SEQ ID NO: 235)
5'-cgagacaacctgacactgt-3', (SEQ ID NO: 236)
5'-cgtcttccactacgagatc-3', (SEQ ID NO: 237)
5'-cctgcgaagagcgaaacct-3', (SEQ ID NO: 238)
5'-gctgcctctgatcgtagga-3', (SEQ ID NO: 239)
5'-ccaagaccactttcgacga-3', (SEQ ID NO: 240)
5'-gtctgctgggtgtgaccat-3', (SEQ ID NO: 241)
5'-ctctgatcgtaggaattga-3', (SEQ ID NO: 242)
5'-gctgggtgtgaccatgttt-3', (SEQ ID NO: 243)
5'-tggccaagaccactttcga-3', (SEQ ID NO: 244)
5'-cgacaagaagcgcatcatt-3', (SEQ ID NO: 245)
5'-ctgccgagaggactagtat-3', (SEQ ID NO: 246)
5'-gcctctgatcgtaggaatt-3', (SEQ ID NO: 247)
5'-gcgctgttcttgctccaaa-3', (SEQ ID NO: 248)
5'-ctgcctctgatcgtaggaa-3', (SEQ ID NO: 249)
5'-gccctgaacttttccgtct-3', (SEQ ID NO: 250)
5'-tgcctctgatcgtaggaat-3', (SEQ ID NO: 251)
5'-tgaccatgtttcctctcaa-3', (SEQ ID NO: 252)
5'-ccatgtttcctctcaataa-3', (SEQ ID NO: 253)
5'-ggtgacgacaagaagcgca-3', (SEQ ID NO: 254)
5'-acttttccgtcttccacta-3', (SEQ ID NO: 255)
5'-tccgtcttccactacgaga-3', (SEQ ID NO: 256)
5'-ctctcctgcgaagagcgaa-3', (SEQ ID NO: 257)
5'-ccaggaccaggctacttct-3', (SEQ ID NO: 258)
5'-cctgctgcctctgatcgta-3', (SEQ ID NO: 259)
5'-ccgaacgctatgaggacat-3', (SEQ ID NO: 260)
5'-ccctgaacttttccgtctt-3', (SEQ ID NO: 261)
5'-ccgtcttccactacgagat-3', (SEQ ID NO: 262)
5'-gagacaacctgacactgtg-3', (SEQ ID NO: 263)
5'-gcatgtctgctgggtgtga-3', (SEQ ID NO: 264)
5'-tggctgagaactggacagt-3', (SEQ ID NO: 265)
5'-gccgaacgctatgaggaca-3', (SEQ ID NO: 266)
5'-ctgtccagtattgagcaga-3', (SEQ ID NO: 267)
5'-gtattgagcagaaaagcaa-3', (SEQ ID NO: 268)
5'-cagctgttgagcgcaccta-3', (SEQ ID NO: 269)
5'-gacaacctgacactgtgga-3', (SEQ ID NO: 270)
5'-tggagagagccagtctgat-3', (SEQ ID NO: 271)
5'-cgaacgctatgaggacatg-3', (SEQ ID NO: 272)
5'-ggtgctgtccagtattgag-3', (SEQ ID NO: 273)
5'-gaagcgcatcattgactca-3', (SEQ ID NO: 274)
5'-tcgtaggaattgaggagtg-3', (SEQ ID NO: 275)
5'-gctgcgagacaacctgaca-3', (SEQ ID NO: 276)
5'-tgctgtccagtattgagca-3', (SEQ ID NO: 277)
5'-ctgttcttgctccaaaggg-3', (SEQ ID NO: 278)
5'-cctctgatcgtaggaattg-3', (SEQ ID NO: 279)
5'-ccaccggtgacgacaagaa-3', (SEQ ID NO: 280)
5'-gtcttccactacgagatcg-3', (SEQ ID NO: 281)
5'-ctacctgaagatgaagggt-3', (SEQ ID NO: 282)
5'-ctataagaacgtggtgggc-3', (SEQ ID NO: 283)
5'-ctctggccaagaccacttt-3', (SEQ ID NO: 284)
5'-cgctgttcttgctccaaag-3', -continued 5'-ccactttcgacgaggccat-3', (SEQ ID NO: 285)

5'-tgagaactggacagtggca-3', (SEQ ID NO: 286)

5'-ctggccaagaccactttcg-3', (SEQ ID NO: 287)

5'-ttgagcagaaaagcaacga-3', (SEQ ID NO: 288)

5'-tgcgagacaacctgacact-3', (SEQ ID NO: 289)

5'-agctgttgagcgcacctaa-3', (SEQ ID NO: 290)

5'-gaacttttccgtcttccac-3', (SEQ ID NO: 291)

5'-aaaagcaacgaggagggct-3', (SEQ ID NO: 292)

5'-tctcctgcgaagagcgaaa-3', (SEQ ID NO: 293)

5'-ctgttgagcgcacctaacc-3', (SEQ ID NO: 294)

5'-cctgaacttttccgtcttc-3', (SEQ ID NO: 295)

5'-gctgttcttgctccaaagg-3', (SEQ ID NO: 296)

5'-aggccgaacgctatgagga-3', (SEQ ID NO: 297)

5'-attgaggagtgtcccgcct-3', (SEQ ID NO: 298)

5'-gtgaccatgtttcctctca-3', (SEQ ID NO: 299)

5'-caagaccactttcgacgag-3', (SEQ ID NO: 300)

5'-aacttttccgtcttccact-3', (SEQ ID NO: 301)

5'-tgatcgtaggaattgagga-3', (SEQ ID NO: 302)

5'-ggagagagccagtctgatc-3', (SEQ ID NO: 303)

5'-agcaggccgaacgctatga-3', (SEQ ID NO: 304)

5'-aggacatggcagccttcat-3', (SEQ ID NO: 305)

5'-acgacaagaagcgcatcat-3', (SEQ ID NO: 306)

5'-accatgtttcctctcaata-3', (SEQ ID NO: 307)

5'-tgccgagaggactagtatg-3', (SEQ ID NO: 308)

5'-tctgatcgtaggaattgag-3', (SEQ ID NO: 309)

5'-tgggtgtgaccatgtttcc-3', (SEQ ID NO: 310)

5'-tgaacttttccgtcttcca-3', (SEQ ID NO: 311)

-continued

5'-gaattgaggagtgtcccgc-3', (SEQ ID NO: 312)

5'-tttccgtcttccactacga-3', (SEQ ID NO: 313)

5'-ctgctgcctctgatcgtag-3', (SEQ ID NO: 314)

5'-ggccctgaacttttccgtc-3', (SEQ ID NO: 315)

5'-gccaagaccactttcgacg-3', (SEQ ID NO: 316)

5'-tctggccaagaccactttc-3', (SEQ ID NO: 317)

5'-ctgaacttttccgtcttcc-3', (SEQ ID NO: 318)

5'-aagcgcatcattgactcag-3', (SEQ ID NO: 319)

5'-tgttgagcgcacctaacca-3', (SEQ ID NO: 320)

5'-tacctgaagatgaagggtg-3', (SEQ ID NO: 321)

5'-accactttcgacgaggcca-3', (SEQ ID NO: 322)

5'-acgaggccatggctgatct-3', (SEQ ID NO: 323)

5'-gatcccactcttcttgcag-3', (SEQ ID NO: 324)

5'-cttttccgtcttccactac-3', (SEQ ID NO: 325)

5'-gccgagaggactagtatgg-3', (SEQ ID NO: 326)

5'-gctgttgagcgcacctaac-3', (SEQ ID NO: 327)

5'-caggaccaggctacttctc-3', (SEQ ID NO: 328)

5'-cctataagaacgtggtggg-3', (SEQ ID NO: 329)

5'-ctgggtgtgaccatgtttc-3', (SEQ ID NO: 330)

In the present specification, the term "siRNA" means an siRNA specific for a specific gene (for example, a respiratory disease-related gene), preferably, an mRNA encoding amphiregulin or stratifin protein. Further, it will be obvious to those skilled in the art that as long as specificity for the respiratory disease-related gene such as amphiregulin, stratifin, or the like, is maintained, an siRNA having sequences in which one or more bases are substituted, deleted, or inserted in the sense strands having the sequences of SEQ ID NOS: 1 to 330 or the antisense strands complementary thereto is also included in the scope of the present invention.

Further, as long as specificity for amphiregulin or stratifin is maintained, the siRNA according to the present invention includes an siRNA of which a portion of the base sequence of the sense strand does not coincide with a binding site of an amphiregulin or stratifin gene, that is, the base sequence is partially mismatched, as well as an siRNA of which the base sequence of the sense strand is completely (100%) complementary to the binding site of the amphiregulin or stratifin gene, that is, the base sequence perfectly matches the binding site.

The siRNA according to the present invention may include an overhang, which is a structure in which one or more unpaired nucleotides are included at the 3'-end of a single strand or double strands.

In the present invention, the sense or antisense strand is preferably comprised 19 to 31 nucleotides, but is not limited thereto.

In the present invention, an siRNA including a sense strand having any one sequence selected from the group consisting of SEQ ID NOS: 1 to 130 and an antisense strand having the sequence complementary thereto may be specific for amphiregulin. Preferably, the amphiregulin-specific siRNA includes a sense strand having a sequence of SEQ ID NOS: 2, 6 to 9, 11, 17 to 21, 23, 24, 28, 29, 40, 42, 43, 45, 46, 52, 53, 58, 59, 61, 63, 65, 69, 75, 79, 80, 81, 91, 92, 94, 98, 102, 115, 117, 120, or 128, and an antisense strand having a sequence complementary thereto, but is not limited thereto. More preferably, the amphiregulin-specific siRNA comprises a sense strand having a sequence of SEQ ID NOS: 8, 9, 28, 59, 75, 79, 80, 91, 92, or 102, and an antisense strand having a sequence complementary thereto.

In the present invention, an siRNA comprising a sense strand having any one sequence selected from the group consisting of SEQ ID NOS: 131 to 330 and the antisense strand having a sequence complementary thereto may be specific for stratifin. Preferably, the stratifin-specific siRNA comprises a sense strand having a sequence of SEQ ID NOS: 231, 234, 238, 241 to 255, 257, 258, 260 to 263, 267, 268, 270, 272, 273, 275, 278, 283, 284, 290, 297, 299, 300, 302, 303, 307, 311, 314, 320, 324, 326, 327, or 328, and an antisense strand having a sequence complementary thereto, but is not limited thereto. More preferably, the stratifin-specific siRNA comprises a sense strand having a sequence of SEQ ID NOS: 241, 248, 257, 258, 263, 268, 290, or 327, and an antisense strand having a sequence complementary thereto.

In the present invention, the sense strand or antisense strand of the siRNA may include various chemical modifications for improving in vivo stability, imparting resistance against nuclease, and decreasing non-specific immune responses, wherein the chemical modification may be any one or more selected from the group consisting of modification by substitution of a hydroxyl (—OH) group at the 2' carbon position in a sugar structure in nucleotides with only one selected from the group consisting of methyl (—CH$_3$), methoxy (—OCH$_3$), amine (—NH$_2$), fluorine (—F), O-2-methoxyethyl, O-propyl, O-2-methylthioethyl, O-3-aminopropyl, O-3-dimethylaminopropyl, —O—N-methylacetamido and —O-dimethylamidooxyethyl groups; modification by substitution of oxygen in a sugar structure in nucleotides with sulfur; modification of a nucleotide bond into any one selected from the group consisting of a phosphorothioate bond, a boranophosphate bond, or a methyl phosphonate bond; and modification into a peptide nucleic acid (PNA) type, a locked nucleic acid (LNA) type, or a unlocked nucleic acid (UNA) type (*Ann. Rev. Med.*, 55, 61-65 2004; U.S. Pat. Nos. 5,660,985; 5,958,691; 6,531,584; 5,808,023; 6,326,358; 6,175,001; *Bioorg. Med. Chem. Lett.*, 14:1139-1143, 2003; *RNA*, 9:1034-1048, 2003; *Nucleic Acid Res.*, 31:589-595, 2003; *Nucleic Acids Research*, 38(17) 5761-773, 2010; *Nucleic Acids Research*, 39(5) 1823-1832, 2011), but the chemical modifications are not limited thereto.

In the present invention, one or more phosphate groups, preferably, 1 to 3 phosphate groups are bound to a 5'-end of the antisense strand of the siRNA.

In another aspect, the present invention relates to a double-stranded oligo RNA structure comprising a structure represented by the following Structural Formula 1, wherein in the following Structural Formula 1, A is a hydrophilic material, B is a hydrophobic material, X and Y are each independently a simple covalent bond or linker-mediated covalent bond, and R is an siRNA.

A-X-R-Y-B     [Structural Formula 1]

A form of the double-stranded oligo RNA according to the present invention may be preferably a short interfering RNA (siRNA), a short hairpin RNA (shRNA), microRNA (miRNA), and the like, but is not limited thereto. A single-stranded miRNA inhibitor capable of serving as an antagonist for the miRNA may be also included therein.

Hereinafter, the siRNA will be mainly described as the double-stranded oligo RNA according to the present invention, but it is obvious to those skilled in the art that another double-stranded oligo RNA having the same characteristics as those of the double-stranded oligo RNA according to the present invention may also be applied.

In the present invention, the double-stranded oligo RNA structure may comprise a structure represented by the following Structural Formula 2, wherein, in the following Structural Formula 2, S and AS are a sense strand and an antisense strand of the siRNA of Structural Formula 1, respectively, and A, B, X, and Y have the same definitions as those in Structural Formula 1.

$$A—X—S—Y—B \atop AS$$     [Structural Formula 2]

In the present invention, the double-stranded oligo RNA structure may comprise a structure represented by the following Structural Formula 3, wherein, in the following Structural Formula 3, A, B, X, Y, S, and AS have the same definitions as those in Structural Formula 2, and 5' and 3' are a 5'-end and 3'-end of the sense strand of the siRNA, respectively.

$$A—X—5'S\ 3'—Y—B \atop AS$$     [Structural Formula 3]

In the present invention, the double-stranded oligo RNA structure comprises a respiratory disease-related gene-specific siRNA according to the present invention. According to the present invention, in Structural Formulas 1 to 3, an shRNA may be used instead of the siRNA, which is obvious to those skilled in the art.

In the present invention, the hydrophilic material may be polyethylene glycol (PEG), polyvinylpyrrolidone, or polyoxazoline, and preferably, a molecular weight of the hydrophilic material may be preferably 200 to 10,000, but the hydrophilic material is not limited thereto. Preferably, the hydrophilic material is a cationic or non-ionic polymer material.

Particularly, the hydrophilic material A in Structural Formulas 1 to 3 may be used in a form of a hydrophilic material block as represented by the following Structural Formula 4, and problems caused by polydispersity that may occur in a case of using a general synthetic polymer material, or the like, may be significantly solved by using an appropriate number of hydrophilic material blocks as described above (the appropriate number is represented as n in Structural Formula 4) as needed.

$$(A'_m\text{-}J)_n \quad \text{[Structural Formula 4]}$$

In Structural Formula 4, A' is a hydrophilic material monomer, J is a linker linking m hydrophilic material monomers to each other (the number of hydrophilic material monomers is m) or linking m hydrophilic material monomers and the siRNA to each other, m is an integer of 1 to 15, n is an integer of 1 to 10, and the repeating unit represented by $(A'_m\text{-}J)$ corresponds to a base unit of the hydrophilic material block.

In Structural Formula 4, as the hydrophilic material monomer A', any one of monomers of non-ionic hydrophilic polymers may be used as long as it may satisfy the object of the present invention. Preferably, a monomer selected from Compounds (1) to (3) illustrated in Table 1, more preferably, the monomer of Compound (1) may be used, wherein in Compound (1), it is preferable that G is selected from $CH_2$, O, S, and NH.

Particularly, among the hydrophilic material monomers, the monomer of Compound (1) has advantages in that various functional groups may be introduced thereinto, and the monomer of Compound (1) may have good affinity in vivo, and induce little immune response, etc. to thereby have excellent bio-compatibility, and increase stability in vivo of oligo nucleotides included in the structures represented by Structural Formulas 1 to 3 and increase delivery efficiency, such that the monomer of Compound (1) is significantly suitable for preparing the structure according to the present invention.

TABLE 1

Structure of Hydrophilic Material Monomer in the Present Invention

| Compound (1) | Compound (2) | Compound (3) |
| --- | --- | --- |
| 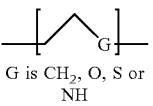 G is $CH_2$, O, S or NH | 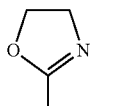 | 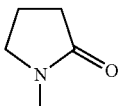 |

It is preferable that a total molecular weight of the hydrophilic material in Structural Formulas 1 to 3 is in a range of 1,000 to 2,000. Therefore, for example, in the case in which hexaethylene glycol is used as the monomer of Compound (1), since a molecular weight of a hexaethylene glycol spacer is 344, a repetition number (n) is preferably 3 to 5.

Particularly, according to the present invention, if necessary, the repeating unit of the hydrophilic group represented by $(A'_m\text{-}J)$ in Structural Formula 4, that is, the hydrophilic material block may be used in an appropriate number represented by n. A', which is the hydrophilic material monomer included in respective hydrophilic material blocks, and J are each independently the same as or different from those in respective hydrophilic material blocks. That is, when three hydrophilic material blocks are used (n=3), for example, the hydrophilic material monomer of Compound (1) may be used in the first block, the hydrophilic material monomer of Compound (2) may be used in the second block, and the hydrophilic material monomer of Compound (3) may be used in the third block. That is, different hydrophilic material monomers are used in the respective hydrophilic material blocks. Alternatively, any one selected from the hydrophilic material monomers of Compounds (1) to (3) may also be equally used in all of the hydrophilic material blocks. Similarly, in the case of the linker mediating the binding between the hydrophilic material monomers, linkers used in the respective hydrophilic material blocks may also be the same as each other or different from each other. In addition, m, the number of hydrophilic material monomers, may be the same as each other or different from each other in the respective hydrophilic material blocks. That is, for example, three hydrophilic material monomers are linked in a first hydrophilic material block (m=3), five hydrophilic material monomers are linked in a second hydrophilic material block (m=5), four hydrophilic material monomers are linked in a third hydrophilic material block (m=4), etc. That is, different numbers of hydrophilic material monomers may be used in all of the hydrophilic material blocks. Alternatively, the same number of hydrophilic material monomers may be used in all of the hydrophilic material blocks.

Further, it is preferable that the linker J is selected from the group consisting of $PO_3^-$, $SO_3$, and $CO_2$, but is not limited thereto. It is obvious to those skilled in the art that any linker may be used depending on the used hydrophilic material monomer, or the like, as long as it may satisfy the object of the present invention.

In the present invention, the hydrophobic material may be a steroid derivative, a glyceride derivative, glycerol ether, polypropylene glycol, an unsaturated or saturated (C12-C50) hydrocarbon, diacylphosphatidylcholine, fatty acid, phospholipid, lipopolyamine, lipid, tocopherol, or tocotrienol, wherein the steroid derivative may be cholesterol, cholestanol, cholic acid, cholesteryl formate, chotestanyl formate, or cholestanyl amine, the glyceride derivative may be mono-, di- or tri-glyceride, the lipid may be cationic lipid, anionic lipid, or hydrophobic lipid. In addition, a molecular weight of the hydrophobic material may be preferably 250 to 1,000, but is not limited thereto.

In the present invention, the hydrophobic material is bound to an opposite distal end of the hydrophilic material, and it does not matter if the hydrophobic material is bound to any position of the sense strand or the antisense strand of the siRNA.

In the present invention, the covalent bonds represented by X and Y may be a non-degradable bond or degradable bond. The non-degradable bond may be an amide bond or phosphorylation bond, and the degradable bond may be a disulfide bond, an acid degradable bond, an ester bond, an anhydride bond, a biodegradable bond or an enzymatically degradable bond, but the present invention is not limited thereto. The linker mediating the covalent bond is not particularly limited as long as the linker may be covalently bound to the hydrophilic material or the hydrophobic material and the end of the amphiregulin or stratifin-specific siRNA, and the bond capable of being decomposed in a specific environment is provided. Therefore, any compound binding the hydrophilic material or hydrophobic material in order to activate the amphiregulin or stratifin-specific siRNA may be used.

In another aspect, the present invention relates to a nanoparticle comprising a double-stranded oligo RNA structure according to the present invention. The double-stranded oligo RNA structure according to the present invention forms self-assembling nanoparticles by a hydrophobic interaction of the hydrophobic materials (Korean Patent Pulication No. 1224828), and since these nanoparticles have significantly excellent delivery in vivo, excellent stability in vivo, and excellent uniformity in particle size, quality control (QC) may be easy, such that a preparation process of the nanoparticles as a drug is simple.

More specifically, the double-stranded oligo RNA structure comprising the amphiregulin or stratifin-specific siRNA is amphipathic structure containing both of the hydrophobic material and the hydrophilic material, wherein hydrophilic portions have affinity through an interaction such as a hydrogen bond, and the like, with water molecules present in the body to be toward the outside and the hydrophobic materials are toward the inside by the hydrophobic interaction therebetween, thereby forming a thermodynamically stable nanoparticle. That is, the hydrophobic material is positioned in the center of the nanoparticle and the hydrophilic material is positioned in an outward direction of the amphiregulin or stratifin-specific siRNA, thereby forming the nanoparticle in a form in which the nanoparticle protects the amphiregulin or stratifin-specific siRNA. The nanoparticle formed as described above may improve intracellular delivery of the amphiregulin or stratifin-specific siRNA and efficiency of the amphiregulin or stratifin-specific siRNA.

In the present invention, the nanoparticle may comprised only a double-stranded oligo RNA structure comprising an siRNA having the same sequence, or formed of a mixture of double-stranded oligo RNA structures comprising siRNAs having different sequences from each other.

In another aspect, the present invention provides a pharmaceutical composition for preventing or treating fibrosis or respiratory diseases, comprising the siRNA, the double-stranded oligo RNA structure, or the nanoparticle according to the present invention as an active ingredient.

The pharmaceutical composition for preventing or treating fibrosis or respiratory diseases may have an effect of preventing or treating fibrosis or respiratory diseases by suppressing connective tissue remodeling, particularly, pulmonary artery remodeling and air way remodeling.

In the present invention, the respiratory disease may be selected from COPD, asthma, acute or chronic bronchitis, allergic rhinitis, cough and phlegm, bronchitis, bronchiolitis, pharyngitis, tonsillitis, and laryngitis, and fibrosis may be selected from IPF, cirrhosis, myelofibrosis, myocardial fibrosis, renal fibrosis, pulmonary fibrosis, lung cancer, and the like, but the respiratory disease and fibrosis are not limited thereto.

The composition according the present invention may be prepared by additionally adding one or more pharmaceutically acceptable carriers for administration in addition to the active ingredient as described above. The pharmaceutically acceptable carrier needs to be compatible with the active ingredient according to the present invention, and a mixture of one or two or more ingredients selected from saline, sterile water, Ringer's solution, buffered saline, a dextrose solution, a maltodextrin solution, glycerol, and ethanol, may be used. In addition, other conventional additives such as an antioxidant, a buffer, a bacteriostatic agent, and the like, may be added thereto as needed. In addition, the composition may be formulated as a formulation for injection, such as an aqueous solution, suspension, emulsion, and the like, by additionally adding a diluent, a dispersant, a surfactant, a binder, and a lubricant thereto. Particularly, it is preferred to provide the composition prepared as a lyophilized formulation. In order to prepare the lyophilized formulation, any method generally known in the technical field to which the present invention pertains may be used, wherein a stabilizer for lyophilization may be added thereto. In addition, the composition may be preferably formulated depending on each disease or ingredient using appropriate methods in the art or a method disclosed in Remington's Pharmaceutical Science (Mack Publishing Company, Easton Pa.).

The composition according to the present invention may be determined by those skilled in the art based on the condition of the patient and the severity of the disease. Further, the composition may be formulated into various forms including powders, tablets, capsules, solutions, injections, ointments, syrups, and the like, and may be provided as a unit-dose container or a multi-dose container, for example, a sealed ampoule, bottle, and the like.

The composition according to the present invention may be, for example, orally or parenterally administered. An example of an administration route of the composition according to the present invention may include oral, intravenous, intramuscular, intra-arterial, intramedullary, intradural, intracardiac, transdermal, subcutaneous, intraperitoneal, intestinal, sublingual or topical administration route, but is not limited thereto. Particularly, the composition according to the present invention may also be administered into the lung via drip infusion in the bronchus for treatment of respiratory diseases. An administration dose of the composition according to the present invention may have various ranges depending on a weight, an age, gender, a health condition, diet, an administration time, an administration method, an excretion rate, or severity of a disease, and the like, of a patient, and be easily determined by a general expert skilled in the art. Further, the composition according to the present invention may be formulated into an appropriate formulation for clinical administration using a method known in the art.

In another aspect, the present invention relates to a lyophilized formulation comprising the pharmaceutical composition according to the present invention.

In another aspect, the present invention relates to a method of preparing a double-stranded oligo RNA structure comprising a respiratory disease-related gene-specific siRNA, the method including: (a) binding a hydrophilic material based on a solid support; (b) synthesizing an RNA single strand based on the solid support containing the hydrophilic material bonded thereto; (c) covalently binding a hydrophobic material to a 5' end of the RNA single strand; (d) synthesizing an RNA single strand having a sequence complementary to a sequence of the RNA single strand; (e) separating and purifying an RNA-polymer structure and the RNA single strand from the solid support when the synthesizing of the RNA single strand is completed; and (f) producing the double-helix oligo RNA structure by annealing the prepared RNA-polymer structure and an RNA single strand having a complementary sequence thereto.

In the present invention, the solid support is controlled pore glass (CPG), polystyrene, silica gel, cellulose paper, but is not limited thereto. In the case in which the solid supporter is the CPG, a diameter is preferably 40 to 180 μm, and a pore size is preferably 500 to 3000 Å, but the solid supporter is not limited thereto.

In the present invention, step (d) is performed before step (a), or during any one step during steps (a) to (c) and step (e).

In the present invention, it may be confirmed whether the desired RNA-polymer structure and the desired RNA single strand were prepared by measuring molecular weights of the purified RNA-polymer structure and the purified RNA single strand after step (e) using a matrix assisted laser desorption/Ionization-time of flight (MALDI-TOF) mass spectrometer. Further, the RNA single strand having a sequence complementary to the sequence of the RNA single strand synthesized in step b) is used in a form in which a phosphate group is bound to a 5'-end thereof.

In another aspect, the present invention relates to a method of preventing or treating fibrosis or respiratory diseases, comprising a step of administering the pharmaceutical composition for preventing or treating fibrosis or respiratory diseases according to the present invention to a subject in need thereof.

In the present invention, the respiratory disease may be COPD, asthma, acute or chronic bronchitis, allergic rhinitis, cough and phlegm, bronchitis, bronchiolitis, pharyngitis, tonsillitis, and laryngitis, and fibrosis may be selected from IPF, cirrhosis, myelofibrosis, myocardial fibrosis, renal fibrosis, pulmonary fibrosis, or lung cancer, but is not limited thereto.

EXAMPLE

Hereinafter, the present invention will be described in detail through the Examples. However, these Examples are only to illustrate the present invention, and those skilled in the art will appreciate that these Examples are not to be construed as limiting a scope of the present invention. Therefore, the substantial scope of the present invention is defined by the accompanying claims and equivalent thereof.

Example 1

Design of Target Base Sequence and Preparation of siRNA

Target base sequences (sense strands) capable of binding to an mRNA sequence (NM_001657.2) of amphiregulin gene (*Homo sapiens*), an mRNA sequence (NM 006142.2) of stratifin gene (*Homo sapiens*), an mRNA sequence (NM 009704.2) of amphiregulin gene (*Mus musculus*), and an mRNA sequence (NM 018754.2) of stratifin gene (*Mus musculus*) were designed, and siRNAs of antisense strands having sequences complementary to the target base sequences were prepared.

First, a gene design program (Turbo si-Designer) developed by Bioneer Co., was used to design the target base sequences to which the siRNA may bind from mRNA sequences of the corresponding genes. The amphiregulin and stratifin-specific siRNAs according to the present invention have a double stranded structure including a sense strand consisting of 19 nucleotides and an antisense strand complementary thereto. Further, siCONT (CUUACGCUGAGUACUUCGA (SEQ ID NO: 331) as a sense strand), an siRNA having a sequence which does not cause inhibition of expression of any gene, was prepared. The siRNA was prepared by linking phosphodiester bonds forming an RNA backbone structure using β-cyanoethyl phosphoramidite (Nucleic Acids Research, 12: 4539-4557, 1984). Specifically, a reaction product including an RNA having a desired length was obtained by repeatedly performing a series of processes of deblocking, coupling, oxidation and capping, on a solid support to which nucleotide was attached, using an RNA synthesizer (384 Synthesizer, BIONEER, Korea). The RNA of the reaction product was separated and purified by HPLC LC918 (Japan Analytical Industry, Japan) equipped with a Daisogel C18 (Daiso, Japan) column, and it was confirmed whether or not the purified RNA meets the target base sequence by MALDI-TOF mass spectrometer (Shimadzu, Japan). Then, an siRNA having any one sequence selected from SEQ ID NOS: 1 to 331 to be desired as a sense strand was prepared by binding the RNA sense and antisense strands to each other.

Example 2

Preparation of Double-stranded Oligo RNA Structure (SAMiRNA LP)

A double-stranded oligo RNA structure (SAMiRNA LP) prepared in the present invention has a structure represented by the following Structural Formula 5.

[Structural Formula 5]

In Structural Formula 5, S is a sense strand of the siRNA; AS is an antisense strand of the siRNA; PEG, which is a hydrophilic material, is polyethylene glycol; C24, which is a hydrophobic material, is tetradocosane including a disulfide bond; and 5' and 3' mean directions of the double-stranded oligo RNA end.

In order to prepare the sense strand of the siRNA of Structural Formula 5, after a double-stranded oligo RNA-hydrophilic material structure of a sense strand of which polyethylene glycol was bound to a 3'-end was synthesized by a method of linking phosphodiester bonds forming an RNA backbone structure using β-cyanoethyl phosphoramidite as in the above-mentioned method, based on 3' polyethylene glycol (PEG, Mn=2,000)-CPG prepared by a method in Example 1 disclosed in the existing Patent Document (Korean Patent Laid-Open Publication No. 10-2012-0119212) as a supporter, and tetradocosane including a disulfide bond was bound to the 5' end thereof, thereby preparing a sense strand of a desired RNA-polymer structure. For the antisense strand to be subjected to annealing together with the strand, the antisense strand having the sequence complementary to that of the sense strand was prepared by the above-mentioned reaction.

When the synthesis was completed, the RNA single strand and the RNA-polymer structure synthesized by treating 28% (v/v) ammonia in a water bath at 60° C. were separated from the CPG, and protecting moieties were removed therefrom by a deprotection reaction. The RNA single strand and the RNA-polymer structure from which the protecting moieties were removed were treated with N-methylpyrrolidone, triethylamine, and triethylaminetrihydrofluoride at a volume ratio of 10:3:4 in an oven at 70° C., thereby removing tert-butyldimethylsilyl (2'TBDMS).

The RNA of the reaction product was separated and purified by HPLC LC918 (Japan Analytical Industry, Japan) equipped with a Daisogel C18 (Daiso, Japan) column, and it was confirmed whether or not the purified RNA meets the target base sequence by MALDI-TOF mass spectrometer (Shimadzu, Japan). Then, in order to prepare each of the double-stranded oligo RNA structures, the sense strand and the antisense strand each having the same amount were mixed with each other, put into a 1× annealing buffer (30 mM 4-(2-hydroxyethyl)-1-piperazineethanesulfonic acid (HEPES), 100 mM potassium acetate, 2 mM magnesium acetate, pH 7.0 to 7.5), reacted in a constant-temperature water bath at 90° C. for 3 minutes, and reacted again at 37° C., thereby preparing each of the double-stranded oligo RNA structures including siRNAs having the sequences of SEQ ID NO: 6, 9, 28, 59, 75, 79, 80, 91, 92, 102, 241, 248, 257, 258, 263, 268, 290, and 327 as the sense strands, respectively, (hereinafter, referred to as SAMiRNALP-mAR, SAMiRNALP-hAR, SAMiRNALP-hSFN, and SAMiRNALP-CONT, respectively). It was confirmed that the prepared double-stranded oligo RNA structure was annealed by electrophoresis.

Example 3

Preparation of Nanoparticle (SAMiRNA) Made of Double-stranded Oligo RNA Structure (SAMiRNA LP) and Measurement of Size Thereof The double-stranded oligo RNA structure (SAMiRNA LP) prepared by Example 2 formed a nanoparticle, that is, a micelle by a hydrophobic interaction between the hydrophobic materials bound to the end of the double-stranded oligo RNA (FIG. 1).

It was confirmed by analyzing polydispersity indexes (PDI) of the nanoparticles formed of SAMiRNALP-hAR, SAMiRNALP-hSFN, SAMiRNALP-mAR, SAMiRNALP-mSFN, and SAMiRNALP-CONT that the nanoparticle (SAMiRNA) formed of the corresponding SAMiRNA LP was formed.

3-1: Preparation of Nanoparticle

The SAMiRNALP-hAR was dissolved in 1.5 ml Dulbecco's phosphate buffered saline (DPBS) at a concentration of 50 μg/ml, the obtained mixture was freeze-dried at −75° C. and 5 mTorr condition for 48 hours to prepare nanoparticle powder, and the nanoparticle powder was dissolved in DPBS (solvent), thereby preparing homogenized nanoparticles.

Nanoparticles formed of SAMiRNALP-hSFN, SAMiRNALP-mAR, SAMiRNALP-mSFN, and SAMiRNALP-CONT were prepared by the same method.

3-2: Measurement of Size and Polydispersity Index (PDI) of Nanoparticles

Sizes of the nanoparticles were measured by zeta-potential measurement. A size of the homogenized nanoparticles prepared by Example 3-1 was measured by zeta-potential measurement (Nano-ZS, MALVERN, England), under conditions in which a refractive index to the material was 1.459, an absorption index was 0.001, a temperature of DPBS (solvent) was 25° C., and the corresponding viscosity and refractive index were 1.0200 and 1.335, respectively. Once measurement was conducted by repeatedly measuring the size 15 times, and the measurement was repeated six times.

The lower the PDI value, the more uniformly distributed the corresponding particles, and thus, it could be appreciated that the nanoparticles according to the present invention were formed to have a significantly uniform size.

Example 4

Inhibition of Expression of Amphiregulin Using Target Gene-Specific siRNA for Mouse in Mouse Fibroblast Cell Line (NIH3T3)

Mouse fibroblast (NIH3T3), which is a fibroblast cell line, was transformed with the amphiregulin-specific siRNAs having sequences of SEQ ID NOS: 1 to 30 as the sense strands, respectively, prepared by Example 1, and an expression pattern of amphiregulin, that is, a degree of inhibition of expression by the siRNA was analyzed in the transformed fibroblast cell line (NIH3T3).

4-1: Culture of Fibroblast Cell Line

The mouse fibroblast cell line (NIH3T3) obtained from American Type Culture Collection (ATCC) was cultured in a RPMI 1640 culture medium (GIBCO/Invitrogen, USA, 10% (v/v) fetal bovine serum, 100 units/ml of penicillin, and 100 μg/ml of streptomycin) under condition of 37° C. and 5% (v/v) $CO_2$.

4-2: Transfection of Target siRNA into Mouse Fibroblast Cell Line

After $1\times10^5$ fibroblast cell lines cultured in Example 4-1 were cultured in a RPMI 1640 culture medium in a 12-well plate under condition of 37° C. and 5% (v/v) $CO_2$ for 18 hours, the medium was removed, and 500 μl of Opti-MEM medium (GIBCO, USA) for each well was dispensed.

Meanwhile, a mixed solution was prepared by mixing 1.5 μl of Lipofectamine™ RNAi Max (Invitrogen, USA) and 248.5 μl of Opti-MEM medium with each other, and the mixed solution was reacted at room temperature for 5 minutes. Then, 20 μl of siRNAs (1 pmole/μl) each having any one sequence of SEQ ID NOS: 1 to 30 as the sense strand, prepared in Example 1, were added to 230 μl of Opti-MEM medium, thereby preparing siRNA solutions each having a final concentration of 20 nM. The mixed solution of Lipofectamine™ RNAi Max was mixed and reacted with the siRNA solution at room temperature for 20 minutes, thereby preparing a transfection solution.

Then, 500 μl of each transfection solution was dispensed in each well containing the tumor cell line and Opti-MEME and incubated for 6 hours, and the Opti-MEM medium was removed. Here, 1 ml of RPMI 1640 culture medium was dispensed into each well, and incubated for 24 hours under condition of 37° C. and 5% (v/v) $CO_2$.

4-3: Quantitative Analysis of Amphiregulin mRNA

After preparing cDNA by extracting a total RNA from the cell line transfected in Example 4-2, an expression amount of the amphiregulin mRNA was relatively quantified using real-time polymerase chain reaction (PCR).

4-3-1: Separation of RNA from Transfected Cell and Preparation of cDNA

The total RNA was extracted from the cell line transfected in Example 4-2 using an RNA extraction kit (AccuPrep Cell total RNA extraction kit, BIONEER, Korea), and the extracted RNA was used to prepare cDNA by RNA reverse transcriptase (AccuPower CycleScript RT Premix/dT20, Bioneer, Korea) according to the following method. Specifically, the extracted RNA (1 μg/tube) was added to AccuPower CycleScript RT Premix/dT20 (Bioneer, Korea) contained in 0.25 ml Eppendorf tube, and distilled water treated with diethyl pyrocarbonate (DEPC) was added thereto so as to have a total volume of 20 μl. A process of hybridizing the RNA and primers at 30° C. for 1 minute by a gene amplifier (MyGenie™ 96 Gradient Thermal Block, BIONEER, Korea) and a process of preparing the cDNA at 52° C. for 4 minutes were repeated 6 times, and then, an amplification reaction was terminated by inactivating an enzyme at 95° C. for 5 minutes.

4-3-2: Relative Quantitative Analysis of Amphiregulin mRNA

A relative amount of the amphiregulin mRNA was quantified by the following method through real-time PCR using the cDNA prepared by Example 4-3-1 as a template. The cDNA prepared in Example 4-3-1 was diluted 5 times with distilled water in each well of a 96-well plate. Then, in order to analyze an expression amount of the amphiregulin mRNA, 3 μl of the diluted cDNA, 10 μl of 2× GreenStar™ PCR master mix (BIONEER, Korea), 6 μl of distilled water, and 1 μl of amphiregulin qPCR primers (SEQ ID NOS: 336 and 337 (Table 2); each 10 pmole/μl; BIONEER, Korea) were added thereto to prepare each mixed solution. Meanwhile, in order to normalize the expression amount of the amphiregulin mRNA, RPL13A (60S ribosomal protein L13a), which is a housekeeping gene (hereinafter, referred to as HK gene) was used as a reference gene. The following reaction was performed on the 96-well plate containing the mixed solution using Exicycler™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C.

Figure 2:
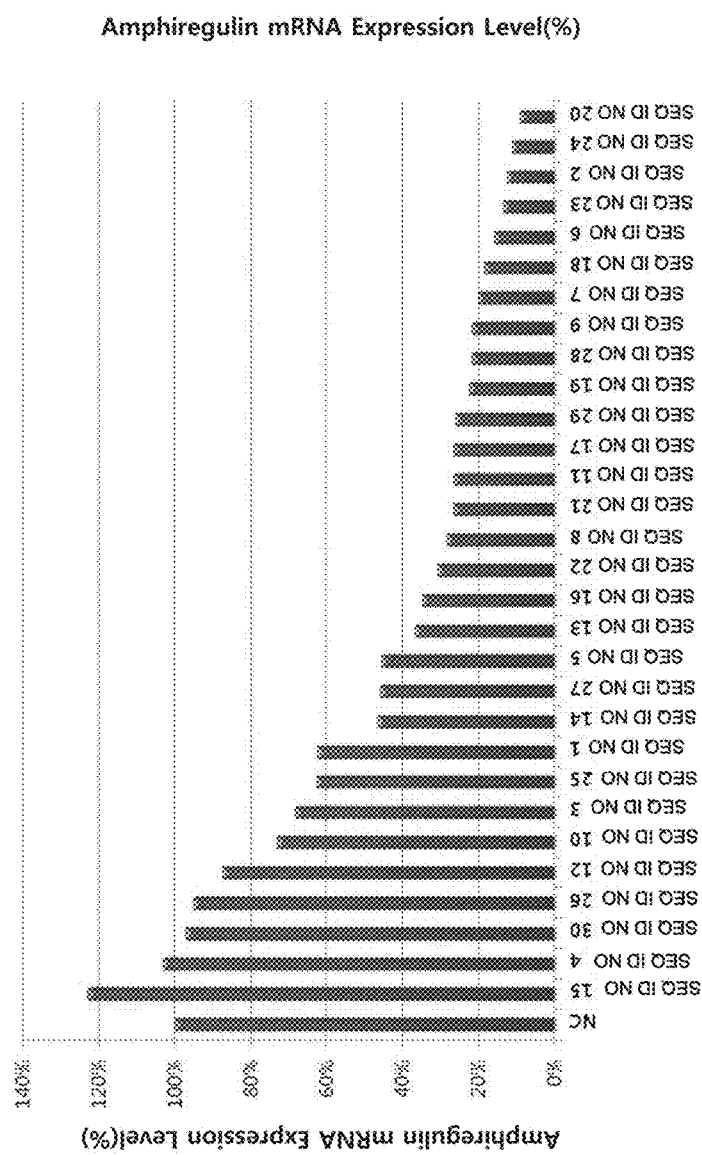
FIG. 2, which illustrates results obtained by quantitatively analyzing expression amounts of amphiregulin mRNA in Example 4, is a graph illustrating relative expression amounts (%) of amphiregulin mRNA confirmed after transforming mouse fibroblast cell lines with 30 kinds of mice amphiregulin-specific siRNAs having the sequences of SEQ ID NOS: 1 to 30 according to the present invention as sense strands, respectively, at a concentration of 20 nM. NC indicates an expression amount of amphiregulin mRNA in a total RNA obtained in a cell line (control group) which was not treated with the mouse amphiregulin-specific siRNA, and relative expression amounts of the amphiregulin mRNA depending on the respective siRNAs measured based on the NC (100%) are illustrated in FIG. 2.

After PCR was terminated, for a threshold cycle (Ct) value of each of the obtained target genes, Ct values of the target genes corrected through the RPL13A gene were calculated, and then a Ct value difference (ΔCt) was obtained using a test group treated with the siRNA (si-CONT) having a control sequence, not causing inhibition of gene expression, as a control group. The expression amount of the target gene in the cell treated with each of the amphiregulin-specific siRNAs (having sequences of SEQ ID NOS: 1 to 30 as the sense strands, respectively) was relatively quantified by using the ΔCt value and Calculation Equation, 2(-ΔCt)×100 (FIG. 2).

In order to select a high-efficiency siRNA, 15 kinds of siRNAs in which the expression amount of the amphiregulin mRNA was significantly decreased by 70% or more, as compared to the control group at a final concentration of 20 nM, and which had sequences of SEQ ID NOS: 2, 6 to 9, 11, 17 to 21, 23, 24, 28, and 29 as the sense strands, respectively, were selected.

TABLE 2

Sequence Information of Primer for qPCR

| Primer | Sequence | SEQ ID NO |
|---|---|---|
| mRPL13A-F | CGATAGTGCATCTTGGCCTTT | 332 |
| mRPL13A-R | CCTGCTGCTCTCAAGGTTGTT | 333 |
| hRPL13A-F | AGCTCATGAGGCTACGGAAA | 334 |
| hRPL13A-R | CGTACATTCCAGGGCAACA | 335 |
| mAR-F | GGTCTTAGGCTCAGGCCATTA | 336 |
| mAR-R | CGCTTATGGTGGAAACCTCT | 337 |
| hAR-F | ACACCTACTCTGGGAAGCGT | 338 |
| hAR-R | GCCAGGTATTTGTGGTTCGT | 339 |
| mSFN-F | GTGTGTGCGACACCGTACT | 340 |
| mSFN-R | CTCGGCTAGGTAGCGGTAG | 341 |
| hSFN-F | AGAAGCGCATCATTGACTCAG | 342 |
| hSFN-R | TCTCGTAGTGGAAGACGGAAA | 343 |

(Here, m indicates a mouse-specific sequence; h indicates a human-specific sequence, AR indicates an amphiregulin-specific sequence, SFN indicates a stratifin-specific sequence, F indicates a forward primer, and R indicates a reverse primer)

Example 5

Inhibition of Expression of Amphiregulin Using siRNA Selected from Fibroblast Cell Line (NIH3T3)

Mouse fibroblast cells (NIH3T3), which are the fibroblast cell lines, were transformed with the siRNAs having the sequences of SEQ ID NOS: 2, 6 to 9, 11, 17 to 21, 23, 24, 28, and 29 as the sense strands, respectively, selected in Example 4, and an expression profile of the amphiregulin mRNA in the transformed fibroblast cell line (NIH3T3) was analyzed.

5-1: Culture of Fibroblast Cell Line

The mouse fibroblast cell line (NIH3T3) obtained from American Type Culture Collection (ATCC) was cultured in a RPMI 1640 culture medium (GIBCO/Invitrogen, USA, 10% (v/v) fetal bovine serum, 100 units/ml of penicillin, and 100 μg/ml of streptomycin) under condition of 37° C. and 5% (v/v) $CO_2$.

5-2: Transfection of Target siRNA into Fibroblast Cell Line

After $1 \times 10^5$ fibroblast cell lines cultured in Example 5-1 were cultured in a RPMI 1640 culture medium in a 12-well plate under condition of 37° C. and 5% (v/v) $CO_2$ for 18 hours, the medium was removed, and 500 μl of Opti-MEM medium (GIBCO, USA) for each well was dispensed.

Meanwhile, a mixed solution was prepared by mixing 2 μl of Lipofectamine™ RNAi Max (Invitrogen, USA) and 248 μl of Opti-MEM medium with each other, and the mixed solution was reacted at room temperature for 5 minutes. Then, 5 μl of siRNAs (1 pmole/μl) each having any one sequence of SEQ ID NOS: 2, 6 to 9, 11, 17 to 21, 23, 24, 28, and 29 as the sense strand, selected in Example 4, were added to 245 μl of Opti-MEM medium, thereby preparing siRNA solutions each having a final concentration of 5 nM. The mixed solution of Lipofectamine™ RNAi Max was mixed and reacted with the siRNA solution at room temperature for 20 minutes, thereby preparing a transfection solution.

Then, 500 μl of each transfection solution was dispensed in each well of the tumor cell line containing Opti-MEM dispensed therein, and cultured for 6 hours, and the Opti-MEM medium was removed. Here, 1 ml of RPMI 1640 culture medium was dispensed therein and cultured under condition of 37° C. and 5% (v/v) $CO_2$ for 24 hours.

5-3: Quantitative Analysis of Amphiregulin mRNA

After preparing cDNA by extracting a total RNA from the cell line transfected in Example 5-2, an expression amount of the amphiregulin mRNA was relatively quantified using real-time PCR.

5-3-1: Separation of RNA from Transfected Cell and Preparation of cDNA

The total RNA was extracted from the cell line transfected in Example 5-2 using an RNA extraction kit (AccuPrep Cell total RNA extraction kit, BIONEER, Korea), and the extracted RNA was used to prepare cDNA by RNA reverse transcriptase (AccuPower CycleScript RT Premix/dT20, Bioneer, Korea) according to the following method. Specifically, the extracted RNA (1 μg/tube) was added to AccuPower CycleScript RT Premix/dT20 (Bioneer, Korea) contained in 0.25 ml Eppendorf tube, and distilled water treated with diethyl pyrocarbonate (DEPC) was added thereto so as to have a total volume of 20 μl. A process of hybridizing the RNA and primers at 30° C. for 1 minute by a gene amplifier (MyGeniem™ 96 Gradient Thermal Block, BIONEER, Korea) and a process of preparing the cDNA at 52° C. for 4 minutes were repeated 6 times, and then, an amplification reaction was terminated by inactivating an enzyme at 95° C. for 5 minutes.

5-3-2: Relative Quantitative Analysis of Amphiregulin mRNA

A relative amount of the amphiregulin mRNA was quantified by the following method through real-time PCR using the cDNA prepared by Example 5-3-1 as a template. The cDNA prepared in Example 5-3-1 was diluted 5 times with distilled water in each well of a 96-well plate. Then, in order to analyze an expression amount of the amphiregulin mRNA, 3 μl of the diluted cDNA, 10 μl of 2× GreenStar™ PCR master mix (BIONEER, Korea), 6 μl of distilled water, and 1 μl of amphiregulin qPCR primers (SEQ ID NOS: 336 and 337 (Table 2); each 10 pmole/μl; BIONEER, Korea) were added thereto to prepare each mixed solution. Meanwhile, in order to normalize the expression amount of the amphiregulin mRNA, RPL13A, which is a housekeeping gene, was used as a reference gene. The following reaction was performed on the 96-well plate containing the mixed solution using Exicycler™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C. After PCR was terminated, for a threshold cycle (Ct) value of each of the obtained target genes, Ct values of the target genes corrected through the RPL13A gene were calculated, and then a Ct value difference (ΔCt) was obtained using a test group treated with the siRNA (siCONT) having a control sequence, not causing inhibition of gene expression, as a control group. The expression amount of the target gene in the cell treated with each of the amphiregulin-specific siRNAs was relatively quantified by using the ΔCt value and Calculation Equation, 2(−ΔCt)×100, such that changes in Expression amount of the mRNA by the amphiregulin-specific siRNAs having sequences of SEQ ID NOS: 2, 6 to 9, 11, 17 to 21, 23, 24, 28, and 29 as the sense strands, respectively, were relatively quantified.

In order to select high-efficiency siRNAs, an IC50, which is a value at which expression of a target gene is inhibited by 50% after treatment with an siRNA, was confirmed, thereby selecting three kinds of siRNAs having the sequences of SEQ ID NOS: 8, 9, and 28 as the sense strands, respectively, showing the largest decrease in the expression amount of the amphiregulin mRNA at the final concentration of 5 nM as compared to the control group.

Example 6

Inhibition of Expression of Amphiregulin Using siRNA Selected from Fibroblast Cell Line (NIH3T3)

Mouse fibroblast cells (NIH3T3), which are the fibroblast cell lines, were transformed with the siRNAs having the sequences of SEQ ID NOS: 8, 9, and 29 as the sense strands, respectively, selected in Example 5, and an expression profile of the amphiregulin mRNA in the transformed fibroblast cells (NIH3T3) was analyzed, thereby confirming an $IC_{50}$ value of the siRNA.

6-1: Culture of Fibroblast Cell Line

The mouse fibroblast cell line (NIH3T3) obtained from American Type Culture Collection (ATCC) was cultured in a RPMI 1640 culture medium (GIBCO/Invitrogen, USA, 10% (v/v) fetal bovine serum, 100 units/ml of penicillin, and 100 μg/ml of streptomycin) under condition of 37° C. and 5% (v/v) $CO_2$.

6-2: Transfection of Target siRNA into Fibroblast Cell Line

After 1×10⁵ fibroblast cell lines cultured in Example 6-1 were cultured in a RPMI 1640 culture medium in a 12-well plate under condition of 37° C. and 5% (v/v) $CO_2$ for 18 hours, the medium was removed, and 500 μl of Opti-MEM medium (GIBCO, USA) for each well was dispensed.

Meanwhile, a mixed solution was prepared by mixing 2 μl of Lipofectamine™ RNAi Max (Invitrogen, USA) and 248 μl of Opti-MEM medium with each other, and the mixed solution was reacted at room temperature for 5 minutes. Then, 0.2, 1, and 5 μl of siRNAs (1 pmole/μl) having sequences of SEQ ID NOS: 8, 9, and 28 as the sense strands, respectively, selected in Example 4, were added to 249.8, 249, and 245 μl of Opti-MEM medium, respectively, thereby preparing siRNA solutions each having a final concentration of 0.2, 1, and 5 nM. The mixed solution of Lipofectamine™ RNAi Max was mixed and reacted with the siRNA solution at room temperature for 20 minutes, thereby preparing a transfection solution.

Then, 500 μl of each transfection solution was dispensed in each well of the tumor cell line containing Opti-MEM dispensed therein, and cultured for 6 hours, and the Opti-MEM medium was removed. Here, 1 ml of RPMI 1640 culture medium was dispensed therein and cultured under condition of 37° C. and 5% (v/v) $CO_2$ for 24 hours.

6-3: Quantitative Analysis of Amphiregulin mRNA

After preparing cDNA by extracting a total RNA from the cell line transfected in Example 6-2, an expression amount of the amphiregulin mRNA was relatively quantified using real-time polymerase chain reaction (PCR).

6-3-1: Separation of RNA from Transfected Cell and Preparation of cDNA

The total RNA was extracted from the cell line transfected in Example 6-2 using an RNA extraction kit (AccuPrep Cell total RNA extraction kit, BIONEER, Korea), and the extracted RNA was used to prepare cDNA by RNA reverse transcriptase (AccuPower CycleScript RT Premix/dT20, Bioneer, Korea) according to the following method. Specifically, the extracted RNA (1 μg/tube) was added to AccuPower CycleScript RT Premix/dT20 (Bioneer, Korea) contained in 0.25 ml Eppendorf tube, and distilled water treated with diethyl pyrocarbonate (DEPC) was added thereto so as to have a total volume of 20 μl. A process of hybridizing the RNA and primers at 30° C. for 1 minute by a gene amplifier (MyGenie™ 96 Gradient Thermal Block, BIONEER, Korea) and a process of preparing the cDNA at 52° C. for 4 minutes were repeated 6 times, and then, an amplification reaction was terminated by inactivating an enzyme at 95° C. for 5 minutes.

6-3-2: Relative Quantitative Analysis of Amphiregulin mRNA

Figure 3:
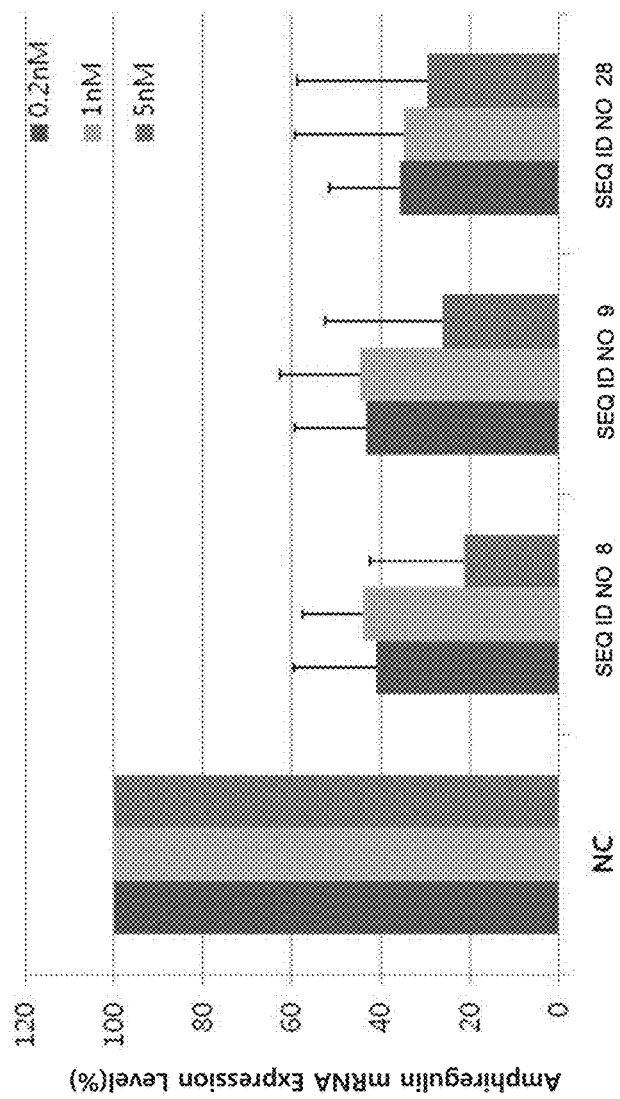
FIG. 3, which illustrates results obtained by quantitatively analyzing expression amounts of amphiregulin mRNA in Example 6, is a graph illustrating relative expression amounts (%) of amphiregulin mRNA confirmed after transforming mouse fibroblast cell lines with siRNAs having the sequences of SEQ ID NOS: 8, 9, and 28 according to the present invention as sense strands, respectively, at different concentrations of the siRNAs (0.2, 1, and 5 nM).

A relative amount of the amphiregulin mRNA was quantified by the following method through real-time PCR using the cDNA prepared by Example 6-3-1 as a template. The cDNA prepared in Example 6-3-1 was diluted 5 times with distilled water in each well of a 96-well plate. Then, in order to analyze an expression amount of the amphiregulin mRNA, 3 μl of the diluted cDNA, 10 μl of 2× GreenStar™ PCR master mix (BIONEER, Korea), 6 μl of distilled water, and 1 μl of amphiregulin qPCR primers (SEQ ID NOS: 336 and 337 (Table 2); each 10 pmole/μl; BIONEER, Korea) were added thereto to prepare each mixed solution. Meanwhile, in order to normalize the expression amount of the amphiregulin mRNA, RPL13A, which is a housekeeping gene, was used as a reference gene. The following reaction was performed on the 96-well plate containing the mixed solution using Exicycler™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C. After PCR was terminated, for a threshold cycle (Ct) value of each of the obtained target genes, Ct values of the target genes corrected through the RPL13A gene were calculated, and then a Ct value difference (ΔCt) was obtained using a test group treated with the siRNA (siCONT) having a control sequence, not causing inhibition of gene expression, as a control group. The expression amount of the target gene in the cell treated with each of the amphiregulin-specific siRNAs was relatively quantified by using the ΔCt value and Calculation Equation, 2(−ΔCt)×100 (FIG. 3).

As a result, in the cases of all of the amphiregulin-specific siRNAs having the sequences of SEQ ID NOS: 8, 9, and 28 as the sense strands, respectively, the expression amount of the amphiregulin mRNA was decreased by 50% or more even at a low concentration of 0.2 nM. Therefore, it was confirmed that the amphiregulin-specific siRNAs had an effect highly efficiently inhibiting expression of amphiregulin.

Example 7

Design of Target Base Sequence and Preparation of siRNA

Human lung cancer cell line (A549), which is a lung tumor cell line, was transformed using the siRNAs having the sequences of SEQ ID NOS: 31 to 130 and 231 to 330 as the sense strands, respectively, prepared in Example 1, and an expression profile of a target gene in the transformed lung cancer cell line (A549) was analyzed.

7-1: Culture of Human Lung Cancer Cell Line

The human lung cancer cell line (A549) obtained from American Type Culture Collection (ATCC) was cultured in a DMEM culture medium (GIBCO/Invitrogen, USA, 10% (v/v) fetal bovine serum, 100 units/ml of penicillin, and 100 μg/ml of streptomycin) under condition of 37° C. and 5% (v/v) $CO_2$.

7-2: Transfection of Target siRNA into Human Lung Cancer Cell Line

After 1.2×10$^5$ lung cancer cell lines (A549) cultured in Example 7-1 were cultured in a DMEM medium in a 6-well plate under condition of 37° C. and 5% (v/v) $CO_2$ for 18 hours, the medium was removed, and 500 μl of Opti-MEM medium (GIBCO, USA) for each well was dispensed.

Meanwhile, a mixed solution was prepared by mixing 3.5 μl of Lipofectamine™ RNAi Max (Invitrogen, USA) and 246.5 μl of Opti-MEM medium with each other, and the mixed solution was reacted at room temperature for 5 minutes. Then, 1 μl of the siRNAs (1 pmole/μl) having sequences of SEQ ID NOS: 31 to 130 and 231 to 330 as the sense strands, respectively, prepared in Example 1, were added to 230 μl of Opti-MEM medium, thereby preparing siRNA solutions each having a final concentration of 1 nM. The mixed solution of Lipofectamine™ RNAi Max was mixed and reacted with the siRNA solution at room temperature for 15 minutes, thereby preparing a transfection solution.

Then, 500 μl of each transfection solution was dispensed in each well of the tumor cell line containing Opti-MEM dispensed therein, and cultured for 6 hours, and the Opti-MEM medium was removed. Here, 1 ml of RPMI 1640 culture medium was dispensed therein and cultured under condition of 37° C. and 5% (v/v) $CO_2$ for 24 hours.

7-3: Quantitative Analysis of Target Gene mRNA

After preparing cDNA by extracting a total RNA from the cell line transfected in Example 7-2 by the same method as in Example 4-3, an expression amount of the target gene mRNA was relatively quantified using real-time polymerase chain reaction (PCR).

7-4: Separation of RNA from Transfected Cell and Preparation of cDNA

The total RNA was extracted from the cell line transfected in Example 7-2 using an RNA extraction kit (AccuPrep Cell total RNA extraction kit, BIONEER, Korea), and the extracted RNA was used to prepare cDNA by RNA reverse transcriptase (AccuPower CycleScript RT Premix/dT20, Bioneer, Korea) according to the following method. Specifically, the extracted RNA (1 μg/tube) was added to AccuPower CycleScript RT Premix/dT20 (Bioneer, Korea) contained in 0.25 ml Eppendorf tube, and distilled water treated with diethyl pyrocarbonate (DEPC) was added thereto so as to have a total volume of 20 μl. A process of hybridizing the RNA and primers at 30° C. for 1 minute by a gene amplifier (MyGenie™ 96 Gradient Thermal Block, BIONEER, Korea) and a process of preparing the cDNA at 52° C. for 4 minutes were repeated 6 times, and then, an amplification reaction was terminated by inactivating an enzyme at 90° C. for 5 minutes.

7-5: Relative Quantitative Analysis of Target Gene mRNA

A relative amount of a respirator disease-related gene mRNA was quantified by the following method through real-time PCR using the cDNA prepared by Example 7-4 as a template. The cDNA prepared in Example 7-4 was diluted 5 times with distilled water in each well of a 96-well plate. Then, in order to analyze an expression amount of the target gene mRNA, 3 μl of the diluted cDNA, 25 μl of 2× GreenStar™ PCR master mix (BIONEER, Korea), 19 μl of distilled water, and 3 μl of qPCR primers (amphiregulin gene, SEQ ID NOS: 338 and 339; stratifin gene, SEQ ID NOS: 342 and 343 (Table 2), F and R: each 10 pmole/μl; BIONEER, Korea) were added thereto to prepare each mixed solution. Meanwhile, in order to normalize the expression amount of the target gene mRNA, RPL13A, which is a housekeeping gene (hereinafter, referred to as HK gene) was used as a reference gene. The following reaction was performed on the 96-well plate containing the mixed solution using Exicycler™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C. After PCR was terminated, for a threshold cycle (Ct) value of each of the obtained target genes, Ct values of the target genes corrected through the RPL13A gene were calculated, and then a Ct value difference (ΔCt) was obtained using a test group treated with the siRNA (siCONT) having a control sequence, not causing inhibition of gene expression, as a control group.

Figure 4:
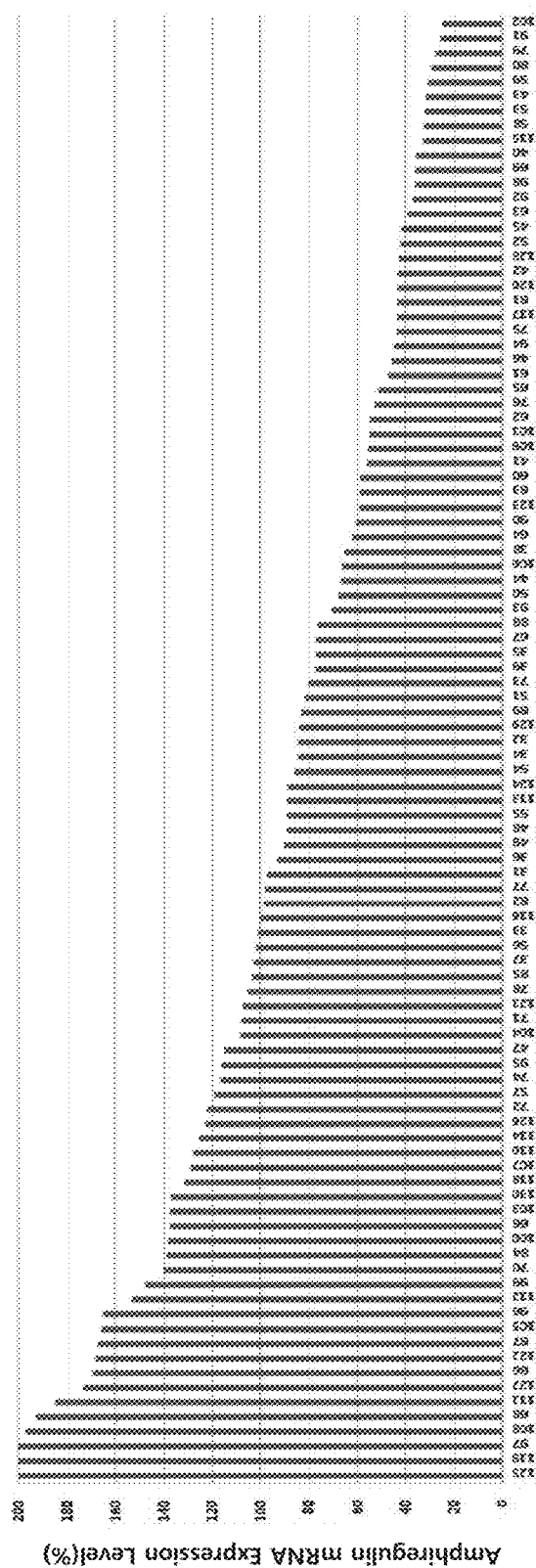
FIG. 4, which illustrates results obtained by quantitatively analyzing expression amounts of amphiregulin mRNA in Example 7, is a graph illustrating relative expression amounts (%) of amphiregulin mRNA confirmed after transforming human lung tumor cell lines with 100 kinds of human amphiregulin-specific siRNAs having the sequences of SEQ ID NOS: 31 to 130 according to the present invention as sense strands, respectively, at a concentration of 1 nM.
Figure 5:
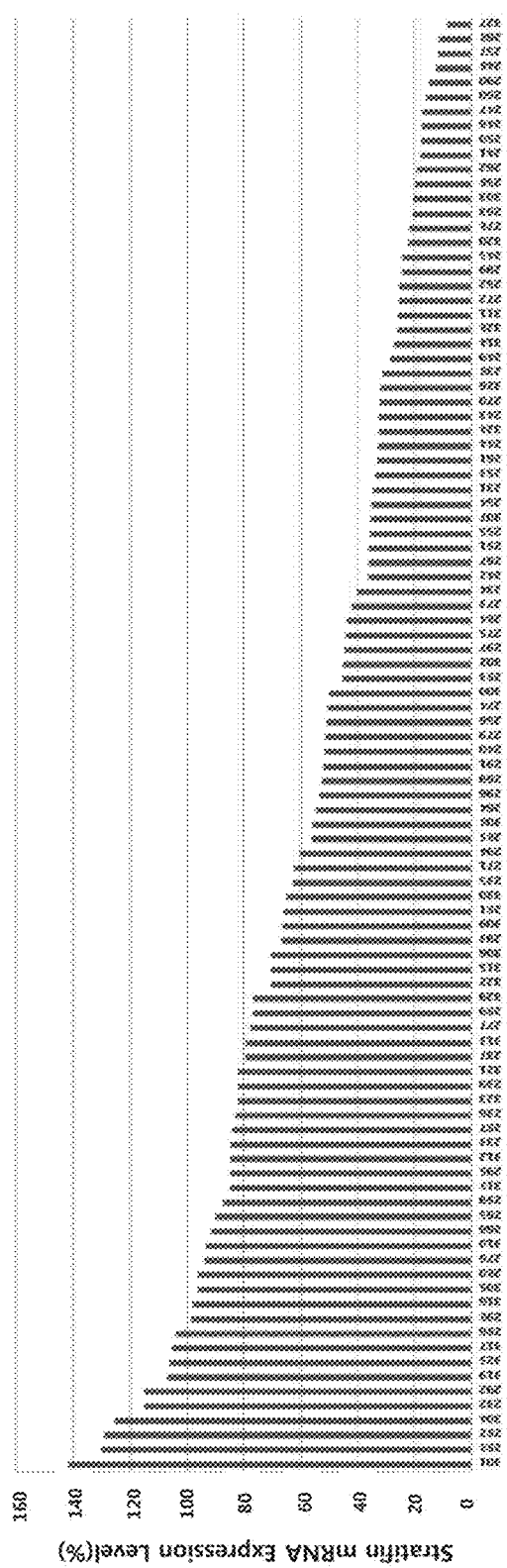
FIG. 5, which illustrates results obtained by quantitatively analyzing expression amounts of stratifin mRNA in Example 7, is a graph illustrating relative expression amounts (%) of stratifin mRNA confirmed after transforming human lung tumor cell lines with 100 kinds of human stratifin-specific siRNAs having the sequences of SEQ ID NOS: 231 to 330 according to the present invention as sense strands, respectively, at a concentration of 1 nM.

The expression amount of the target gene in the cell treated with each of the amphiregulin (*Homo sapiens*)-specific siRNAs (having sequences of SEQ ID NOS: 31 to 130 as the sense strands, respectively) was relatively quantified by using the ΔCt value and Calculation Equation, 2(-ΔCt)×100 (FIG. 4).

Further, the expression amount of the target gene in the cell treated with each of the stratifin (*Homo sapiens*)-specific siRNAs (having sequences of SEQ ID NOS: 231 to 330 as the sense strands, respectively) was relatively quantified.

Figure 6:
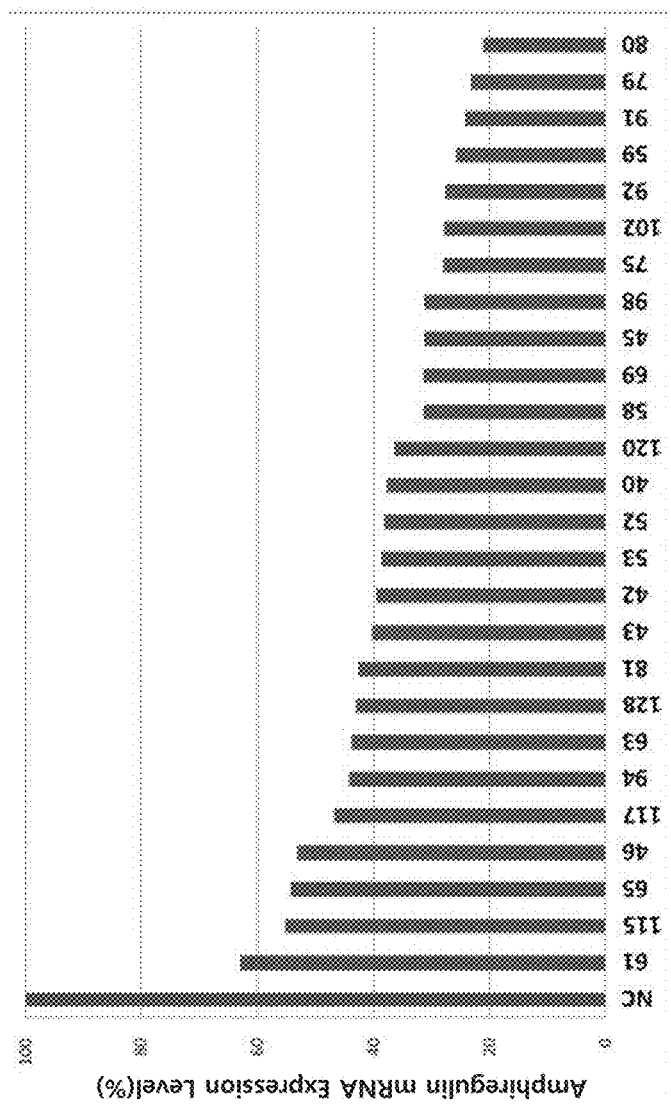
FIG. 6, which illustrates results obtained by quantitatively analyzing expression amounts of amphiregulin mRNA in Example 8, is a graph illustrating relative expression amounts (%) of amphiregulin mRNA in transformed cell lines after transforming lung cancer cell lines with 26 kinds of human amphiregulin-specific siRNAs having the sequences of SEQ ID NOS: 40, 42, 43, 45, 46, 52, 53, 58, 59, 61, 63, 65, 69, 75, 79, 80, 81, 91, 92, 94, 98, 102, 115, 117, 120, and 128 according to the present invention as sense strands, respectively, at a concentration of 0.2 nM.
Figure 7:
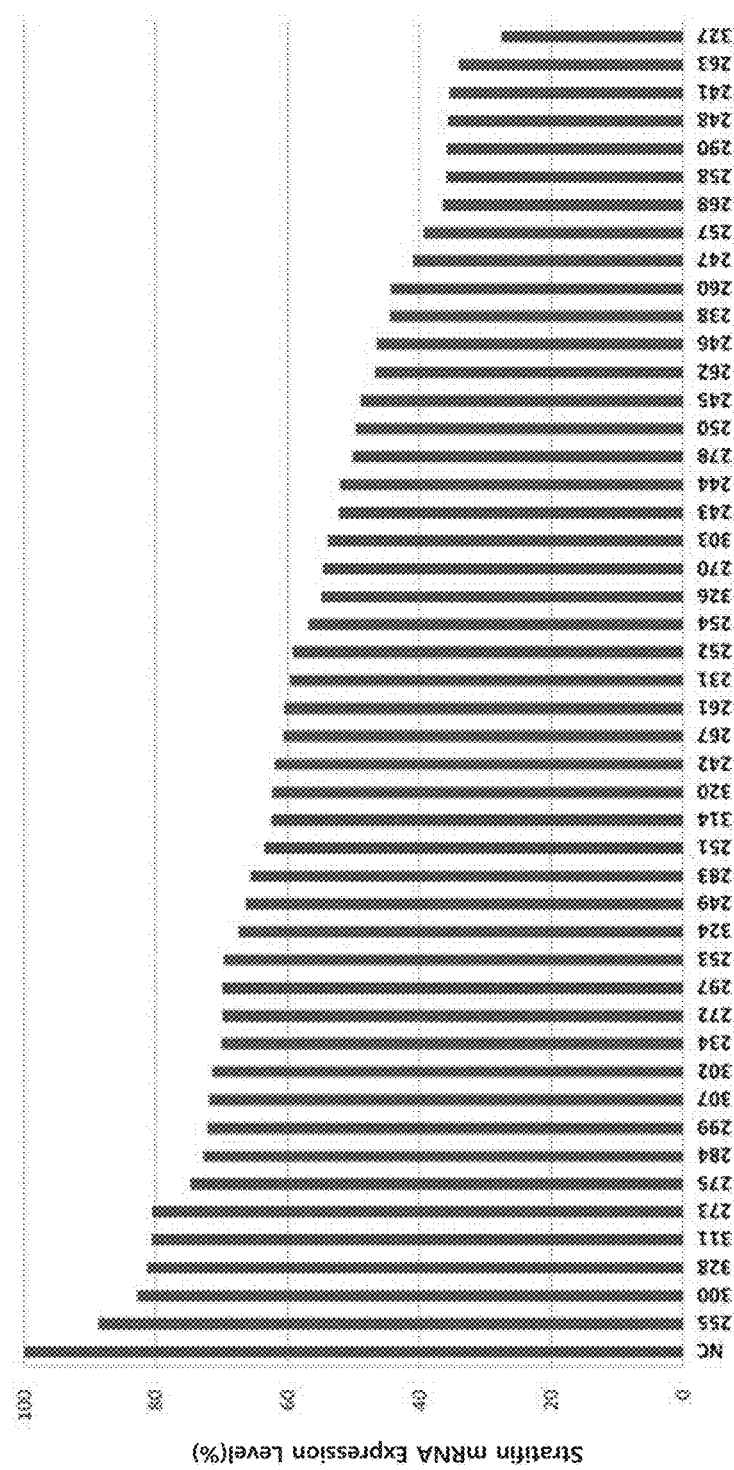
FIG. 7, which illustrates results obtained by quantitatively analyzing expression amounts of stratifin mRNA in Example 8, is a graph illustrating relative expression amounts (%) of stratifin mRNA in transformed cell lines after transforming lung cancer cell lines with 47 kinds of human stratifin-specific siRNAs having the sequences of SEQ ID NOS: 231, 234, 238, 241, 242, 243, 244, 245, 246, 247, 248, 249, 250, 251, 252, 253, 254, 255, 257, 258, 260, 261, 262, 263, 267, 268, 270, 272, 273, 275, 278, 283, 284, 290, 297, 299, 300, 302, 303, 307, 311, 314, 320, 324, 326, 327, and 328 according to the present invention as sense strands, respectively, at a concentration of 0.2 nM.

As a result, in the cases of 26 kinds of human amphiregulin-specific siRNA and 47 kinds of human stratifin-specific siRNAs, expression of the target gene was inhibited by 50% or more at a concentration of 1 nM in the present invention, and thus it may be confirmed that these siRNAs highly efficiently inhibited expression of the target gene (see FIGS. 6 and 7).

Example 8

Selection of High-Efficiency Amphiregulin and Stratifin-Specific siRNAs for Human in Human Lung Cancer Cell Line (A549)

Human lung cancer cell line (A549) was transformed using 26 kinds of human amphiregulin-specific siRNAs and 47 kinds of human stratifin-specific siRNAs having the sequences selected in Example 7-5 as the sense strands, respectively, and an expression profile of a target gene in the transformed lung cancer cell line (A549) was analyzed, thereby selecting high-efficiency siRNAs.

8-1: Culture of Human Lung Cancer Cell Line

Human lung cancer cell line (A549) obtained from American Type Culture Collection (ATCC) was cultured under the same conditions as those in Example 7-1.

8-2: Transfection of Target siRNA into Human Lung Cancer Cell Line

After $1.2 \times 10^5$ lung cancer cell lines (A549) cultured in Example 8-1 were cultured in a DMEM medium in a 6-well plate under condition of 37° C. and 5% (v/v) $CO_2$ for 18 hours, the medium was removed, and 500 µl of Opti-MEM medium (GIBCO, USA) for each well was dispensed.

Meanwhile, a mixed solution was prepared by mixing 3.5 µl of Lipofectamine™ RNAi Max (Invitrogen, USA) and 246.5 µl of Opti-MEM medium with each other, and the mixed solution was reacted at room temperature for 5 minutes. Then, 0.2 µl of siRNAs (that is, 26 kinds of human amphiregulin-specific siRNAs and 47 kinds of human stratifin-specific siRNAs, 1 pmole/µl) having the sequences selected in Example 7-5 as the sense strands, respectively, were added to 230 µl of Opti-MEM medium, thereby preparing siRNA solutions each having a final concentration of 0.2 nM. The mixed solution of Lipofectamine™ RNAi Max was mixed and reacted with the siRNA solution at room temperature for 15 minutes, thereby preparing a transfection solution.

Then, 500 µl of each transfection solution was dispensed in each well of the tumor cell line containing Opti-MEM dispensed therein, and cultured for 6 hours, and the Opti-MEM medium was removed. Here, 1 ml of RPMI 1640 culture medium was dispensed therein and cultured under condition of 37° C. and 5% (v/v) $CO_2$ for 24 hours.

8-3: Quantitative Analysis of Target Gene mRNA

After preparing cDNA by extracting a total RNA from the cell line transfected in Example 8-2 by the same method as in Example 4-3, an expression amount of the target gene mRNA was relatively quantified using real-time polymerase chain reaction (PCR).

8-4: Separation of RNA from Transfected Cell and Preparation of cDNA

The total RNA was extracted from the cell line transfected in Example 8-2 using an RNA extraction kit (AccuPrep Cell total RNA extraction kit, BIONEER, Korea), and the extracted RNA was used to prepare cDNA by RNA reverse transcriptase (AccuPower CycleScript RT Premix/dT20, Bioneer, Korea) according to the following method. Specifically, the extracted RNA (1 µg/tube) was added to AccuPower CycleScript RT Premix/dT20 (Bioneer, Korea) contained in 0.25 ml Eppendorf tube, and distilled water treated with diethyl pyrocarbonate (DEPC) was added thereto so as to have a total volume of 20 µl. A process of hybridizing the RNA and primers at 30° C. for 1 minute by a gene amplifier (MyGenie™ 96 Gradient Thermal Block, BIONEER, Korea) and a process of preparing the cDNA at 52° C. for 4 minutes were repeated 6 times, and then, an amplification reaction was terminated by inactivating an enzyme at 90° C. for 5 minutes.

8-5: Relative Quantitative Analysis of Target Gene mRNA

A relative amount of a respirator disease-related gene mRNA was quantified by the following method through real-time PCR using the cDNA prepared by Example 8-4 as a template. The cDNA prepared in Example 8-4 was diluted 5 times with distilled water in each well of a 96-well plate. Then, in order to analyze an expression amount of the target gene mRNA, 3 µl of the diluted cDNA, 25 µl of 2× GreenStar™ PCR master mix (BIONEER, Korea), 19 µl of distilled water, and 3 µl of qPCR primers (amphiregulin gene, SEQ ID NOS: 338 and 339; stratifin gene, SEQ ID NOS: 342 and 343 (Table 2), F and R: each 10 pmole/µl; BIONEER, Korea) were added thereto to prepare each mixed solution. Meanwhile, in order to normalize an expression amount of the target gene mRNA, RPL13A, which is a housekeeping gene, was used as a reference gene. The following reaction was performed on the 96-well plate containing the mixed solution using Exicyclerm ™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C. After PCR was terminated, for a threshold cycle (Ct) value of each of the obtained target genes, Ct values of the target genes corrected through the RPL13A gene were calculated, and then a Ct value difference (ΔCt) was obtained using a test group treated with the siRNA (si-CONT) having a control sequence, not causing inhibition of gene expression, as a control group.

The expression amount of the target gene in the cell treated with each of the amphiregulin (*Homo sapiens*)-specific siRNAs was relatively quantified by using the ΔCt value and Calculation Equation, 2(−ΔCt)×100 (FIG. 6).

In addition, the expression amount of the target gene in the cell treated with each of the stratifin (*Homo sapiens*)-specific siRNAs was relatively quantified (FIG. 7).

As a result, in the cases of 7 kinds of high-efficiency human amphiregulin-specific siRNAs (SEQ ID NOS: 59, 75, 79, 80, 91, 92, and 102), expression of human amphiregulin was inhibited by 70% or more at a concentration of 0.2 nM in the present invention, and in the cases of 8 kinds of high-efficiency human stratifin-specific siRNAs (SEQ ID NOS: 241, 248, 257, 258, 263, 268, 290, and 327), expression of human stratifin was inhibited by 60% or more at a concentration of 0.2 nM in the present invention. Therefore, it may be confirmed that these siRNAs may highly efficiently inhibit expression of the target gene.

Example 9

Inhibition of Expression of Target Gene in Tumor Cell Line Using Nanoparticle Made of SAMiRNA Human lung cancer cell line (A549) was transformed using nanoparticles made of SAMiRNAs prepared in Example 3-1 using 3 kinds of human amphiregulin-specific siRNAs having the sequences of SEQ ID NOS: 79, 80, and 91 and 5 kinds of human stratifin-specific siRNAs having the sequences of SEQ ID NOS: 248, 257, 268, 290, and 327 selected in Example 8-5 as the sense strands, respectively, and an expression profile of a target gene in the transformed lung cancer cell line (A549) was analyzed.

9-1: Culture of Human Lung Cancer Cell Line

Human lung cancer cell line (A549) obtained from American Type Culture Collection (ATCC) was cultured under the same conditions as those in Example 7-1.

9-2: Transformation of Human Lung Cancer Cell Line Using Nanoparticle Made of SAMiRNA After 0.8×10$^5$ human lung cancer cell lines (A549) cultured in Example 9-1 were cultured in a DMEM medium in a 12-well plate under condition of 37° C. and 5% (v/v) CO$_2$ for 18 hours. In order to prepare transfection solutions of SAMiRNA containing the amphiregulin-specific siRNAs (SEQ ID NOS: 79, 80, and 91) and the stratifin-specific siRNAs (SEQ ID NOS: 248, 257, 268, 290, and 327) at concentrations of 50 nM, 100 nM, 200 nM, 500 nM, 13.3 μl, respectively, 26.6 μl, 53.2 μl, and 133.0 μl of SAMiRNAs and 986.7 μl, 973.4 μl, 976.8 μl, and 867.0 μl of Opti-MEM medium (GIBCO, USA) were mixed with each other so as to have a total volume of 1 ml. After the cell culture medium was removed, 1 ml of each transfection solution was treated in each well, and the cells were cultured under condition of 37° C. and 5% (v/v) CO$_2$. The transfection solution was replaced with a new solution every 12 hours, and this process was repeated 4 times for 48 hours.

9-3: Quantitative Analysis of Target Gene mRNA

After preparing cDNA by extracting a total RNA from the cell line transfected in Example 9-2 by the same method as in Example 4-3, an expression amount of the target gene mRNA was relatively quantified using real-time polymerase chain reaction (PCR).

9-4: Separation of RNA from Transfected Cell and Preparation of cDNA

The total RNA was extracted from the cell line transfected in Example 9-2 using an RNA extraction kit (AccuPrep Cell total RNA extraction kit, BIONEER, Korea), and the extracted RNA was used to prepare cDNA by RNA reverse transcriptase (AccuPower RocketScript RT Premix/dT20, Bioneer, Korea) according to the following method. Specifically, the extracted RNA (1 μg/tube) was added to AccuPower RocketScript RT Premix/dT20 (Bioneer, Korea) contained in 0.25 ml Eppendorf tube, and distilled water treated with diethyl pyrocarbonate (DEPC) was added thereto so as to have a total volume of 20 μl. A process of hybridizing the RNA and primers at 30° C. for 1 minute by a gene amplifier (MyGenie™ 96 Gradient Thermal Block, BIONEER, Korea) and a process of preparing the cDNA at 52° C. for 4 minutes were repeated 6 times, and then, an amplification reaction was terminated by inactivating an enzyme at 90° C. for 5 minutes.

9-5: Relative Quantitative Analysis of Target Gene mRNA

A relative amount of a respirator disease-related gene mRNA was quantified by the following method through real-time PCR using the cDNA prepared by Example 9-4 as a template. The cDNA prepared in Example 9-4 was diluted 5 times with distilled water in each well of a 96-well plate. Then, in order to analyze an expression amount of the target gene mRNA, 3 μl of the diluted cDNA, 25 μl of 2× GreenStar ™ PCR master mix (BIONEER, Korea), 19 μl of distilled water, and 3 μl of qPCR primers (amphiregulin gene, SEQ ID NOS: 338 and 339; stratifin gene, SEQ ID NOS: 342 and 343 (Table 2), F and R: each 10 pmole/μl; BIONEER, Korea) were added thereto to prepare each mixed solution. Meanwhile, in order to normalize an expression amount of the target gene mRNA, RPL13A, which is a housekeeping gene, was used as a reference gene. The following reaction was performed on the 96-well plate containing the mixed solution using Exicyclerm ™ 96 Real-Time Quantitative Thermal Block (BIONEER, Korea). After performing the reaction at 95° C. for 15 minutes to activate an enzyme and remove a secondary structure of the cDNA, four processes composed of a process of denaturing at 94° C. for 30 seconds, a process of annealing at 58° C. for 30 seconds, a process of extension at 72° C. for 30 seconds, and a process of SYBR green scan were repeated 42 times, and final extension was performed at 72° C. for 3 minutes. Then, the temperature was maintained at 55° C. for 1 minute, and a melting curve was analyzed from 55° C. to 95° C. After PCR was terminated, for a threshold cycle (Ct) value of each of the obtained target genes, Ct values of the target genes corrected through the RPL13A gene were calculated, and then a Ct value difference (ΔCt) was obtained using a test group treated with the SAMiRNA-CONT (siCONT) having a control sequence, not causing inhibition of gene expression, as a control group.

Figure 8:
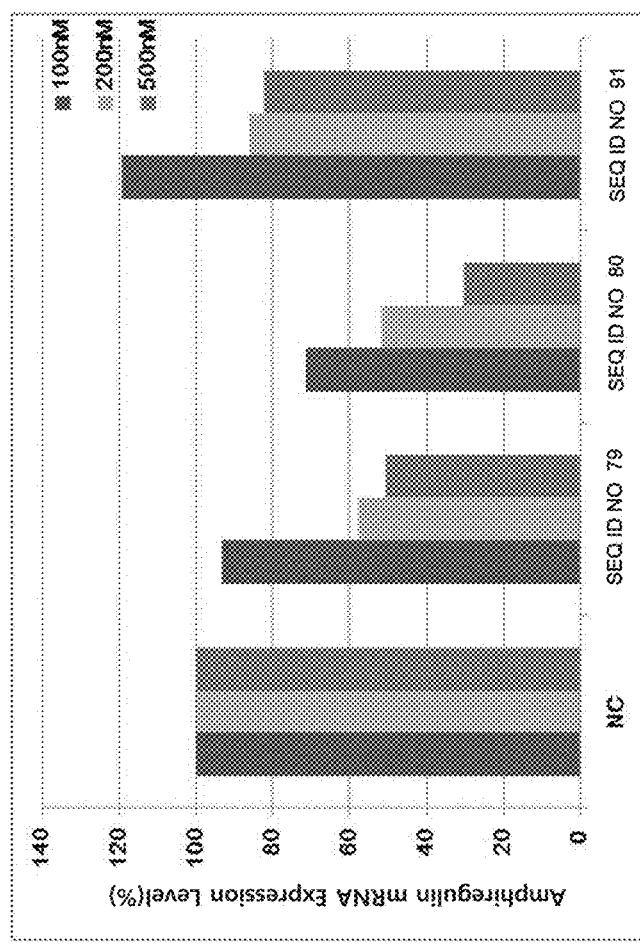
FIG. 8, which illustrates results obtained by quantitatively analyzing expression amounts of amphiregulin mRNA in Example 9, is a graph illustrating relative expression amounts (%) of amphiregulin mRNA in transformed cell lines after transforming human lung cancer cell lines with 3 kinds of human amphiregulin-specific SAMiRNA having the sequences of SEQ ID NOS: 79, 80, and 91 according to the present invention as the sense strands, respectively, at different concentrations of 100, 200, and 500 nM.

The expression amount of the target gene in the cell treated with each of the amphiregulin (*Homo sapiens*)-specific SAMiRNAs was relatively quantified by using the ΔCt value and Calculation Equation, 2(−ΔCt)×100 (FIG. 8).

Figure 9:
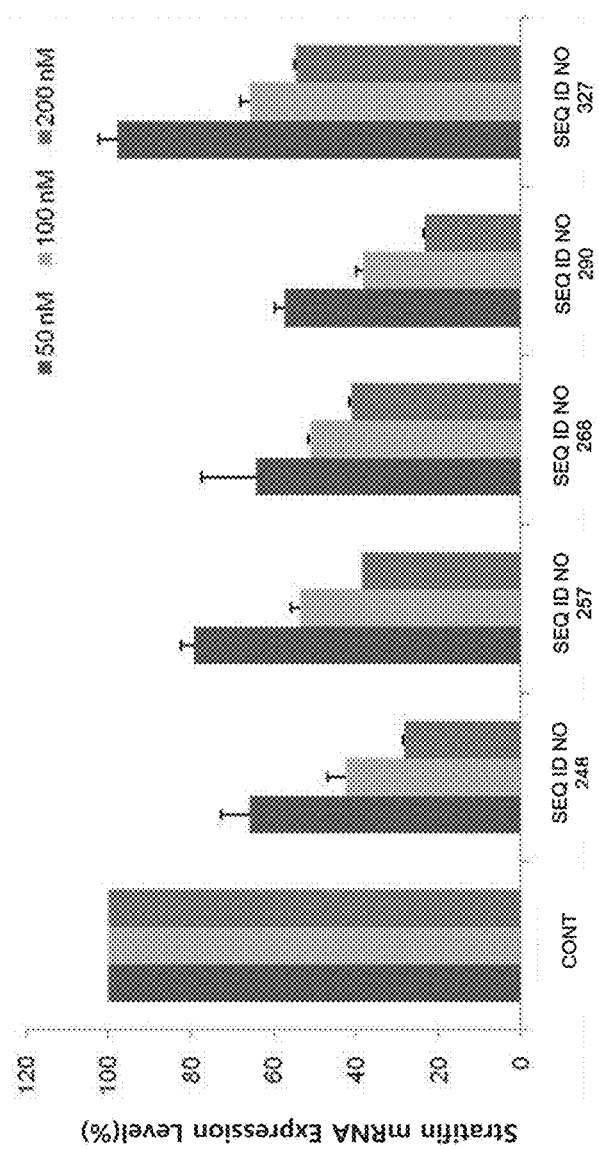
FIG. 9, which illustrates results obtained by quantitatively analyzing expression amounts of stratifin RNA in Example 9, is a graph illustrating relative expression amounts (%) of stratifin mRNA in transformed cell lines after transforming human lung cancer cell lines with 5 kinds of human stratifin-specific SAMiRNA having the sequences of SEQ ID NOS: 248, 257, 268, 290, and 327 as the sense strands, respectively, at different concentrations of 50, 100, and 200 nM.

In addition, the expression amount of the target gene in the cell treated with each of the stratifin (*Homo sapiens*)-specific SAMiRNAs was relatively quantified (FIG. 9).

As a result, it was confirmed that at the time of treating the human lung cancer cell line (A549) with SAMiRNA-hAR (#80), and SAMiRNA-hSFN (#248, #290) at a concentration of 500 nM or 200 nM, expression of the target gene of the human lung cancer cell line (A549) was inhibited by 70%.

INDUSTRIAL APPLICABILITY

Since an siRNA according to the present invention may significantly efficiently inhibit expression of a respiratory disease-related gene, particularly, amphiregulin or stratifin, the siRNA according to the present invention, a double-stranded oligo RNA structure containing the same, and a nanoparticle containing the double-stranded oligo RNA structure may be usefully used to prevent or treat fibrosis or respiratory diseases.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. An siRNA comprising a sense strand comprising a sequence of SEQ ID NO: 59, 75, 80, 92, 98, 102, or 107, wherein when the sense strand comprises the sequence of SEQ ID NO: 107, the sense strand contains no more than 19 nucleotides; and an antisense strand having a sequence complementary thereto.

2. The siRNA of claim 1, wherein SEQ ID NO: 107 is the sense strand.

3. The siRNA of claim 1, wherein the siRNA comprises a sense strand comprising a sequence of SEQ ID NO: 59, 75, 80, 92, 98, or 102, and an antisense strand comprising a sequence complementary thereto.

4. The siRNA of claim 1, wherein the sense strand or antisense strand of the siRNA comprise chemical modification wherein the chemical modification is any one or more selected from the group consisting of modification by substitution of a hydroxyl (—OH) group at the 2' carbon position in a sugar structure in nucleotides with only one selected from the group consisting of methyl (—CH₃), methoxy (—OCH₃), amine (—NH₂), fluorine (—F), O-2-methoxyethyl, O-propyl, O-2-methylthioethyl, O-3-aminopropyl, O-3-dimethylaminopropyl, —O—N-methylacetamido and —O-dimethylamidooxyethyl groups;
modification by substitution of oxygen in a sugar structure in nucleotides with sulfur;
modification of a nucleotide bond into any one selected from the group consisting of a phosphorothioate bond, a boranophosphate bond, or a methyl phosphonate bond; and
modification into a peptide nucleic acid (PNA) type, a locked nucleic acid (LNA) type, or a unlocked nucleic acid (UNA) type.

5. The siRNA of claim 1, wherein one or more phosphate groups are bound to a 5'-end of the antisense strand of the siRNA.

6. A double-stranded oligo RNA structure comprising a structure represented by the following Structural Formula 1:

A-X-R-Y-B      [Structural Formula 1]

wherein A is a hydrophilic material, B is a hydrophobic material, X and Y are each independently a simple covalent bond or linker-mediated covalent bond, and R is the siRNA of claim 1.

7. The double-stranded oligo RNA structure of claim 6, wherein the structure comprises a structure represented by the following Structural Formula 2:

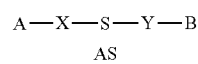
         [Structural Formula 2]

wherein S and AS are a sense strand and an antisense strand of the siRNA of claim 6, respectively, and A, B, X, and Y have the same definitions as those in claim 6.

8. The double-stranded oligo RNA structure of claim 7, wherein the structure comprises a structure represented by the following Structural Formula 3:

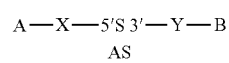
         [Structural Formula 3]

wherein A, B, X, Y, S, and AS have the same definitions as those in claims 6, and 5' and 3' are a 5'-end and 3'-end of the sense strand of the siRNA, respectively.

9. The double-stranded oligo RNA structure of claim 6, wherein the hydrophilic material is represented by the following Structural Formula 4:

(A'ₘ-J)ₙ      [Structural Formula 4]

wherein A' is a hydrophilic material monomer, J is a linker linking m hydrophilic material monomers to each other or linking m hydrophilic material monomers and the siRNA to each other, m is an integer of 1 to 15, n is an integer of 1 to 10,
wherein A' is a compound selected from Compounds (1) to (3) represented as follows:

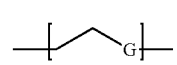
         Compound (1)

wherein G is selected for the group consisting of CH₂, O, S and NH,

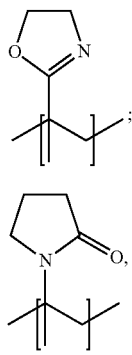

Compound (2);

Compound (3)

and wherein J is selected from the group consisting of $PO_3$—, $SO_3$, and $CO_2$.

10. The double-stranded oligo RNA structure of claim 6, wherein a molecular weight of the hydrophilic material is 200 to 10,000.

11. The double-stranded oligo RNA structure of claim 6, wherein the hydrophilic material is polyethylene glycol (PEG), polyvinylpyrrolidone, or polyoxazoline.

12. The double-stranded oligo RNA structure of claim 6, wherein a molecular weight of the hydrophobic material is 250 to 1,000.

13. The double-stranded oligo RNA structure of claim 6, wherein the hydrophobic material is a steroid derivative, a glyceride derivative, glycerol ether, polypropylene glycol, an unsaturated or saturated (C12-C50) hydrocarbon, diacyl-phosphatidylcholine, fatty acid, phospholipid, lipopolyamine, lipid, tocopherol, or tocotrienol.

14. The double-stranded oligo RNA structure of claim 13, wherein the steroid derivative is cholesterol, cholestanol, cholic acid, cholesteryl formate, chotestanyl formate, or cholestanyl amine.

15. The double-stranded oligo RNA structure of claim 13, wherein the glyceride derivative is a mono-, di- or tri-glyceride.

16. The double-stranded oligo RNA structure of claim 6, wherein each of the covalent bonds represented by X and Y is a non-degradable bond or degradable bond.

17. The double-stranded oligo RNA structure of claim 16, wherein the non-degradable bond is an amide bond or phosphorylation bond.

18. The double-stranded oligo RNA structure of claim 16, wherein the degradable bond is a disulfide bond, an acid degradable bond, an ester bond, an anhydride bond, a biodegradable bond or an enzymatically degradable bond.

19. A nanoparticle comprising the double-stranded oligo RNA structure of claim 6.

20. The nanoparticle of claim 19, wherein the nanoparticle comprises a mixture of double-stranded oligo RNA structures comprising siRNAs having different sequences from each other.

21. A pharmaceutical composition for preventing or treating fibrosis or respiratory diseases comprising the siRNA of claim 1 as an active ingredient.

22. A lyophilized formulation comprising the pharmaceutical composition of claim 21.

23. A pharmaceutical composition for preventing or treating fibrosis or respiratory diseases comprising the double-stranded oligo RNA structure of claim 6.

24. A lyophilized formulation comprising the pharmaceutical composition of claim 23.

25. A pharmaceutical composition for preventing or treating fibrosis or respiratory diseases comprising the nanoparticle of claim 19.

26. A lyophilized formulation comprising the pharmaceutical composition of claim 25.

27. A method of preventing or treating fibrosis or respiratory diseases, comprising administering a pharmaceutical composition comprising the siRNA of claim 1, a double-stranded oligo RNA structure comprising said siRNA, or a nanoparticle comprising said double-stranded oligo RNA structure.

28. The method of claim 27, wherein the respiratory disease is COPD, asthma, acute or chronic bronchitis, allergic rhinitis, cough and phlegm, bronchitis, bronchiolitis, pharyngitis, tonsillitis, or laryngitis.

29. The method of claim 27, wherein the fibrosis comprises IPF, cirrhosis, myelofibrosis, myocardial fibrosis, renal fibrosis, or pulmonary fibrosis.

* * * * *

UNITED STATES PATENT AND TRADEMARK OFFICE
CERTIFICATE OF CORRECTION

PATENT NO. : 10,208,309 B2  
APPLICATION NO. : 15/301713  
DATED : February 19, 2019  
INVENTOR(S) : Jeiwook Chae Page 1 of 1

It is certified that error appears in the above-identified patent and that said Letters Patent is hereby corrected as shown below:

In the Specification

Column 28, Line 15: the Structural Formula 5:

C24—5'S—S—3'—PEG

"          AS          "

Should be:

C24—5'—S—3'—PEG

--          AS          --

Signed and Sealed this  
Twenty-sixth Day of March, 2019

Andrei Iancu  
*Director of the United States Patent and Trademark Office*